(12) United States Patent
Grosse-Hovest et al.

(10) Patent No.: US 9,023,996 B2
(45) Date of Patent: May 5, 2015

(54) ANTI-FLT3 ANTIBODIES

(75) Inventors: Ludger Grosse-Hovest, Tuebingen (DE); Hans-Joerg Buehring, Tuebingen (DE); Martin Hofmann, Tuebingen (DE); Steffen Aulwurm, Hechingen (DE); Grundram Jung, Rottenburg-Wendelsheim (DE)

(73) Assignee: Synimmune GmbH, Tuebingen (DE)

( * ) Notice: Subject to any disclaimer, the term of this patent is extended or adjusted under 35 U.S.C. 154(b) by 0 days.

(21) Appl. No.: 13/518,779

(22) PCT Filed: Dec. 23, 2010

(86) PCT No.: PCT/EP2010/070659
§ 371 (c)(1),
(2), (4) Date: Sep. 10, 2012

(87) PCT Pub. No.: WO2011/076922
PCT Pub. Date: Jun. 30, 2011

(65) Prior Publication Data
US 2012/0328612 A1    Dec. 27, 2012

Related U.S. Application Data

(60) Provisional application No. 61/289,529, filed on Dec. 23, 2009.

(51) Int. Cl.
| C07K 16/28 | (2006.01) |
| C07K 16/30 | (2006.01) |
| C12N 5/10 | (2006.01) |
| C12N 15/13 | (2006.01) |
| A61K 39/00 | (2006.01) |

(52) U.S. Cl.
CPC ....... *C07K 16/2896* (2013.01); *A61K 2039/505* (2013.01); *C07K 2317/24* (2013.01); *C07K 2317/72* (2013.01); *C07K 2317/34* (2013.01); *C07K 2317/732* (2013.01)

(58) Field of Classification Search
CPC ........... C07K 2317/72; C07K 16/2863; C12N 5/0634; C12N 5/0635
See application file for complete search history.

(56) References Cited

U.S. PATENT DOCUMENTS

| 2005/0054832 A1 | 3/2005 | Lazar et al. |
| 2008/0260731 A1 | 10/2008 | Bernett et al. |
| 2010/0189722 A1* | 7/2010 | Heider et al. ............... 424/172.1 |

FOREIGN PATENT DOCUMENTS

| EP | 2 011 870 | 1/2009 |
| WO | WO 2007041635 A2 * | 4/2007 |
| WO | 2008/137382 | 11/2008 |

OTHER PUBLICATIONS

Hofmann et al., Generation, selection and preclinical characterization of Fc-optimized FLT3 antibody for the treatment of myeloid leukemia, Leukemia, 26:1228-1237, 2012.*

(Continued)

*Primary Examiner* — Claire Kaufman
(74) *Attorney, Agent, or Firm* — Kagan Binder, PLLC

(57) ABSTRACT

The present invention relates to anti-FLT3 antibodies with a modified Fc region comprising the amino acid substitutions 239D and 332E to enhance antibody-dependent cell cytotoxicity (ADCC) of these antibodies. The invention further relates to pharmaceutical compositions containing these antibodies, nucleic acids encoding these antibodies as well as methods of using such antibodies.

20 Claims, 16 Drawing Sheets

(56) References Cited

OTHER PUBLICATIONS

MacCallum et al., Antibody-antigen interactions: contact analysis and binding site topography, J. Mol. Biol. 262:732-745, 1996.*

Lamminmaki et al., Chrystal structure of a recombinant anti-estradiol Fab fragment in complex with the 17beta-estradiol, J. Blol. Chem. 276:36687-94, 2001.*

Rudikoff et al., Single amino acid substitution altering antigen-binding specificity, Proc. Nat. Acad. Sci. USA, 79:1979-1983, Mar. 1982.*

Lazar et al., Engineered antibody Fc variants with enhanced effector function, Proc. Natl. Acad Sci. USA, 103(11):4005-4010, Mar. 14, 2006.*

Stirewalt et al., The role of FLT3 in haematopoietic malignancies, Nat. Rev. Cancer, 3:650-655, Sep. 2003.*

PCT Search Report for International Application No. PCT/EP2010/070659; mailed on Apr. 4, 2011.

Rappold I., et al., (1997) *Functional and Phenotypic Characterization of Cord Blood and Bone Marrow Subsets Expressing FLT3 (CD135) Receptor Tyrosine Kinase*, Blood 90: 111-125.

* cited by examiner

```
              10              20              30              40              50
4g8-vj  D I V L T Q S P A T L S V T P G D S V S L S C R A S Q S I S N H - - - - - L H W Y Q Q K S H S S P   44
bv10-vj D I V M T Q S P S S L S V S A G E K V T M S C K S S Q S L L N S G N Q K N Y M A W Y Q Q K P G Q P P   50
Consensus D I V - T Q S P - - L S V - - G - - V - - S C - - S Q S - - N - - - - - - - - - W Y Q Q K - - - - P   50
              60              70              80              90             100
4g8-vj  R L L I K Y A S Q S I S G I P S R F S G S G S G T D F T L S I N S V E T E D F G V Y F C Q Q S N T W   94
bv10-vj K L L I Y G A S T R E S G V P D R F T G S G S G T D F T L T I S S V Q A E D L A V Y Y C Q N D H S Y  100
Consensus - L L I - - A S - - - S G - P - R F - G S G S G T D F T L - I - S V - - E D - - V Y - C Q - - - - -  100
             110
4g8-vj  P Y T F G G G T K L E I K R   Position 21-128 of SEQ ID NO:23                  108
bv10-vj P L T F G A G T K L E L K R   Position 21-134 of SEQ ID NO:39                  114
Consensus P - T F G - G T K L E - K R   SEQ ID NO:69 or 70                             114
```

B

```
              10              20              30              40              50
4g8-vdj Q V Q L Q Q P G A E L V R P G A S L K L S C K S S G Y T F T S Y W M H W V R Q R P G H G L E W I G E   50
bv10-vdj Q V Q L K Q S G P G L V Q P S Q S L S I T C T V S G F S L T N Y G L H W V R Q S P G K G L E W L G V   50
Consensus Q V Q L - Q - - - L V - P - - S L - - - C - - S G - - - T - Y - - H W V R Q - P G - G L E W - G -   50
              60              70              80              90             100
4g8-vdj T N P S D S Y K D Y N Q K F K D K A T L T V D R S S N T A Y M H L S S L T S D D S A V Y Y C A R - -   98
bv10-vdj I W S G G S - T D Y N A A F I S R L S I S K D N S K S Q V F F K M H S L Q A E D T A I Y Y C A R K G   99
Consensus I - - - - S - - D Y N - - F - - - - - - - - - D - S - - - - - - - - S L - - E D - A - Y Y C A R - -  100
             110             120
4g8-vdj - - - - A I T T T P F D F W G Q G T T L T V S S   Position 20-137 of SEQ ID NO:25  118
bv10-vdj G I Y Y A N H Y Y A M D Y W G Q G T S V T V S S   Position 20-142 of SEQ ID NO:41  123
Consensus - - - - A - - - - - - D - W G Q G T - - T V S S   SEQ ID NO:71 or 72             124
```

ANTI-FLT3 ANTIBODIES

This application claims benefit from International Application No. PCT/EP2010/070659, which was filed on Dec. 23, 2010, which in turn claims priority to U.S. Provisional Patent Application No. 61/289,529, filed on Dec. 23, 2009; wherein the entireties of said patent applications are incorporated herein by reference. Also, the entire contents of the ASCII text file entitled "IPM0031US_Sequence_Listing2_ST25.txt" created on Mar. 19, 2015, having a size of 97 kilobytes is incorporated herein by reference.

FIELD OF THE INVENTION

The present invention lies in the field of antibodies and relates to FLT3 specific antibodies with a modified Fc region to generate or enhance antibody-dependent cell cytotoxicity (ADCC) as well as methods of using such antibodies.

BACKGROUND OF THE INVENTION

The tyrosine kinase receptor FLT3 expressed on the cell surface of hematopoietic progenitor cells plays an important role in early hematopoiesis. Due to its pivotal role in regulating survival, proliferation, and differentiation of hematopoietic cells (B and T cells), aberrant FLT3 activity is involved in the development and progression of cancers of the hematopoietic system. For example, internal tandem duplications of FLT3 are the most common mutations associated with acute myelogenous leukemia (AML). There is thus need in the art for antibodies that can specifically target and destroy FLT3-expressing cells.

Thus, one object of the inventors of the present invention was to provide anti-FLT3 antibodies that can bind to and kill FLT3-expressing cells in vivo.

SUMMARY OF THE INVENTION

The present invention is directed to antibodies directed against human receptor tyrosine kinase FLT3 and methods of using the same. In certain aspects, the antibodies include a variant Fc region. In further embodiments, the antibodies are chimeric or humanized antibodies. The present invention is further directed to pharmaceutical compositions comprising these antibodies and methods of using the antibodies in various disease indications.

In a first aspect, the present invention is directed to an antibody that binds human receptor tyrosine kinase FLT3, wherein said antibody comprises a heavy chain and/or a light chain and has at least one amino acid substitution in the constant region relative to a parent anti-FLT3 antibody, wherein said at least one amino acid substitution includes the amino acid substitutions 239D and 332E, wherein the positional numbering is according to the EU index (Kabat et al., 1983). In one specific embodiment, the substitutions are S239D and I332E.

In one embodiment of the invention, the anti-FLT3 antibody has cell killing activity, such as, for example, antibody-dependent cell-mediated cytotoxicity (ADCC) effector function. That means that upon contact with FLT3-expressing cells, the antibody is capable of facilitating cell death, for example by triggering activation of the complement system, phagocytosis or apoptosis.

In one embodiment, the antibody comprises a heavy and a light chain. The heavy chain may comprise a $V_H$ CDR1, a $V_H$ CDR2, and a $V_H$ CDR3 region and/or the light chain may comprise a $V_L$ CDR1, a $V_L$ CDR2, and/or a $V_L$ CDR3 region.

In one specific embodiment, the $V_L$ CDR1 comprises, consists essentially of or consists of an amino acid sequence selected from the group consisting of the amino acid sequences SEQ ID NO:1 and SEQ ID NO:7; the $V_L$ CDR2 comprises, consists essentially of or consists of an amino acid sequence selected from the group consisting of the amino acid sequences of SEQ ID NO:2 and SEQ ID NO:8; the $V_L$ CDR3 comprises, consists essentially of or consists of an amino acid sequence selected from the group consisting of the amino acid sequences of SEQ ID NO:3 and SEQ ID NO:9; the $V_H$ CDR1 comprises, consists essentially of or consists of an amino acid sequence selected from the group consisting of the amino acid sequences of SEQ ID NO:4 and SEQ ID NO:10; the $V_H$ CDR2 comprises, consists essentially of or consists of an amino acid sequence selected from the group consisting of the amino acid sequences of SEQ ID NO:5 and SEQ ID NO:11; and the $V_H$ CDR3 comprises, consists essentially of or consists of an amino acid sequence selected from the group consisting of the amino acid sequences of SEQ ID NO:6 and SEQ ID NO:12.

In another specific embodiment, the $V_L$ CDR1 comprises, consists essentially of or consists of the amino acid sequence set forth in SEQ ID NO:1; the $V_L$ CDR2 comprises, consists essentially of or consists of the amino acid sequence set forth in SEQ ID NO:2; the $V_L$ CDR3 comprises, consists essentially of or consists of the amino acid sequence set forth in SEQ ID NO:3; the $V_H$ CDR1 comprises, consists essentially of or consists of the amino acid sequence set forth in SEQ ID NO:4; the $V_H$ CDR2 comprises, consists essentially of or consists of the amino acid sequence set forth in SEQ ID NO:5; and the $V_H$ CDR3 comprises, consists essentially of or consists of the amino acid sequence set forth in SEQ ID NO:6.

In still another specific embodiment, the $V_L$ CDR1 comprises, consists essentially of or consists of the amino acid sequence set forth in SEQ ID NO:7; the $V_L$ CDR2 comprises, consists essentially of or consists of the amino acid sequence set forth in SEQ ID NO:8; the $V_L$ CDR3 comprises, consists essentially of or consists of the amino acid sequence set forth in SEQ ID NO:9; the $V_H$ CDR1 comprises, consists essentially of or consists of the amino acid sequence set forth in SEQ ID NO:10; the $V_H$ CDR2 comprises, consists essentially of or consists of the amino acid sequence set forth in SEQ ID NO:11; and the $V_H$ CDR3 comprises, consists essentially of or consists of the amino acid sequence set forth in SEQ ID NO:12.

In one embodiment of the invention, the heavy chain of the invented antibody comprises a $V_H$ domain comprising, consisting essentially of or consisting of the amino acid sequence set forth in SEQ ID NO:14 and/or the light chain of the invented antibody comprises a $V_L$ domain comprising, consisting essentially of or consisting of the amino acid sequence set forth in SEQ ID NO:13.

In another embodiment of the invention, the heavy chain of the invented antibody comprises a $V_H$ domain comprising, consisting essentially of or consisting of the amino acid sequence set forth in SEQ ID NO:30 and/or the light chain of the invented antibody comprises a $V_L$ domain comprising, consisting essentially of or consisting of the amino acid sequence set forth in SEQ ID NO:29.

In another embodiment of the invention, the claimed antibody is a chimeric antibody and comprises a heavy chain having the amino acid sequence set forth in SEQ ID NO:27 and/or a light chain having the amino acid sequence set forth in SEQ ID NO:23.

In another embodiment of the invention, the claimed antibody is a chimeric antibody and comprises a heavy chain having the amino acid sequence set forth in SEQ ID NO:43 and/or a light chain having the amino acid sequence set forth in SEQ ID NO:39.

In certain embodiments of the invention, the antibody of the invention comprising amino acid substitutions S239D/I332E binds with enhanced affinity to the FcγRIIIa receptor or has enhanced ADCC effector function as compared to the parent antibody without said substitution. In this connection, the term "enhanced" includes scenarios where the parent antibody does not show any experimentally verifable ADCC effector function so that the newly generated Fc-optimized antibody exhibits, for the first time and in contrast to the parent antibody from which it may be derived, ADCC effector function.

In further embodiments, the antibody comprises one or more further amino acid modifications at a position selected from the group consisting of 221, 222, 223, 224, 225, 227, 228, 230, 231, 232, 233, 234, 235, 236, 237, 238, 240, 241, 243, 244, 245, 246, 247, 249, 255, 258, 260, 262, 263, 264, 265, 266, 267, 268, 269, 270, 271, 272, 273, 274, 275, 276, 278, 280, 281, 282, 283, 284, 285, 286, 288, 290, 291, 292, 293, 294, 295, 296, 297, 298, 299, 300, 301, 302, 303, 304, 305, 313, 317, 318, 320, 322, 323, 324, 325, 326, 327, 328, 329, 330, 331, 333, 334, 335, 336, and 337, wherein the positional numbering is according to the EU index. These one or more further amino acid modifications may be selected from the group of amino acid substitutions consisting of 221K, 221Y, 222E, 222Y, 223E, 223K, 224E, 224Y, 225E, 225K, 225W, 227E, 227G, 227K, 227Y, 228E, 228G, 228K, 228Y, 230A, 230E, 230G, 230Y, 231E, 231G, 231K, 231P, 231Y, 232E, 232G, 232K, 232Y, 233A, 233D, 233F, 233G, 233H, 233I, 233K, 233L, 233M, 233N, 233Q, 233R, 233S, 233T, 233V, 233W, 233Y, 234A, 34D, 234E, 234F, 234G, 234H, 234I, 234K, 234M, 234N, 234P, 234Q, 234R, 234S, 234T, 234V, 234W, 234Y, 235A, 235D, 235E, 235F, 235G, 235H, 235I, 235K, 235M, 235N, 235P, 235Q, 235R, 235S, 235T, 235V, 235W, 235Y, 236A, 236D, 236E, 236F, 236H, 236I, 236K, 236L, 236M, 236N, 236P, 236Q, 236R, 236S, 236T, 236V, 236W, 236Y, 237D, 237E, 237F, 237H, 237I, 237K, 237L, 237M, 237N, 237P, 237Q, 237R, 237S, 237T, 237V, 237W, 237Y, 238D, 238E, 238F, 238G, 238H, 238I, 238K, 238L, 238M, 238N, 238Q, 238R, 238S, 238T, 238V, 238W, 238Y, 240A, 240I, 240M, 240T, 241D, 241E, 241L, 241R, 241S, 241W, 241Y, 243E, 243H, 243L, 243Q, 243R, 243W, 243Y, 244H, 245A, 246D, 246E, 246H, 246Y, 247O, 247V, 249H, 249Q, 249Y, 255E, 255Y, 258H, 258S, 258Y, 260D, 260E, 260H, 260Y, 262A, 262E, 262F, 262I, 262T, 263A, 263I, 263M, 263T, 264A, 264D, 264E, 264F, 264G, 264H, 264I, 264K, 264L, 264M, 264N, 264P, 264Q, 264R, 264S, 264T, 264W, 264Y, 265F, 265G, 265H, 265I, 265K, 265L, 265M, 265N, 265P, 265Q, 265R, 265S, 265T, 265V, 265W, 265Y, 266A, 266I, 266M, 266T, 267D, 267E, 267F, 267H, 267I, 267K, 267L, 267M, 267N, 267P, 267Q, 267R, 267T, 267V, 267W, 267Y, 268D, 268E, 268F, 268G, 268I, 268K, 268L, 268M, 268P, 268Q, 268R, 268T, 268V, 268W, 269F, 269G, 269H, 269I, 269K, 269L, 269M, 269N, 269P, 269R, 269S, 269T, 269V, 269W, 269Y, 270F, 270G, 270H, 270I, 270L, 270M, 270P, 270Q, 270R, 270S, 270T, 270W, 270Y, 271A, 271D, 271E, 271F, 271G, 271H, 271I, 271K, 271L, 271M, 271N, 271Q, 271R, 271S, 271T, 271V, 271W, 271Y, 272D, 272F, 272G, 272H, 272I, 272K, 272L, 272M, 272P, 272R, 272S, 272T, 272V, 272W, 272Y, 273I, 274D, 274E, 274F, 274G, 274H, 274I, 274L, 274M, 274N, 274Q, 274R, 274T, 274V, 274W, 274Y, 275L, 275W, 276D, 276E, 276F, 276G, 276I, 276L, 276M, 276P, 276R, 276S, 276T, 276V, 276W, 276Y, 278D, 278E, 278G, 278H, 278I, 278K, 278L, 278M, 278N, 278P, 278Q, 278R, 278S, 278T, 278V, 278W, 280G, 280K, 280L, 280P, 280W, 281D, 281E, 281K, 281N, 281P, 281Q, 281Y, 282E, 282G, 282K, 282P, 282Y, 283G, 283H, 283K, 283L, 283P, 283R, 283Y, 284D, 284E, 284L, 284N, 284Q, 284T, 284Y, 285D, 285E, 285K, 285Q, 285W, 285Y, 286E, 286G, 286P, 286Y, 288D, 288E, 288Y, 290D, 290H, 290L, 290N, 290W, 291D, 291E, 291G, 291H, 291I, 291Q, 291T, 292D, 292E, 292T, 292Y, 293F, 293G, 293H, 293I, 293L, 293M, 293N, 293P, 293R, 293S, 293T, 293V, 293W, 293Y, 294F, 294G, 294H, 294I, 294K, 294L, 294M, 294P, 294R, 294S, 294T, 294V, 294W, 294Y, 295D, 295E, 295F, 295G, 295H, 295I, 295M, 295N, 295P, 295R, 295S, 295T, 295V, 295W, 295Y, 296A, 296D, 296E, 296G, 296H, 296I, 296K, 296L, 296M, 296N, 296Q, 296R, 296S, 296T, 296V, 297D, 297E, 297F, 297G, 297H, 297I, 297K, 297L, 297M, 297P, 297Q, 297R, 297S, 297T, 297V, 297W, 297Y, 298A, 298D, 298E, 298F, 298H, 298I, 298K, 298M, 298N, 298Q, 298R, 298T, 298W, 298Y, 299A, 299D, 299E, 299F, 299G, 299H, 299I, 299K, 299L, 299M, 299N, 299P, 299Q, 299R, 299S, 299V, 299W, 299Y, 300A, 300D, 300E, 300G, 300H, 300K, 300M, 300N, 300P, 300Q, 300R, 300S, 300T, 300V, 300W, 301D, 301E, 301H, 301Y, 302I, 303D, 303E, 303Y, 304D, 304H, 304L, 304N, 304T, 305E, 305T, 305Y, 313F, 317E, 317Q, 318H, 318L, 318Q, 318R, 318Y, 320D, 320F, 320G, 320H, 320I, 320L, 320N, 320P, 320S, 320T, 320V, 320W, 320Y, 322D, 322F, 322G, 322H, 322I, 322P, 322S, 322T, 322V, 322W, 322Y, 323I, 324D, 324F, 324G, 324H, 324I, 324L, 324M, 324P, 324R, 324T, 324V, 324W, 324Y, 325A, 325D, 325E, 325F, 325G, 325H, 325I, 325K, 325L, 325M, 325P, 325Q, 325R, 325S, 325T, 325V, 325W, 325Y, 326E, 326I, 326L, 326P, 326T, 327D, 327E, 327F, 327H, 327I, 327K, 327L, 327M, 327N, 327P, 327R, 327S, 327T, 327V, 327W, 327Y, 328A, 328D, 328E, 328F, 328G, 328H, 328I, 328K, 328M, 328N, 328P, 328Q, 328R, 328S, 328T, 328V, 328W, 328Y, 329D, 329E, 329F, 329G, 329H, 329I, 329K, 329L, 329M, 329N, 329Q, 329R, 329S, 329T, 329V, 329W, 329Y, 330E, 330F, 330G, 330H, 330I, 330L, 330M, 330N, 330P, 330R, 330S, 330T, 330V, 330W, 330Y, 331D, 331F, 331H, 331I, 331L, 331M, 331Q, 331R, 331T, 331V, 331W, 331Y, 333A, 333F, 333H, 333I, 333L, 333M, 333P, 333T, 333Y, 334A, 334F, 334I, 334L, 334P, 334T, 335D, 335F, 335G, 335H, 335I, 335L, 335M, 335N, 335P, 335R, 335S, 335V, 335W, 335Y, 336E, 336K, 336Y, 337E, 337H, and 337N, wherein the positional numbering is according to the EU index.

In another embodiment, the one or more further amino acid modifications are at a position selected from the group consisting of 221, 222, 223, 224, 225, 228, 230, 231, 232, 240, 244, 245, 247, 262, 263, 266, 271, 273, 275, 281, 284, 291, 299, 302, 304, 313, 323, 325, 328, and 336, wherein the positional numbering is according to the EU index. In such an embodiment, the one or more further amino acid modifications may be selected from the group of amino acid substitutions consisting of 221K, 221Y, 222E, 222Y, 223E, 223K, 224E, 224Y, 225E, 225K, 225W, 228E, 228O, 228K, 228Y, 230A, 230E, 230G, 230Y, 231E, 231G, 231K, 231P, 231Y, 232E, 232G, 232K, 232Y, 240A, 240I, 240M, 240T, 244H, 245A, 247G, 247V, 262A, 262E, 262F, 262I, 262T, 263A, 263I, 263M, 263T, 266A, 266I, 266M, 266T, 271A, 271D, 271E, 271F, 271G, 271H, 271I, 271K, 271L, 271M, 271N, 271Q, 271R, 271S, 271T, 271V, 271W, 271Y, 273I, 275L, 275W, 281D, 281E, 281K, 281N, 281P, 281Q, 281Y, 284D, 284E, 284L, 284N, 284Q, 284T, 284Y, 291D, 291E, 291G, 291H, 291I, 291Q, 291T, 299A, 299D, 299E, 299F, 299G, 299H, 299I, 299K, 299L, 299M, 299N, 299P, 299Q, 299R, 299S, 299V, 299W, 299Y, 304D, 304H, 304L, 304N, 304T, 313F, 323I, 325A, 325D, 325E, 325F, 325G, 325H, 325I, 325K, 325L, 325M, 325P, 325Q, 325R, 325S, 325T, 325V, 325W, 325Y, 328A, 328D, 328E, 328F, 328G, 328H, 328I, 328K, 328M, 328N, 328P, 328Q, 328R, 328S, 328T, 328V, 328W, 328Y, 336E, 336K, and 336Y.

In a specific embodiment, the antibody comprises one or more further amino acid modifications selected from the group consisting of: 236A, 268D, 268E, 330Y, and 330L.

In another aspect, the present invention features nucleic acid molecules that encode the heavy chain and/or the light chain of an antibody of the invention. These nucleic acid molecules may comprise a nucleotide sequence that encodes the variable domain of the light chain, such as that set forth in SEQ ID NO: 17 or SEQ ID NO:33, or a nucleotide sequence that encodes the variable domain of the heavy chain, such as that set forth in SEQ ID NO: 18 or SEQ ID NO:34.

In one specific embodiment, the nucleic acid encoding the light chain of the antibody of the invention has a nucleotide sequence selected from the group consisting of SEQ ID Nos. 24 and 40.

In another specific embodiment, the nucleic acid encoding the heavy chain of the antibody of the invention has a nucleotide sequence selected from the group consisting of SEQ ID Nos. 28 and 44.

In a further aspect, the present invention relates to a method of treating a human receptor tyrosine kinase FLT3 related disease or disorder, wherein said method includes administering the antibody of the invention to a subject in need thereof. The subject may, for example, be an animal or human, preferably a mammal, such as a human.

In one embodiment, said disease or disorder is a cell proliferative disease or disorder.

In another embodiment, the disease or disorder is a tumor of hematopoietic origin, such as a lymphoma or leukemia. The lymphoma or leukemia may be selected from the group consisting of: non-Hodgkin's lymphomas (NHL), chronic lymphocytic leukemia (CLL), B-cell acute lymphoblastic leukemia/lymphoma (B-ALL), mantle cell lymphoma (MCL), hairy cell leukemia (HCL), chronic myeloid leukemia (CML), acute myeloid leukemia, and multiple myeloma (MM). In a preferred embodiment, the lymphoma is acute myeloid leukemia (AML).

In another embodiment, the disease or disorder is myelodysplastic syndrome (MDS).

In various embodiments, the lymphoma or leukemia is in the stage of minimal residual disease (MRD), for example reached after conventional chemotherapy with or without stem cell transplantation.

In certain embodiments of the invented methods, the antibody may be administered in combination with at least one agent selected from the group consisting of a cytotoxic agent, a chemotherapeutic agent, a cytokine, a growth inhibitory agent, an anti-hormonal agent, a kinase inhibitor, an antiangiogenic agent, a cardioprotectant, an immunostimulatory agent, an immunosuppressive agent, an angiogenesis inhibitor, a protein tyrosine kinase inhibitor, and second antibody.

In a still further aspect, the present invention also encompasses a pharmaceutical composition comprising an antibody according to the invention and a pharmaceutically acceptable carrier.

In another aspect, the present invention is directed to a method of inhibiting proliferation of a cell expressing FLT3, wherein said method comprises contacting said cell with an antibody according to the invention. The method may be an in vitro method.

In a further aspect, the present invention relates to a method of enhancing antibody-dependent cell-mediated cytotoxicity toward a cell expressing FLT3, wherein said method comprises contacting said cell with an antibody according to the invention.

A still further aspect of the invention is a method of depleting a mammal of at least one cell expressing FLT3, wherein said method comprises administering to the mammal an antibody according to the invention.

The present invention also relates to the use of an antibody according to the present invention for treating an FLT3-related disease or disorder. The FLT3-related disease or disorder may be a cell proliferative disease or disorder, such as a tumor of hematopoietic origin, for example a lymphoma or leukemia, or myelodysplastic syndrome (MDS). The lymphoma or leukemia may be selected from the group consisting of: non-Hodgkin's lymphomas (NHL), chronic lymphocytic leukemia (CLL), B-cell acute lymphoblastic leukemia/lymphoma (B-ALL), mantle cell lymphoma (MCL), hairy cell leukemia (HCL), chronic myeloid leukemia (CML), acute myeloid leukemia (AML), and multiple myeloma (MM) and preferably is acute myeloid leukemia.

In another embodiment, the invention relates to the use of an antibody according to the invention for the targeting of a cell expressing FLT3. The targeting may include the use of the antibody to deliver a drug or a toxin to the FLT3-expressing cell.

In a still further aspect, the invention encompasses the use of an antibody according to the invention for the detection of a cell expressing FLT3 in a biological sample. For such use, the antibody may be labeled with a detectable moiety, such as a fluorophore, chromophore, immunogenic tag and the like.

The present invention is also directed to a monoclonal antibody against FLT3, wherein the antibody is produced by a transfected producer cell line, such as CHO or Sp2/0.

In a still further aspect, the invention features a transfected cell line producing an antibody according to the invention.

BRIEF DESCRIPTION OF THE DRAWINGS

The invention will be better understood with reference to the detailed description when considered in conjunction with the non-limiting examples and the accompanying drawings.

FIG. 3B shows the sequence context generated upon insertion of the VDJ region of the heavy chain of monoclonal antibodies BV10 or 4G8 into the heavy chain expression vector chimFLT3-heavy. The cleavage site for secretory signal peptides is indicated by |; and exon-intron boundaries by [,].

FIG. 4 C shows the cell killing effects of chimeric antibodies directed to NG2 that have been Fc optimized in the same positions as the above antibodies chim4G8-SDIE and chimBV10-SDIE on human SKMel63-melanoma cells. Cytotoxicity was determined using a chromium release assay, duration of the assay and target:effector ratios are indicated.

FIG. 6 shows an amino acid sequence alignment of the light (A) and heavy (B) chain variable regions of the anti-FLT3 antibody clones 4G8 and BV10.

DETAILED DESCRIPTION OF THE INVENTION

Figure 1:
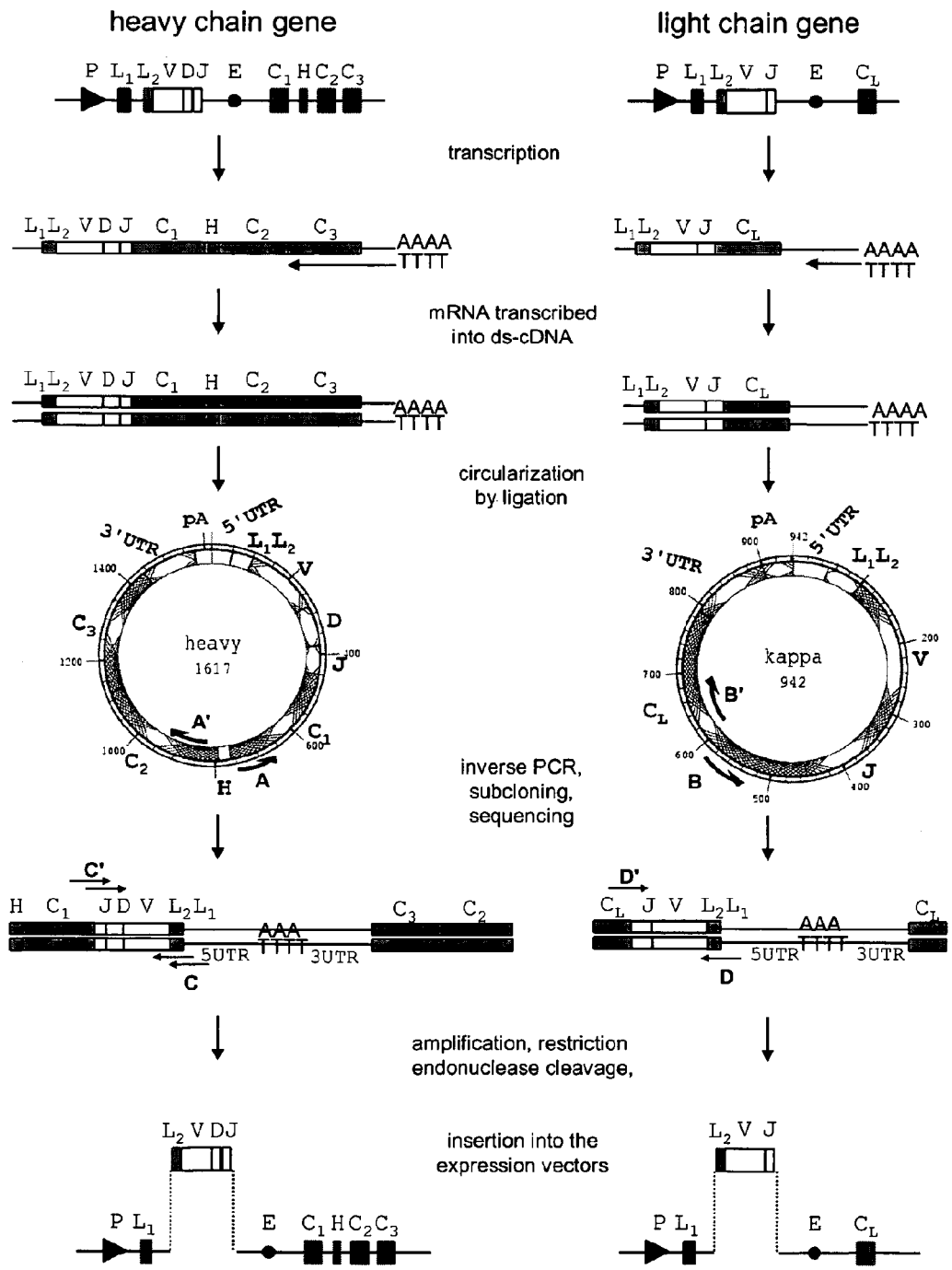
FIG. 1 shows a schematic representation of the cloning procedure for chimerization of monoclonal antibodies. Boxes represent exons, circle indicate enhancer elements and thin lines UT regions and intron sequences. P, promoter; $L_1$ and $L_2$, leader sequences encoded by two different exons; E, enhancer; V, variable region; D, diversity region; J, joing region; $C_{(1-3)}$ exons of constant region; H, hinge region.

The terms used herein have, unless explicitly stated otherwise, the following meanings.

By "ADCC" or "antibody dependent cell-mediated cytotoxicity" as used herein is meant the cell mediated reaction wherein cytotoxic cells that express FcγRs recognize bound antibody on a target cell and subsequently cause lysis of the target cell By "ADCP" or "antibody dependent cell-mediated phagocytosis" as used herein is meant the cell-mediated reaction wherein nonspecific cytotoxic cells that express FcγRs recognize bound antibody on a target cell and subsequently cause phagocytosis of the target cell.

By "amino acid" and "amino acid identity" as used herein is meant one of the 20 naturally occurring amino acids or any non-natural analogues that may be present at a specific, defined position. Thus "amino acid" as used herein is both naturally occurring and synthetic amino acids. For example, homophenylalanine, citrulline and noreleucine are considered amino acids for the purposes of the invention. "Amino acid" also includes imino acid residues such as proline and hydroxyproline. The side chain may be in either the (R) or the (S) configuration. In a embodiment, the amino acids are in the (S) or L-configuration. If non-naturally occurring side chains are used, non-amino acid substituents may be used, for example to prevent or retard in vivo degradation.

By "antibody" herein is meant a protein consisting of one or more polypeptides substantially encoded by all or part of the recognized immunoglobulin genes. The recognized immunoglobulin genes, for example in humans, include the kappa (κ), lambda (λ), and heavy chain genetic loci, which together comprise the myriad variable region genes, and the constant region genes mu (µ), delta (δ), gamma (γ), epsilon (ε), and alpha (α) which encode the IgM, IgD, IgG (IgG1, IgG2, IgG3, and IgG4), IgE, and IgA (IgA1 and IgA2) isotypes respectively. Antibody herein is meant to include full length antibodies and antibody fragments, and may refer to a natural antibody from any organism, an engineered antibody, or an antibody generated recombinantly for experimental, therapeutic, or other purposes.

By "B cell" or "B lymphocyte" as used herein is meant a type of lymphocyte developed in bone marrow that circulates in the blood and lymph, and provides humoral immunity. B cells recognize free antigen molecules and differentiate or mature into plasma cells that secrete immunoglobulin (antibodies) that inactivate the antigens. Memory cells are also generated that make the specific immunoglobulin (antibody) on subsequent encounters with such antigen. B cells are also known as "Beta cells" in the islet of Langerhans.

By "T cell" or "T lymphocyte" as used herein is meant a type of lymphocyte developed in bone marrow that circulates in the blood and the lymph, and provides cellular immunity. T cells comprise a T cell receptor that recognizes cell-bound antigen molecules. T cells can mature into helper T cells that secrete cytokines and activate other cell types or cytotoxic T cells that bind to and destroy other cells.

By "FLT3" (fms-like tyrosine kinase receptor-3), "FLK2" (fetal liver kinase-2), and "CD135" as used interchangeably herein is meant a cytokine receptor expressed on the surface of hematopoietic progenitor cells. FLT3 is a cell surface marker used to identify certain types of hematopoietic (blood) progenitors in the bone marrow. Specifically, multipotent progenitors (MPP) and common lymphoid progenitors (CLP) express high surface levels of FLT3. The FLT3 receptor is bound by the cytokine Flt3 ligand (Flt3L). FLT3 is a receptor tyrosine kinase type III. When this receptor is bound by Flt3L it forms a dimer (homodimer) which activates second messenger signaling. FLT3 signaling plays an important role in cell survival, proliferation, and differentiation of lymphocytes (B cell and T cell) development. As deregulation of FLT3 signaling can cause proliferative diseases, such as cancer, and in particular leukemia, FLT3 is classified as a proto-oncogene. In fact, internal tandem duplications of FLT3 are the most common mutations associated with acute myelogenous leukemia (AML). The use of FLT3 herein is meant to encompass all known or as yet undiscovered alleles and polymorphic forms of FLT3. The sequence of human FLT3 antigen is provided in SEQ ID NO:65.

By "CDC" or "complement dependent cytotoxicity" as used herein is meant the reaction wherein one or more complement protein components recognize bound antibody on a target cell and subsequently cause lysis of the target cell.

By "constant region" of an antibody as defined herein is meant the region of the antibody that is encoded by one of the light or heavy chain immunoglobulin constant region genes.

By "constant light chain" or "light chain constant region" as used herein is meant the region of an antibody encoded by the kappa ($C_\kappa$) or lambda ($C_\lambda$) light chains The constant light chain typically comprises a single domain, and as defined herein refers to positions 108-214 of $C_\kappa$ or lambda $C_\lambda$, wherein numbering is according to the EU index.

By "constant heavy chain" or "heavy chain constant region" as used herein is meant the region of an antibody encoded by the mu, delta, gamma, alpha, or epsilon genes to define the antibody's isotype as IgM, IgD, IgG, IgA, or IgE, respectively For full length IgG antibodies, the constant heavy chain, as defined herein, refers to the N-terminus of the CH1 domain to the C-terminus of the CH3 domain, thus comprising positions 118-447, wherein numbering is according to the EU index.

By "effector function" as used herein is meant a biochemical event that results from the interaction of an antibody Fc region with an Fc receptor or ligand. Effector functions include FcγR-mediated effector functions such as ADCC and ADCP, and complement-mediated effector functions such as CDC.

By "effector cell" as used herein is meant a cell of the immune system that expresses one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and T cells and may be from any organism including but not limited to humans, mice, rats rabbits, and monkeys.

By "Fab" or "Fab region" as used herein is meant the polypeptides that comprise the VH, CH1, VH, and CL immunoglobulin domains. Fab may refer to this region in isolation, or this region in the context of a full length antibody or antibody fragment.

By "Fc" or "Fc region", as used herein is meant the polypeptide comprising the constant region of an antibody excluding the first constant region immunoglobulin domain Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains $C_{\gamma 2}$ and $C_{\gamma 3}$ and the hinge between $C_{\gamma 1}$ and $C_{\gamma 2}$. Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an Fc polypeptide, for example an antibody.

By "Fc polypeptide" as used herein is meant a polypeptide that comprises all or part of an Fc region Fc polypeptides include antibodies Fc fusions, isolated Fcs, and Fc fragments.

By "Fc gamma receptor" or "FcγR" as used herein is meant any member of the family of proteins that bind the IgG antibody Fc region and are substantially encoded by the FcγR genes. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD 16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65), as well as any undiscovered human FcγRs or FcγR isoforms or allotypes. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes. An FcγR may be from any organism, including but not limited to humans, mice, rats, rabbits, and monkeys.

By "Fc ligand" or "Fc receptor" as used herein is meant a molecule, e.g., a polypeptide, from any organism that binds to the Fc region of an antibody to form an Fc-ligand complex. Fc ligands include but are not limited to FcγRs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., 2002, Immunological Reviews 190:123-136). Fc ligands may include undiscovered molecules that bind Fc.

By "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3.

By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full length antibodies, antibody fragments, and individual immunoglobulin domains.

By "immunoglobulin (Ig) domain" herein is meant a region of an immunoglobulin that exists as a distinct structural entity as ascertained by one skilled in the art of protein structure. Ig domains typically have a characteristic β-sandwich folding topology. The known Ig domains in the IgG class of antibodies are VH, Cγ1, Cγ2, Cγ3, VL, and CL.

By "amino acid modification" herein is meant an amino acid substitution, insertion, and/or deletion in a polypeptide sequence.

By "amino acid substitution" or "substitution" herein is meant the replacement of an amino acid at a particular position in a parent polypeptide sequence with another amino acid For example, the substitution I332E refers to a variant polypeptide, in this case a constant heavy chain variant, in which the isoleucine at position 332 is replaced with glutamic acid The wildtype residue may or may not be designated. For the preceding example, 332E indicates the substitution of position 332 with a glutamic acid. For the purposes herein, multiple substitutions are typically separated by a slash. For example, 239D/332E refers to a double variant comprising the substitutions 239D and 332E.

By "amino acid insertion" or "insertion" as used herein is meant the addition of an amino acid at a particular position in a parent polypeptide sequence. For example, insert −236G designates an insertion of glycine at position 236.

By "amino acid deletion" or "deletion" as used herein is meant the removal of an amino acid at a particular position in a parent polypeptide sequence For example, G236− designates the deletion of glycine at position 236.

By "parent polypeptide", "parent protein", "precursor polypeptide", or "precursor protein" as interchangeably used herein is meant a polypeptide that is subsequently modified to generate a variant, e g., any polypeptide which serves as a template and/or basis for at least one amino acid modification described herein. The parent polypeptide may be a naturally occurring polypeptide, or a variant or engineered version of a naturally occurring polypeptide Parent polypeptide may refer to the polypeptide itself, compositions that comprise the parent polypeptide, or the amino acid sequence that encodes it. Accordingly, by "parent antibody" or "parent immunoglobulin" as used herein is meant an antibody or immunoglobulin that is modified to generate a variant (e.g., a parent antibody may include, but is not limited to, a protein comprising the constant region of a naturally occurring Ig).

By "protein" or "polypeptide" as used herein is meant at least two covalently attached amino acids, which includes proteins, polypeptides, oligopeptides and peptides The protein may be made up of naturally occurring amino acids and peptide bonds, or synthetic peptidomimetic structures, i.e. "analogs", such as peptoids.

By "position" as used herein is meant a location in the sequence of a protein. Positions may be numbered sequentially, or according to an established format, for example the EU index as in Kabat (Kabat et al., 1983). If not indicated otherwise, all positions mentioned herein are numbered according to the EU index. Corresponding positions are determined as outlined herein, generally through alignment with other parent sequences.

By "residue" as used herein is meant a position in a protein and its associated amino acid identity For example, Serine 239 (also referred to as Ser239 and S239) is a residue at position 239 in the human antibody IgG1.

By "target antigen" or "target" or "antigen" as used herein is meant the molecule that is bound specifically by the variable region of a given antibody. A target antigen may be a protein, carbohydrate, lipid, or other chemical compound.

By "target cell" as used herein is meant a cell that expresses a target antigen.

By "variable region" as used herein is meant the region of an immunoglobulin that comprises one or more Ig domains substantially encoded by any of the Vκ, Vλ, and/or VH genes that make up the kappa, lambda, and heavy chain immunoglobulin genetic loci respectively.

By "variant protein", "protein variant", "variant polypeptide", or "polypeptide variant" as used herein is meant a polypeptide sequence that differs from that of a parent polypeptide sequence by virtue of at least one amino acid modification. Variant polypeptide may refer to the polypeptide itself, a composition comprising the polypeptide, or the amino sequence that encodes it. In one embodiment, the variant polypeptide has at least one amino acid modification compared to the parent polypeptide, e g from about one to about ten amino acid modifications, e.g., from about one to about five amino acid modifications compared to the parent. The variant polypeptide sequence herein may possess at least about 80% homology with a parent polypeptide sequence, e g, at least about 90% homology, at least about 95% homology, etc. Accordingly, by "variant antibody" or "antibody variant" as used herein is meant an antibody sequence that differs from that of a parent antibody sequence by virtue of at least one amino acid modification. Variant antibody or antibody variant may refer to the antibody polypeptide itself, compositions comprising the antibody variant polypeptide, or the amino acid sequence that encodes it. Accordingly, by "constant heavy chain variant" or "constant light chain variant" or "Fc variant" as used herein is meant a constant heavy chain, constant light chain, or Fc region polypeptide or sequence, respectively, that differs in sequence from that of a parent sequence by virtue of at least one amino acid modification.

By "wild type" or "WT" herein is meant an amino acid sequence or a nucleotide sequence that is found in nature, including allelic variations. A WT protein, polypeptide, antibody, immunoglobulin, IgG, etc., has an amino acid sequence or a nucleotide sequence that has not been intentionally modified.

For all immunoglobulin heavy chain constant region positions discussed in the present invention, numbering is according to the EU index as in Kabat (Kabat et al., 1991, Sequences of Proteins of Immunological Interest, 5th Ed, United States Public Health Service, National Institutes of Health, Bethesda). The "EU index as in Kabat" refers to the residue numbering of the human IgG1 EU antibody, as described in Edelman et al., 1969, Biochemistry 63 78-85).

"Antigens" are macromolecules capable of generating an antibody response in an animal and being recognized by the resulting antibody. Both antigens and haptens comprise at least one antigenic determinant or "epitope", which is the region of the antigen or hapten which binds to the antibody. Typically, the epitope on a hapten is the entire molecule.

The term "sample", as used herein, refers to an aliquot of material, frequently biological matrices, an aqueous solution or an aqueous suspension derived from biological material. Samples to be assayed for the presence of an analyte by the methods of the present invention include, for example, cells, tissues, homogenates, lysates, extracts, and purified or partially purified proteins and other biological molecules and mixtures thereof.

Non-limiting examples of samples typically used in the methods of the invention include human and animal body fluids such as whole blood, serum, plasma, cerebrospinal fluid, sputum, bronchial washing, bronchial aspirates, urine, semen, lymph fluids and various external secretions of the respiratory, intestinal and genitourinary tracts, tears, saliva, milk, white blood cells, myelomas and the like; biological fluids such as cell culture supernatants; tissue specimens which may or may not be fixed; and cell specimens which may or may not be fixed. The samples used in the methods of the present invention will vary based on the assay format and the nature of the tissues, cells, extracts or other materials, especially biological materials, to be assayed. Methods for preparing protein extracts from cells or samples are well known in the art and can be readily adapted in order to obtain a sample that is compatible with the methods of the invention.

"Specifically binding" and "specific binding", as used herein, mean that an antibody binds to its target (analyte) based on recognition of an epitope on the target molecule. The antibody preferably recognizes and binds to the target molecule with a higher binding affinity than it binds to other compounds that may be present. In various embodiments of the invention, "specifically binding" may mean that an antibody binds to a target molecule with at least about a $10^6$-fold greater affinity, preferably at least about a $10^7$-fold greater affinity, more preferably at least about a $10^8$-fold greater affinity, and most preferably at least about a $10^9$-fold greater affinity than it binds molecules unrelated to the target molecule. Typically, specific binding refers to affinities in the range of about $10^6$-fold to about $10^9$-fold greater than non-specific binding. In some embodiments, specific binding may be characterized by affinities greater than $10^9$-fold over non-specific binding. The binding affinity may be determined by any suitable method. Such methods are known in the art and include, without limitation, surface plasmon resonance and isothermal titration calorimetry. In a specific embodiment, the antibody uniquely recognizes and binds to the target analyte.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they may be synthesized by hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. The monoclonal antibodies can include "chimeric" antibodies (U.S. Pat. No. 4,816,567; and Morrison et al. (1984) Proc. Natl. Acad. Sci. USA, 81: 6851-6855) and humanized antibodies (Jones et al. (1986) Nature, 321: 522-525; Reichmann et al. (1988) Nature, 332: 323-329; Presta (1992) Curr. Op. Struct. Biol. 2: 593-596).

Monoclonal antibodies may be obtained by any technique that provides for the production of antibody molecules by continuous cell lines in culture. These include, but are not limited to the hybridoma technique of Koehler and Milstein (1975), Nature, 256: 495-7; and U.S. Pat. No. 4,376,110), the human B-cell hybridoma technique (Kosbor, et al. (1983), Immunology Today, 4: 72; Cote, et al. (1983), Proc. Natl. Acad. Sci. USA, 80: 2026-30), and the EBV-hybridoma technique (Cole, et al. (1985), in Monoclonal Antibodies And Cancer Therapy, Alan R. Liss, Inc., New York, pp. 77-96). The preparation of monoclonal antibodies specific for a target compound is also described in Harlow and Lane, eds. (1988) Antibodies—A Laboratory Manual. Cold Spring Harbor Laboratory, Chapter 6. Such antibodies may be of any immunoglobulin class including IgG, IgM, IgE, IgA, IgD and any subclass thereof. The hybridoma producing the mAb may be cultivated in vitro or in vivo. Production of high titers of mAbs in vivo makes this a very effective method of production.

"Polyclonal antibodies" are heterogeneous populations of antibody molecules derived from the sera of animals immunized with an antigen, or an antigenic functional derivative thereof. For the production of polyclonal antibodies, host animals such as rabbits, mice and goats, may be immunized by injection with an antigen or hapten-carrier conjugate optionally supplemented with adjuvants.

Techniques described for the production of single chain antibodies (U.S. Pat. No. 4,946,778; Bird (1988), Science 242: 423-26; Huston, et al. (1988), Proc. Natl. Acad. Sci. USA, 85: 5879-83; and Ward, et al. (1989), Nature, 334: 544-46) can be adapted to produce gene-single chain antibodies. Single chain antibodies are typically formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')$_2$ fragments that can be produced by pepsin digestion of the antibody molecule and the Fab fragments that can be generated by reducing the disulfide bridges of the F(ab')$_2$ fragments. Alternatively, Fab expression libraries may be constructed (Huse, et al. (1989), Science, 246: 1275-1281) to allow rapid and easy identification of monoclonal Fab fragments with the desired specificity.

The terms "polynucleotide" and "nucleic acid (molecule)" are used interchangeably herein to refer to polymeric forms of nucleotides of any length, including naturally occurring and non-naturally occurring nucleic acids. The polynucleotides may contain deoxyribonucleotides, ribonucleotides and/or their analogs. Methods for selection and preparation of nucleic acids are diverse and well described in standard biomolecular protocols. A typical way would be preparative PCR and chromatographic purification starting from existing template DNAs or stepwise synthesis of artificial nucleic acids. Typically, the nucleic acid molecules referred to herein are DNA molecules.

The term "at least one" as used herein in connection with amino acid substitutions relates to at least 1, but preferably at least 2, 3, 4, 5, 6, 7, 8, 9, 10, 11, 12, 13, 14, 15, 20, 25, 30, 35, 40, 45, 50 or a plurality of amino acid substitutions.

The terms "contacting" or "incubating", as used interchangeably herein, refer generally to providing access of one component, reagent, analyte or sample to another.

The term "detecting" as used herein refers to any method of verifying the presence of a given molecule. The techniques used to accomplish this may include, but are not limited to, immunoassays, such as ELISA and Immuno PCR (IPCR).

Hematological malignancies are cancer types of cancer that affect blood, bone marrow, and lymph nodes. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin.

Leukemia is a cancer of the blood or bone marrow and is characterized by an abnormal proliferation of blood cells, usually white blood cells (leukocytes). Leukemia is clinically and pathologically subdivided into a variety of large groups. Acute leukemia is characterized by the rapid increase of immature blood cells. This crowding makes the bone marrow unable to produce healthy blood cells. Immediate treatment is required in acute leukemia due to the rapid progression and accumulation of the malignant cells, which then spill over into the bloodstream and spread to other organs of the body. Acute forms of leukemia are the most common forms of leukemia in children. Chronic leukemia is distinguished by the excessive build up of relatively mature, but still abnormal, white blood cells. Typically taking months or years to progress, the cells are produced at a much higher rate than normal cells, resulting in many abnormal white blood cells in the blood. Whereas acute leukemia must be treated immediately, chronic forms are sometimes monitored for some time before treatment to ensure maximum effectiveness of therapy. Chronic leukemia mostly occurs in older people, but can theoretically occur in any age group. Additionally, the diseases are subdivided according to which kind of blood cell is affected. This split divides leukemias into lymphoblastic or lymphocytic leukemias and myeloid or myelogenous leukemias: In lymphoblastic or lymphocytic leukemias, the cancerous change takes place in a type of marrow cell that normally goes on to form lymphocytes, which are infection-fighting immune system cells. Most lymphocytic leukemias involve a specific subtype of lymphocyte, the B cell. In myeloid or myelogenous leukemias, the cancerous change takes place in a type of marrow cell that normally goes on to form red blood cells, some other types of white cells, and platelets.

Acute myeloid leukemia (AML), also known as acute myelogenous leukemia, is a cancer of the myeloid line of blood cells, characterized by the rapid growth of abnormal white blood cells that accumulate in the bone marrow and interfere with the production of normal blood cells. AML is the most common acute leukemia affecting adults, and its incidence increases with age. Although AML is a relatively rare disease, accounting for approximately 1.2% of cancer deaths in the United States, its incidence is expected to increase as the population ages.

The symptoms of AML are caused by replacement of normal bone marrow with leukemic cells, which causes a drop in red blood cells, platelets, and normal white blood cells. These symptoms include fatigue, shortness of breath, easy bruising and bleeding, and increased risk of infection. Although several risk factors for AML have been identified, the specific cause of the disease remains unclear. As an acute leukemia, AML progresses rapidly and is typically fatal within weeks or months if left untreated.

AML has several subtypes; treatment and prognosis varies among subtypes. Five-year survival varies from 15-70%, and relapse rate varies from 78-33%, depending on subtype.

Monoclonal antibodies are a class of therapeutic proteins that may be used to treat cell-proliferative diseases and disorders, in particular those affecting the hematopoietic system. A number of favorable properties of antibodies, including but not limited to specificity for target, ability to mediate immune effector mechanisms, and long half-life in serum, make antibodies powerful therapeutics. The present invention describes antibodies against the proto-oncogene FLT3.

FLT3 has been found to play a significant role in the onset and progression of leukemias, in particular AML, and first trials with FLT3 inhibitors in AML patients have shown promising results. However, there still exists the need for anti-FLT3 antibodies that are useful in the treatment of leukemias, such as AML.

The clinical success of antibodies directed against FLT3 depends on their potential mechanism(s) of action. There are a number of possible mechanisms by which antibodies mediate cellular effects, including anti-proliferation via blockage of needed growth pathways, intracellular signaling leading to apoptosis, enhanced down regulation and/or turnover of receptors, complement-dependent cytotoxicity (CDC), antibody-dependent cell-mediated cytotoxicity (ADCC), antibody-dependent cell-mediated phagocytosis (ADCP) and promotion of an adaptive immune response (Cragg et al, 1999, Curr Opin Immunol 11 541-547, Glennie et al, 2000, Immunol Today 21 403-410). Antibody efficacy may be due to a combination of these mechanisms, and their relative importance in clinical therapy for oncology appears to be cancer dependent.

The importance of FcγR-mediated effector functions for the activity of some antibodies has been demonstrated in mice (Clynes et al, 1998, Proc Natl Acad Sci USA 95 652-656, Clynes et al, 2000, Nat Med 6 443-446,), and from observed correlations between clinical efficacy in humans and their allotype of high (V158) or low (F158) affinity polymorphic forms of FcγRIIIa (Cartron et al, 2002, Blood 99 754-758, Weng & Levy, 2003, Journal of Clinical Oncology, 21 3940-3947). Together these data suggest that an antibody that is optimized for binding to certain FcγRs may better mediate effector functions, and thereby destroy target cells more effectively in patients Thus a promising means for enhancing the anti-tumor potency of antibodies is via enhancement of their ability to mediate cytotoxic effector functions such as ADCC, ADCP, and CDC Additionally, antibodies can mediate anti-tumor mechanism via growth inhibitory or apoptotic signaling that may occur when an antibody binds to its target on tumor cells. Such signaling may be potentiated when antibodies are presented to tumor cells bound to immune cells via FcγR. Therefore increased affinity of antibodies to FcγRs may result in enhanced antiproliferative effects.

Some success has been achieved at modifying antibodies with selectively enhanced binding to FcγRs to provide enhanced effector function. Antibody engineering for optimized effector function has been achieved using amino acid modifications (see for example US patent application US 2004-0132101 or US patent application 2006-0024298.

Unfortunately, it is not known a priori which mechanisms of action may be optimal for a given target antigen. Furthermore, it is not known which antibodies may be capable of mediating a given mechanism of action against a target cell. In some cases a lack of antibody activity, either Fv-mediated or Fc-mediated, may be due to the targeting of an epitope on the target antigen that is poor for mediating such activity. In other cases, the targeted epitope may be amenable to a desired Fv-mediated or Fc-mediated activity, yet the affinity (affinity of the Fv region for antigen or affinity of the Fc region for Fc receptors) may be insufficient. Towards addressing this problem, the present invention describes modifications to anti-FLT3 antibodies that provide Fc-mediated activities, for example de novo generated or optimized Fc-mediated activity.

Antibodies are immunological proteins that bind a specific antigen. In most mammals, including humans and mice, antibodies are constructed from paired heavy and light polypeptide chains. The light and heavy chain variable regions show significant sequence diversity between antibodies, and are responsible for binding the target antigen. Each chain is made up of individual immunoglobulin (Ig) domains, and thus the generic term immunoglobulin is used for such proteins.

Natural antibody structural units typically comprise a tetramer. Each tetramer is typically composed of two identical pairs of polypeptide chains, each pair having one "light" chain (typically having a molecular weight of about 25 kDa) and one "heavy" chain (typically having a molecular weight of about 50-70 kDa). Each of the light and heavy chains are made up of two distinct regions, referred to as the variable and constant regions. For the IgG class of immunoglobulins, the heavy chain is composed of four immunoglobulin domains linked from N- to C-terminus in the order VH-CH1-CH2-CH3, referring to the heavy chain variable domain, heavy chain constant domain 1, heavy chain constant domain 2, and heavy chain constant domain 3 respectively (also referred to as VH-Cγ1-Cγ2-Cγ3, referring to the heavy chain variable domain, constant gamma 1 domain, constant gamma 2 domain, and constant gamma 3 domain respectively). The IgG light chain is composed of two immunoglobulin domains linked from N- to C-terminus in the order VL-CL, referring to the light chain variable domain and the light chain constant domain, respectively. The constant regions show less sequence diversity, and are responsible for binding a number of natural proteins to elicit important biochemical events.

The variable region of an antibody contains the antigen binding determinants of the molecule, and thus determines the specificity of an antibody for its target antigen The variable region is so named because it is the most distinct in sequence from other antibodies within the same class In the variable region, three loops are gathered for each of the V domains of the heavy chain and light chain to form an antigen-binding site Each of the loops is referred to as a complementarity-determining region (hereinafter referred to as a "CDR"), in which the variation in the amino acid sequence is most significant There are 6 CDRs total, three each per heavy and light chain, designated $V_H$ CDR1, $V_H$ CDR2, $V_H$ CDR3, $V_L$ CDR1, $V_L$ CDR2, and $V_L$ CDR3. The variable region outside of the CDRs is referred to as the framework (FR) region Although not as diverse as the CDRs, sequence variability does occur in the FR region between different antibodies Overall, this characteristic architecture of antibodies provides a stable scaffold (the FR region) upon which substantial antigen binding diversity (the CDRs) can be explored by the immune system to obtain specificity for a broad array of antigens. A number of high-resolution structures are available for a variety of variable region fragments from different organisms, some unbound and some in complex with antigen. Sequence and structural features of antibody variable regions are disclosed, for example, in Morea et al., 1997, Biophys Chem 68:9-16; Morea et al., 2000, Methods 20:267-279, and the conserved features of antibodies are disclosed, for example, in Maynard et al., 2000, Annu Rev Biomed Eng 2:339-376.

Antibodies are grouped into classes, also referred to as isotypes, as determined genetically by the constant region. Human constant light chains are classified as kappa (Cκ) and lambda (Cλ) light chains. Human heavy chains are classified as mu, delta, gamma, alpha, or epsilon, and define the antibody's isotype as IgM, IgD, IgG, IgA, and IgE, respectively. The IgG class is the most commonly used for therapeutic purposes.

By "IgG" as used herein is meant a polypeptide belonging to the class of antibodies that are substantially encoded by a recognized immunoglobulin gamma gene. In humans this class comprises subclasses IgG1, IgG2, IgG3, and IgG4. In mice this class comprises subclasses IgG1, IgG2a, IgG2b and IgG3. IgM has subclasses, including, but not limited to, IgM 1 and IgM2. IgA has several subclasses, including but not limited to IgA1 and IgA2. Thus, "isotype" as used herein is meant any of the classes or subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE.

Also useful for the invention may be IgGs that are hybrid compositions of the natural human IgG isotypes. Effector functions such as ADCC, ADCP, CDC, and serum half-life differ significantly between the different classes of antibodies, including for example human IgG1, IgG2, IgG3, IgG4, IgA1, IgA2, IgD, IgE, IgG, and IgM (Michaelsen et al., 1992, Molecular Immunology, 29(3): 319-326). A number of studies have explored IgG1, IgG2, IgG3, and IgG4 variants in order to investigate the determinants of the effector function differences between them. See for example Canfield & Morrison, 1991, J. Exp. Med. 173: 1483-1491; Chappel et al., 1991, Proc. Natl. Acad. Sci. USA 88(20): 9036-9040; Chappel et al., 1993, Journal of Biological Chemistry 268:25124-25131; Tao et al., 1991, J. Exp. Med. 173: 1025-1028; Tao et al., 1993, J. Exp. Med. 178: 661-667; Redpath et al., 1998, Human Immunology, 59, 720-727.

As described in US patent application 2006-0134105 entitled "IgG Immunoglobulin Variants with Optimized Effector Function", it is possible to engineer amino acid modifications in an antibody that comprise constant regions from other immunoglobulin classes. Such engineered hybrid IgG compositions may provide improved effector function properties, including improved ADCC, phagocytosis, CDC, and serum half-life.

As is well known in the art, immunoglobulin polymorphisms exist in the human population. Gm polymorphism is determined by the IGHG1, IGHG2 and IGHG3 genes which have alleles encoding allotypic antigenic determinants referred to as G1m, G2m, and G3m allotypes for markers of the human IgG1, IgG2 and IgG3 molecules (no Gm allotypes have been found on the gamma 4 chain). Markers may be classified into "allotypes" and "isoallotypes". These are distinguished on different serological bases dependent upon the strong sequence homologies between isotypes. Allotypes are antigenic determinants specified by allelic forms of the Ig genes. Allotypes represent slight differences in the amino acid sequences of heavy or light chains of different individuals. Even a single amino acid difference can give rise to an allotypic determinant, although in many cases there are several amino acid substitutions that have occurred. Allotypes are sequence differences between alleles of a subclass whereby the antisera recognize only the allelic differences An isoallotype is an allele in one isotype which produces an epitope which is shared with a non-polymorphic homologous region of one or more other isotypes and because of this the antisera will react with both the relevant allotypes and the relevant homologous isotypes (Clark, 1997, IgG effector mechanisms, Chem. Immunol. 65-88-110, Gorman & Clark, 1990, Semin. Immunol. 2(6):457-66).

Allelic forms of human immunoglobulins have been well-characterized. Additionally, other polymorphisms have been characterized (Kim, et al., 2001, J. Mol. Evol. 54 1-9, incorporated herein it its entirety by reference) At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b5, b0, b3, b4, s, t, g1, c5, u, v, g5) (Lefranc, et al, The human IgG subclasses: molecular analysis of structure, function and regulation Pergamon, Oxford, pp 43-78 (1990), Lefranc, G et al., 1979, Hum. Genet.: 50, 199-21 1). Allotypes that are inherited in fixed combinations are called Gm haplotypes. The antibodies of the present invention may be substantially encoded by any allotype, isoallotype, or haplotype of any immunoglobulin gene Antibodies of the present invention may be substantially encoded by genes from any organism, e g, mammals, including but not limited to humans, rodents including but not limited to mice and rats, lagomorpha including but not limited to rabbits and hares, camelidae including but not limited to camels, llamas, and dromedaries, and non-human primates, including but not limited to Prosimians, Platyrrhini (New World monkeys), Cercopithecoidea (Old World monkeys), and Hominoidea including the Gibbons and Lesser and Great Apes.

In one embodiment, the antibodies of the present invention are substantially human. The antibodies of the present invention may be substantially encoded by immunoglobulin genes belonging to any of the antibody classes. In one embodiment, the antibodies of the present invention comprise sequences belonging to the IgG class of antibodies, including human subclasses IgG1, IgG2, IgG3, and IgG4. In an alternate embodiment, the antibodies of the present invention comprise sequences belonging to the IgA (including human subclasses IgA1 and IgA2), IgD, IgE, IgG, or IgM classes of antibodies. The antibodies of the present invention may comprise more than one protein chain. That is, the present invention may find use in an antibody that is a monomer or an oligomer, including a homo- or hetero-oligomer.

In one embodiment, the antibodies of the invention are based on human IgG sequences, and thus human IgG sequences are used as the "base" sequences against which other sequences are compared, including but not limited to sequences from other organisms, for example rodent and primate sequences, as well as sequences from other immunoglobulin classes such as IgA, IgE, IgD, IgM, and the like. It is contemplated that, although the antibodies of the present invention are engineered in the context of one parent antibody, the variants may be engineered in or "transferred" to the context of another, second parent antibody. This is done by determining the "equivalent" or "corresponding" residues and substitutions between the first and second antibodies, typically based on sequence or structural homology between the sequences of the two antibodies. In order to establish homology, the amino acid sequence of a first antibody outlined herein is directly compared to the sequence of a second antibody. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first antibody are defined. Alignment of conserved residues may conserve 100% of such residues. However, alignment of greater than 75% or as little as 50% of conserved residues is also adequate to define equivalent residues Equivalent residues may also be defined by determining structural homology between a first and second antibody that is at the level of tertiary structure for antibodies whose structures have been determined. In this case, equivalent residues are defined as those for which the atomic coordinates of two or more of the main chain atoms of a particular amino acid residue of the parent or precursor (N on N, CA on CA, Con C and O on O) are within 0.13 nm, e g, 0.1 nm, after alignment. Alignment is achieved after the best model has been oriented and positioned to give the maximum overlap of atomic coordinates of non-hydrogen protein atoms of the proteins Regardless of how equivalent or corresponding residues are determined, and regardless of the identity of the parent antibody in which the antibodies are made, what is meant to be conveyed is that the antibodies discovered by the present invention may be engineered into any second parent antibody that has significant sequence or structural homology with the antibody Thus for example, if a variant antibody is generated wherein the parent antibody is human IgG1, by using the methods described above or other methods for determining equivalent residues, the variant antibody may be engineered in a human IgG2 parent antibody, a human IgA parent antibody, a mouse IgG2a or IgG2b parent antibody, and the like Again, as described above, the context of the parent antibody does not affect the ability to transfer the antibodies of the present invention to other parent antibodies For example, the variant antibodies that are engineered in a human IgG1 antibody that targets one antigen epitope may be transferred into a human IgG2 antibody that targets a different antigen epitope, and so forth.

In the IgG class of immunoglobulins, there are several immunoglobulin domains in the heavy chain. By "immunoglobulin (Ig) domain" herein is meant a region of an immunoglobulin having a distinct tertiary structure. Of interest in the present invention are the domains of the constant heavy chain, including, the constant heavy (CH) domains and the hinge. In the context of IgG antibodies, the IgG isotypes each have three CH regions: "CH1" refers to positions 118-220, "CH2" refers to positions 237-340, and "CH3" refers to positions 341-447 according to the EU index as in Kabat. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "tower hinge" generally referring to positions 226 or 230. The constant heavy chain, as defined herein, refers to the N-terminus of the CH1 domain to the C-terminus of the CH3 domain, thus comprising positions 118-447, wherein numbering is according to the EU index. The constant light chain comprises a single domain, and as defined herein refers to positions 108-214 of Cκ or Cλ, wherein numbering is according to the EU index.

Specifically included within the definition of "antibody" are full-length antibodies. By "full length antibody" herein is meant the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains VL and CL, and each heavy chain comprising immunoglobulin domains VH, CH1 (Cγ1), CH2 (Cγ2), and CH3 (Cγ3). In some mammals, for example in camels and llamas, IgG antibodies may consist of only two heavy chains, each heavy chain comprising a variable domain attached to the Fc region.

Alternatively, the antibodies can be a variety of structures, including, but not limited to antibody fragments. Antibody fragments include but are not limited to bispecific antibodies, minibodies, domain antibodies, synthetic antibodies, antibody mimetics, chimeric antibodies, antibody fusions (sometimes referred to as "antibody conjugates"), and fragments of each, respectively. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment, which consists of a single variable region, (v) isolated CDR regions, (vi) F(ab')$_2$ fragments, a bivalent fragment comprising two linked Fab fragments (vii) single chain Fv molecules (scFv), wherein a VH domain and a VL domain are linked by a peptide linker which allows the two domains to associate to form an antigen binding site (viii) bispecific single chain Fv dimers and (ix) "diabodies" or "triabodies", multivalent or multispecific fragments constructed by gene fusion. The antibody fragments may be modified. For example, the molecules may be stabilized by the incorporation of disulfide bridges linking the VH and VL domains Examples of antibody formats and architectures are described in Holliger & Hudson, 2006, Nature Biotechnology 23(9): 1126-1136, and Carter 2006, Nature Reviews Immunology 6:343-357 and references cited therein.

Antibodies of the invention may include multispecific antibodies, notably bispecific antibodies, also sometimes referred to as "diabodies". These are antibodies that bind to two (or more) different antigens. Diabodies can be manufactured in a variety of ways known in the art, e.g., prepared chemically or from hybrid hybridomas. In one embodiment, the antibody is a minibody. Minibodies are minimized antibody-like proteins comprising a scFv joined to a CH3 domain. In some cases, the scFv can be joined to the Fc region, and may include some or all of the hinge region. For a description of multispecific antibodies see Holliger & Hudson, 2006, Nature Biotechnology 23(9): 1126-1136 and references cited therein.

In one embodiment, the antibody of the invention is an antibody fragment. Of particular interest are antibodies that comprise Fc regions, Fc fusions, and the constant region of the heavy chain (CH1-hinge-CH2-CH3) Antibodies of the present invention may comprise Fc fragments An Fc fragment of the present invention may comprise from 1-90% of the Fc region, e.g, 10-90%, 30-90%, etc Thus for example, an Fc fragment of the present invention may comprise an IgG1 Cγ2 domain, an IgG1 Cγ2 domain and hinge region, an IgG1 Cγ3 domain, and so forth. In one embodiment, an Fc fragment of the present invention additionally comprises a fusion partner, effectively making it an Fc fragment fusion. Fc fragments may or may not contain extra polypeptide sequence.

Immunogenicity is the result of a complex series of responses to a substance that is perceived as foreign, and may include production of neutralizing and non-neutralizing antibodies, formation of immune complexes, complement activation, mast cell activation, inflammation, hypersensitivity responses, and anaphylaxis. Several factors can contribute to protein immunogenicity, including but not limited to protein sequence, route and frequency of administration, and patient population. Immunogenicity may limit the efficacy and safety of a protein therapeutic in multiple ways. Efficacy can be reduced directly by the formation of neutralizing antibodies Efficacy may also be reduced indirectly, as binding to either neutralizing or non-neutralizing antibodies typically leads to rapid clearance from serum Severe side effects and even death may occur when an immune reaction is raised. Thus in one embodiment, protein engineering is used to reduce the immunogenicity of the antibodies of the present invention.

In some embodiments, the scaffold components can be a mixture from different species. Such antibody may be a chimeric antibody and/or a humanized antibody. In general, both "chimeric antibodies" and "humanized antibodies" refer to antibodies that combine regions from more than one species. "Chimeric antibodies" traditionally comprise variable region(s) from a mouse (or rat, in some cases) and the constant region(s) from a human (Morrison et al, 1984, Proc Natl Acad Sci USA 81 6851-6855).

By "humanized" antibody as used herein is meant an antibody comprising a human framework region (FR) and one or more complementarity determining regions (CDRs) from a non-human (usually mouse or rat) antibody. The non-human antibody providing the CDRs is called the "donor" and the human immunoglobulin providing the framework is called the "acceptor". Humanization relies principally on the grafting of donor CDRs onto acceptor (human) VL and VH frameworks (Winter U.S. Pat. No. 5,225,539). This strategy is referred to as "CDR grafting". "Backmutation" of selected acceptor framework residues to the corresponding donor residues is often required to regain affinity that is lost in the initial grafted construct (U.S. Pat. No. 5,693,762). The humanized antibody optimally also will comprise at least a portion of an immunoglobulin constant region, typically that of a human immunoglobulin, and thus will typically comprise a human Fc region. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein). Humanization or other methods of reducing the immunogenicity of nonhuman antibody variable regions may include resurfacing methods, as described for example in Roguska et al., 1994, Proc Natl Acad Sci USA 91 969-973). In one embodiment, selection based methods may be employed to humanize and/or affinity mature antibody variable regions, that is, to increase the affinity of the variable region for its target antigen. Other humanization methods may involve the grafting of only parts of the CDRs, including but not limited to methods described in, Tan et al, 2002, J Immunol 169 1119-1125, De Pascalis et al, 2002, J Immunol 169 3076-3084. Structure-based methods may be employed for humanization and affinity maturation, for example as described in U.S. Pat. No. 7,117,096 and related applications.

In certain variations, the immunogenicity of the antibody is reduced using a method described in US patent application 2006-0008883, entitled "Methods of Generating Variant Proteins with Increased Host String Content and Compositions Thereof, filed on Dec. 3, 2004.

Modifications to reduce immunogenicity may include modifications that reduce binding of processed peptides derived from the parent sequence to MHC proteins. For example, amino acid modifications would be engineered such that there are no or a minimal number of immune epitopes that are predicted to bind, with high affinity, to any prevalent MHC alleles. Several methods of identifying MHC-binding epitopes in protein sequences are known in the art and may be used to score epitopes in an antibody of the present invention. See, for example, US patent applications 2002-0119492, 2004-0230380 or 2006-0148009 and references cited therein.

In an alternate embodiment, the antibodies of the present invention may be fully human, that is the sequences of the antibodies are completely or substantially human. "Fully human antibody" or "complete human antibody" refers to a human antibody having the gene sequence of an antibody derived from a human chromosome with the modifications outlined herein. A number of methods are known in the art for generating fully human antibodies, including the use of transgenic mice (Bruggemann et al., 1997, Curr Opin Biotechnol 8:455-458,) or human antibody libraries coupled with selection methods (Griffiths et al., 1998, Curr Opin Biotechnol 9:102-108).

The antibodies of the present invention target FLT3 and may comprise the variable regions (e.g., the CDRs) of any known or undiscovered anti-FLT3 antibody. Antibodies of the invention may display selectivity for FLT3. Examples include full-length versus splice variants, cell-surface vs. soluble form's selectivity for various polymorphic variants, or selectivity for specific conformational forms of a target. An antibody of the present invention may bind any epitope or region on FLT3 and may be specific for fragments, mutant forms, splice forms, or aberrant forms of the antigens. A number of useful antibodies have been discovered that target FLT3 that may find use in the present invention.

Suitable FLT3 antibodies include the anti-FLT3 antibodies 408 and BV10, as disclosed in U.S. Pat. No. 5,777,084 and U.S. Pat. No. 6,156,882.

The antibodies of the present invention may find use in a wide range of products. In one embodiment the antibody of the invention is a therapeutic, a diagnostic, or a research reagent. In one embodiment, an antibody of the invention is a therapeutic. An antibody of the present invention may find use in an antibody composition that is monoclonal or polyclonal. In one embodiment, the antibodies of the present invention are used to kill target cells that bear the target antigen, for example cancer cells. In an alternate embodiment, the antibodies of the present invention are used to block, antagonize, or agonize the target antigen. In an alternate embodiment, the antibodies of the present invention are used to block, antagonize, or agonize the target antigen and kill the target cells that bear the target antigen.

It will be recognized that the sequences of the variable domains including the CDRs identified herein can be combined in any combination in an antibody. Further, these sequences may be independently modified by adding all or part of an Fc region or Fc variant as disclosed herein. The modified sequences can also be combined in any combination in an antibody.

The present invention is directed to antibodies comprising modifications, wherein the modifications alter affinity to one or more Fc receptors, and/or alter the ability of the antibody to mediate one or more effector functions. Modifications of the invention include amino acid modifications.

The inventors of the present invention have surprisingly found that by introducing the amino acid substitutions 239D and 332E in the CH2 domain of the Fc part of known anti-FLT3 antibodies, such as 4G8 and BV10 (supra), the cell killing activity of these antibodies can be significantly increased or even detected and generated for the first time. In one embodiment, the amino acid substitutions are S239D and I332E. This is surprising, as it has been experimentally shown that the same modifications do not generally increase cell killing activity. In other words, in different antibodies directed to a different target antigen, the introduction of these substitutions had no measurable effect on cell killing.

In addition, such modified antibodies can comprise further amino acid modifications at heavy chain constant region positions 221, 222, 223, 224, 225, 227, 228, 230, 231, 232, 233, 234, 235, 236, 237, 238, 240, 241, 243, 244, 245, 246, 247, 249, 255, 258, 260, 262, 263, 264, 265, 266, 267, 268, 269, 270, 271, 272, 273, 274, 275, 276, 278, 280, 281, 282, 283, 284, 285, 286, 288, 290, 291, 292, 293, 294, 295, 296, 297, 298, 299, 300, 301, 302, 303, 304, 305, 313, 317, 318, 320, 322, 323, 324, 325, 326, 327, 328, 329, 330, 331, 333, 334, 335, 336, and 337, which have been found to allow modification of FcγR binding properties, effector function, and potentially clinical properties of antibodies (See U.S. Ser. No. 11/124,620, filed May 5, 2005, entitled "Optimized Fc Variants").

In particular, additional variants that alter binding to one or more human Fc receptors may comprise an amino acid modification in the heavy chain constant region, as described herein, selected from the group consisting of 221K, 221Y, 222E, 222Y, 223E, 223K, 224E, 224Y, 225E, 225K, 225W, 227E, 227G, 227K, 227Y, 228E, 228G, 228K, 228Y, 230A, 230E, 230G, 230Y, 231 E, 231 G, 231 K, 231 P, 231 Y, 232E, 232G, 232K, 232Y, 233A, 233D, 233F, 233G, 233H, 233I, 233K, 233L, 233M, 233N, 233Q, 233R, 233S, 233T, 233V, 233W, 233Y, 234A, 234D, 234E, 234F, 234G, 234H, 234I, 234K, 234M, 234N, 234P, 234Q, 234R, 234S, 234T, 234V, 234W, 234Y, 235A, 235D, 235E, 235F, 235G, 235H, 235I, 235K, 235M, 235N, 235P, 235Q, 235R, 235S, 235T, 235V, 235W, 235Y, 236A, 236D, 236E, 236F, 236H, 236I, 236K, 236L, 236M, 236N, 236P, 236Q, 236R, 236S, 236T, 236V, 236W, 236Y, 237D, 237E, 237F, 237H, 237I, 237K, 237L, 237M, 237N, 237P, 237Q, 237R, 237S, 237T, 237V, 237W, 237Y, 238D, 238E, 238F, 238G, 238H, 238I, 238K, 238L, 238M, 238N, 238Q, 238R, 238S, 238T, 238V, 238W, 238Y, 240A, 240I, 240M, 240T, 241D, 241E, 241L, 241R, 241S, 241W, 241Y, 243E, 243H, 243L, 243Q, 243R, 243W, 243Y, 244H, 245A, 246D, 246E, 246H, 246Y, 247G, 247V, 249H, 249Q, 249Y, 255E, 255Y, 258H1258S, 258Y, 260D, 260E, 260H, 260Y, 262A, 262E, 262F, 2621, 262T, 263A, 2631, 263M, 263T, 264A, 264D, 264E, 264F, 264G, 264H, 2641, 264K, 264L, 264M, 264N, 264P, 264Q, 264R, 264S, 264T, 264W, 264Y, 265F, 265G, 265H, 2651, 265K, 265L, 265M, 265N, 265P, 265Q, 265R, 265S, 265T, 265V, 265W, 265Y, 266A, 2661, 266M, 266T, 267D, 267E, 267F, 267H, 2671, 267K, 267L, 267M, 267N, 267P, 267Q, 267R, 267T, 267V, 267W, 267Y, 268D, 268E, 268F, 268G, 2681, 268K, 268L, 268M, 268P, 268Q, 268R, 268T, 268V, 268W, 269F, 269G, 269H, 2691, 269K, 269L, 269M, 269N, 269P, 269R, 269S, 269T, 269V, 269W, 269Y, 270F, 270G, 270H, 2701, 270L, 270M, 270P, 270Q, 270R, 270S, 270T, 270W, 270Y, 271A, 271D, 271E, 271F, 271G, 271H, 2711, 271K, 271L, 271M, 271N, 271Q, 271R, 271S, 271T, 271V, 271W, 271Y, 272D, 272F, 272G, 272H, 2721, 272K, 272L, 272M, 272P, 272R, 272S, 272T, 272V, 272W, 272Y, 2731, 274D, 274E, 274F, 274G, 274H, 2741, 274L, 274M, 274N, 274P, 274R, 274T, 274V, 274W, 274Y, 275L, 275W, 276D, 276E, 276F, 276G, 276H, 2761, 276L, 276M, 276P, 276R, 276S, 276T, 276V, 276W, 276Y, 278D, 278E, 278G, 278H, 2781, 278K, 278L, 278M, 278N, 278P, 278Q, 278R, 278S, 278T, 278V, 278W, 280G, 280K, 280L, 280P, 280W, 281D, 281E, 281 K, 281N, 281P, 281Q, 281Y, 282E, 282G, 282K, 282P, 282Y, 283G, 283H, 283K, 283L, 283P, 283R, 283Y, 284D, 284E, 284L, 284N, 284Q, 284T, 284Y, 285D, 285E, 285K, 285Q, 285W, 285Y, 286E, 286G, 286P, 286Y, 288D, 288E, 288Y, 290D, 290H, 290L, 290N, 290W, 291D, 291E, 291G, 291H, 2911, 291Q, 291T, 292D, 292E, 292T, 292Y, 293F, 293G, 293H, 2931, 293L, 293M, 293N, 293P, 293R, 293S, 293T, 293V, 293W, 293Y, 294F, 294G, 294H, 2941, 294K, 294L1294M1294P, 294R, 294S, 294T, 294V, 294W, 294Y, 295D, 295E, 295F, 295G, 295H, 2951, 295M1295N, 295P1295R1295S, 295T1295V1295W1295Y, 296A, 296D, 296E, 296G, 296H12961, 296K1296L1296M, 296N1296Q1296R1296S1296T1296V, 297D, 297E1297F1297G, 29711, 2971, 297K, 297L, 297M1297P1297Q1297R, 297S1297T, 297V, 297W, 297Y, 298A, 298D, 298E, 298F, 298H, 2981, 298K, 298M, 298N, 298Q, 298R, 298W, 298Y, 299A, 299D, 299E, 299F, 299G, 299H, 2991, 299K, 299L, 299M, 299N, 299P, 299Q, 299R, 299S1299V, 299W, 299Y, 300A, 300D1300E, 300G, 300H, 300K, 300M, 300N, 300P, 300Q, 300R, 300S, 300T, 300V, 300W, 301D, 301E, 301H, 301Y, 302I, 303D, 303E, 303Y, 304D, 304H, 304L, 304N, 304T, 305E, 305T, 305Y, 313F, 317E, 317Q, 318H, 318L, 318Q, 318R, 318Y, 320D, 320F, 320G, 320H, 320I, 320L, 320N, 320P, 320S, 320T, 320V, 320W, 320Y, 322D, 322F1322G, 322H13221, 322P1322S1322T, 322V, 322W, 322Y, 3231, 324D, 324F, 324G, 324H, 3241, 324L, 324M, 324P, 324R, 324T, 324V, 324W, 324Y, 325A, 325D, 325E, 325F, 325G, 325H, 3251, 325K, 325L, 325M, 325P, 325Q, 325R, 325S, 325T, 325V, 325W1325Y, 326E, 3261, 326L, 326P, 326T, 327D, 327E, 327F, 327H, 3271, 327K, 327L, 327M, 327N, 327P, 327R, 327S, 327T, 327V, 327W, 327Y, 328A, 328D, 328E, 328F, 328G, 328H, 3281, 328K, 328M, 328N, 328P, 328Q, 328R, 328S, 328T, 328V, 328W, 328Y, 329D, 329E, 329F, 329G, 329H, 3291, 329K, 329L, 329M, 329N, 329Q, 329R, 329S, 329T, 329V, 329W, 329Y, 330E, 330F, 330G, 330H, 3301, 330L, 330M, 330N, 330P, 330R, 330S, 330T, 330V, 330W, 330Y, 331 D, 331 F, 331 H, 3311, 331 L, 331 M, 331Q, 331 R, 33 T, 331V, 331W, 331Y, 333A, 333F, 333H, 333I, 333L, 333M, 333P, 333T, 333Y, 334A, 334F, 334I, 334L, 334P, 334T, 335D, 335F, 335G, 335H, 335I, 335L, 335M, 335N, 335P, 335R, 335S, 335V, 335W, 335Y, 336E, 336K, 336Y, 337E, 337H, and 337N, wherein numbering is according to the EU index.

Furthermore, the invented antibodies can comprise further amino acid modifications outside the Fc region, such as those described in U.S. Pat. No. 7,276,585, filed Mar. 24, 2005, entitled "Immunoglobulin variants outside the Fc region", including amino acid modifications at heavy chain constant region positions 118, 119, 120, 121, 122, 124, 126, 129, 131, 132, 133, 135, 136, 137, 138, 139, 147, 148, 150, 151, 152, 153, 155, 157, 159, 160, 161, 162, 163, 164, 165, 166, 167, 168, 169, 171, 172, 173, 174, 175, 176, 177, 178, 179, 180, 183, 187, 188, 189, 190, 191, 192, 193, 194, 195, 196, 197, 198, 199, 201, 203, 205, 206, 207, 208, 209, 210, 211, 212, 213, 214, 216, 217, 218, 219, 221, 222, 223, 224, 225, 226, 227, 228, 229, 230, 231, 232, 233, 234, 235, and 236 and/or including amino acid modifications at light chain constant region positions 108, 109, 110, 111, 112, 114, 116, 121, 122, 123, 124, 125, 126, 127, 128, 129, 131, 137, 138, 140, 141, 142, 143, 145, 147, 149, 150, 151, 152, 153, 154, 155, 156, 157, 159, 160, 161, 162, 163, 164, 165, 166, 167, 168, 169, 170, 171, 172, 173, 174, 176, 180, 181, 182, 183, 184, 185, 187, 188, 189, 190, 191, 193, 195, 197, 199, 200, 202, 203, 204, 205, 206, 207, 208, 210, 211, 212, and 213.

These modifications may allow further modification of FcγR binding properties, effector function, and potentially clinical properties of antibodies. In particular, variants that alter binding to one or more human Fc receptors may comprise an amino acid modification in the heavy chain constant region, as described herein, selected from the group consisting of 118K, 118E, 118Y, 119R, 119E, 119Y, 120R, 120E, 120I, 121 E, 121Y, 121 H, 122E, 122R, 124K, 124E, 124Y, 126K, 126D, 129L, 129D, 131G, 131T, 132D, 132R, 132L, 133R, 133E, 133L, 1351, 135E, 135K, 136E, 136K, 1361, 137E, 138S, 138R, 138D, 1391, 139E, 139K, 147A, 147E, 148Y, 148K, 150L, 150K, 150E, 151 A, 151 D, 152L, 152K, 153L, 153D, 155E, 155K, 1551, 157E, 157K, 157Y, 159K, 159D, 159L, 160K, 160E, 160Y, 161 D, 162D, 162K, 162Y, 163R, 164R, 164E, 164Y, 165D, 165R, 165Y, 166D, 167A, 168L, 169E, 171G, 171 H, 172K, 172L, 172E, 173T, 173D, 174E, 174K, 174Y, 175D, 175L, 176D, 176R, 176L, 177R, 177T, 177Y, 178D, 179K, 179Y, 179E, 180K, 180L, 180E, 183T, 1871, 187K, 187E, 1881, 189D, 189G, 1901, 190K, 190E, 191 D, 191 R, 191Y, 192N, 192R, 192L, 193F, 193E, 194R, 194D, 195R, 195D, 195Y, 196K, 196D, 196L, 197R, 197E, 197Y, 198L, 199T, 199D, 199K, 201 E, 201 K, 201 L, 203D, 203L, 203K, 205D, 205L, 206A, 206E, 207K, 207D, 208R, 208E, 208Y, 209E, 209K, 209Y, 210L, 210E, 210Y, 211 R, 211 E, 211Y, 212Q, 212K, 212H, 212L, 212Y, 213N, 213E, 213H, 213L, 213Y, 214N, 214E, 214H, 214L, 214Y, 216N, 216K, 216H, 216L, 216Y, 217D, 217H, 217A, 217V, 217G, 218D, 218E, 218Q, 218T, 218H, 218L, 218Y, 219D, 219E, 219Q, 219K, 219T, 219H, 219L, 219I, 219Y, 205A, 210A, 213A, 214A, 218A, 221 K, 221Y, 221 E, 221 N, 221Q, 221 R, 221 S, 221T, 221 H, 221A, 221V, 221 L1 221I, 221 F, 221 M, 221W, 221 P1 221G, 222E, 222Y1 222D1 222N, 222Q, 222R, 222S, 222T, 222H, 222V, 222L, 222I, 222F, 222M1 222W, 222P, 222G, 222A, 223D, 223N, 223Q, 223R, 223S, 223H, 223A, 223V, 223L, 223I, 223F, 223M, 223Y, 223W1 223P, 223G, 223E1 223K, 224D, 224N, 224Q, 224K, 224R, 224S, 224T, 224V1 224L1 224I, 224F1 224M1 224W, 224P, 224G, 224E, 224Y, 224A, 225D, 225N1 225Q, 225R, 225S, 225H, 225A1 225V, 225L, 225I, 225F1 225M, 225Y1 225P1 225G1 225E, 225K, 225W, 226S, 227E, 227K, 227Y, 227G, 227D, 227N, 227Q, 227R, 227S, 227T, 227I1, 227A, 227V, 227L, 227I, 227F, 227M, 227W, 228K, 228Y1 228G, 228D1 228N1 228Q1 228R, 228T, 228H1 228A, 228V, 228L, 228I, 228F, 228M, 228W, 229S, 230A, 230E, 230Y, 230G, 230D, 230N, 230Q, 230K, 230R, 230S, 230T, 230H, 230V, 230L, 230I, 230F1 230M1 230W, 231 K, 231 P, 231 D, 231 N, 231Q, 231 R, 231S, 231T, 231 H1 231V1 231 L, 231I, 231 F, 231 M, 231W, 232E, 232K, 232Y, 232G, 232D, 232N, 232Q, 232R, 232S, 232T, 232H, 232A, 232V, 232L, 232I, 232F, 232M1 232W, 233D, 233N1 233Q, 233R, 233S, 233T, 233H, 233A, 233V, 233L, 233I, 233F, 233M, 233Y, 233W, 233G, 234D, 234E, 234N, 234Q, 234T, 234H, 234Y, 234I, 234V, 234F1 234K, 234R, 234S, 234A, 234M, 234G, 235D, 235S, 235N, 235Q, 235T, 235H, 235Y, 235I, 235V, 235F, 235E, 235K, 235R1 235A1 235M, 235W, 235P, 235G, 236D, 236E, 236N, 236Q1 236K, 236R, 236S, 236T, 236H, 236A, 236V, 236L, 236I, 236F1 236M, 236Y, 236W, and 236P, wherein numbering is according to the EU index.

In particular, variants that alter binding to one or more human Fc receptors may comprise an amino acid modification in the light chain constant region, as described herein, selected from the group consisting of 108D, 108I, 108Q, 109D, 109P, 109R, 110E, 110I, 110K, 111 E, 111 K, 1 11 L1 112E, 112R, 112Y1 114D, 114I, 114K, 116T, 121 D1 122R, 122S, 122Y, 123L, 123R, 124E, 125E, 125K, 126D, 126L, 126Q, 127A, 127D, 127K, 128N, 129E, 129I, 129K, 131T, 137K, 137S, 138D, 138K, 138L, 140E1 140H, 140K, 141 E1 141 K, 142D, 142G, 142L, 143A, 143L, 143R, 145D, 145T, 145Y, 147A, 147E, 147K, 149D, 149Y1 150A, 151I, 151 K1 152L, 152R, 152S, 153D, 153H, 153S, 154E, 154R, 154V, 155E, 155I, 155K, 156A, 156D, 156R, 157N, 158D, 158L, 158R, 159E1 159K1 159L, 160K, 160V, 161 K1 161 L1 162T, 163E, 163K, 163T, 164Q, 165K, 165P, 165Y, 166E, 166M, 166S1 167K1 167L, 168K, 168Q, 168Y, 169D, 169H, 169S, 170I, 170N, 170R, 171A1 171 N, 171V, 172E1 172I1 172K, 173K, 173L, 173Q, 174A, 176T, 180E, 180K, 180S, 181 K1 182E, 182R, 182T, 183D, 183L, 183P, 184E, 184K, 184Y, 185I, 185Q, 185R, 187K, 187Y1 188E, 188S, 188Y, 189D, 189K, 189Y, 190E, 190L, 190R, 191 E, 191 R1 191S, 193E, 193K, 193S, 195I, 195K, 195Q, 197E, 197K, 197L, 199E, 199K, 199Y, 200S, 202D, 202R, 202Y, 203D, 203L, 203R, 204T, 205E, 205K, 206E, 206I, 206K, 207A, 207E, 207L, 208E, 208K, 208T, 210A, 210E, 210K, 211A, 211 E, 211 P, 212E, 212K, 212T, 213L, 213R, wherein numbering is according to the EU index.

Additional substitutions that may also be used in the present invention include other substitutions that modulate Fc receptor affinity, FcγR-mediated effector function, and/or complement mediated effector function include but are not limited to 298A, 298T, 326A, 326D, 326E, 326W, 326Y, 333A, 333S, 334L, and 334A (U.S. Pat. No. 6,737,056; Shields et al., Journal of Biological Chemistry, 2001, 276(9): 6591-6604; U.S. Pat. No. 6,528,624; Idusogie et al., 2001, J. Immunology 166:2571-2572), 247L, 255L, 270E, 392T, 396L, and 421 K (U.S. Ser. No. 10/754,922; U.S. Ser. No. 10/902,588), and 280H, 280Q, and 280Y (U.S. Ser. No. 10/370,749), In other embodiments, antibodies of the present invention may be combined with constant heavy chain variants that alter FcRn binding. These include modifications that modify FcRn affinity in a pH-specific manner. In particular, variants that increase Fc binding to FcRn include but are not limited to: 250E, 250Q, 428L, 428F, 250Q/428L (Hinton et al., 2004, J. Biol. Chem. 279(8): 6213-6216, Hinton et al. 2006 Journal of Immunology 176:346-356, U.S. Ser. No. 11/102,621, PCT/US2003/033037, PCT/US2004/011213, U.S. Ser. No. 10/822,300, U.S. Ser. No. 10/687,118, PCT/US2004/034440, U.S. Ser. No. 10/966,673), 256A, 272A, 286A, 305A, 307A, 311 A, 312A, 376A, 378Q, 380A, 382A, 434A (Shields et al, Journal of Biological Chemistry, 2001, 276(9):6591-6604, U.S. Ser. No. 10/982,470, U.S. Pat. No. 6,737,056, U.S. Ser. No. 11/429,793, U.S. Ser. No. 11/429,786, PCT/US2005/02951 1, U.S. Ser. No. 11/208,422), 252F, 252T, 252Y, 252W, 254T, 256S, 256R, 256Q, 256E, 256D, 256T, 309P, 311S, 433R, 433S, 433I, 433P, 433Q, 434H, 434F, 434Y, 252Y/254T/256E, 433K/434F/436H, 308T/309P/311S (Dall Acqua et al. Journal of Immunology, 2002, 169:5171-5180, U.S. Pat. No. 7,083,784, PCT/US97/03321, U.S. Pat. No. 6,821,505, PCT/US01/48432, U.S. Ser. No. 11/397,328), 257C, 257M, 257L, 257N, 257Y, 279E, 279Q, 279Y, insertion of Ser after 281, 283F, 284E, 306Y, 307V, 308F, 308Y 311V, 385H, 385N, (PCT/US2005/041220, U.S. Ser. No. 11/274,065, U.S. Ser. No. 11/436,266) 204D, 284E, 285E, 286D, and 290E (PCT/US2004/037929 incorporated herein it its entirety by reference).

In some embodiments of the invention, antibodies may comprise isotypic modifications, that is, modifications in a parent IgG to the amino acid type in an alternate IgG.

The present invention provides variant antibodies that are optimized for a number of therapeutically relevant properties. A variant antibody comprises one or more amino acid modifications relative to a parent antibody, wherein the amino acid modification(s) provide one or more optimized properties. Thus the antibodies of the present invention are variant antibodies. An antibody of the present invention differs in amino acid sequence from its parent antibody by virtue of at least the two amino acid modifications 239D and 332E. Additionally, the variant antibodies of the present invention may comprise more than the two afore-mentioned amino acid modifications as compared to the parent, for example from about three to fifty amino acid modifications, e.g., from about three to ten amino acid modifications, from about three to about five amino acid modifications, etc., compared to the parent. Thus the sequences of the variant antibodies and those of the parent antibodies are substantially homologous. For example, the variant antibody sequences herein will possess about 80% homology with the parent antibody sequence, e.g., at least about 90% homology, e at least about 95% homology, etc.

The antibodies of the present invention may comprise amino acid modifications that provide optimized effector function properties relative to the parent. Substitutions and optimized effector function properties are described in US patent application 2004-0132101, PCT application US03/30249, and U.S. Pat. No. 7,317,091 Ser. No. 10/822,231, (Properties that may be optimized include but are not limited to enhanced or reduced affinity for an FcγR. In one embodiment, the antibodies of the present invention are optimized to possess enhanced affinity for a human activating FcγR, e.g., FcγRI, FcγRIIa, FcγRIIc, FcγRIIIa, and FcγRIIIb. In one embodiment, an antibody of the invention is optimized to possess enhanced affinity for a human FcγRIIIa. In an alternate embodiment, the antibodies are optimized to possess reduced affinity for the human inhibitory receptor FcγRIIb. These embodiments are anticipated to provide antibodies with enhanced therapeutic properties in humans, for example enhanced effector function and greater anti-cancer potency.

In other embodiments, antibodies of the present invention provide enhanced affinity for one or more FcγRs, yet reduced affinity for one or more other FcγRs. For example, an antibody of the present invention may have enhanced binding to FcγRIIIa, yet reduced binding to FcγRIIb. Alternately, an antibody of the present invention may have enhanced binding to FcγRIIa and FcγRI, yet reduced binding to FcγRIIb.

The modifications of the invention may enhance binding affinity for one or more FcγRs. By "greater affinity" or "improved affinity" or "enhanced affinity" or "better affinity" than a parent immunoglobulin, as used herein is meant that an Fc variant binds to an Fc receptor with a significantly higher equilibrium constant of association (Ka) or lower equilibrium constant of dissociation (Kd) than the parent polypeptide when the amounts of variant and parent polypeptide in the binding assay are essentially the same. For example, the Fc variant with improved FcγR binding affinity may display from about 5 fold to about 1000 fold, e g from about 10 fold to about 500 fold improvement in Fc receptor binding affinity compared to the parent polypeptide, where Fc receptor binding affinity is determined by methods known in the art. Accordingly, by "reduced affinity" as compared to a parent Fc polypeptide as used herein is meant that an Fc variant binds an Fc receptor with significantly lower Ka or higher Kd than the parent polypeptide.

Embodiments comprise optimization of Fc binding to a human FcγR, however in alternate embodiments the antibodies of the present invention possess enhanced or reduced affinity for FcγRs from nonhuman organisms, including but not limited to rodents and non-human primates. Antibodies that are optimized for binding to a nonhuman FcγR may find use in experimentation. For example, mouse models are available for a variety of diseases that enable testing of properties such as efficacy, toxicity, and pharmacokinetics for a given drug candidate. As is known in the art, cancer cells can be grafted or injected into mice to mimic a human cancer, a process referred to as xenografting. Testing of antibodies that comprise antibodies that are optimized for one or more mouse FcγRs, may provide valuable information with regard to the efficacy of the protein, its mechanism of action, and the like. The antibodies of the present invention may also be optimized for enhanced functionality and/or solution properties in aglycosylated form. In one embodiment, the aglycosylated antibodies of the present invention bind an Fc ligand with greater affinity than the aglycosylated form of the parent antibody. The Fc ligands include but are not limited to FcγRs, C1q, FcRn, and proteins A and G, and may be from any source including but not limited to human, mouse, rat, rabbit, or monkey. In an alternate embodiment, the antibodies are optimized to be more stable and/or more soluble than the aglycosylated form of the parent antibody.

Antibodies of the invention may comprise modifications that modulate interaction with Fc ligands other than FcγRs, including but not limited to complement proteins, FcRn, and Fc receptor homologs (FcRHs). FcRHs include but are not limited to FcRH1, FcRH2, FcRH3, FcRH4, FcRH5, and FcRH6 (Davis et ai, 2002, Immunol. Reviews 190:123-136).

Antibodies of the present invention may comprise one or more modifications that provide optimized properties that are not specifically related to effector function per se. The modifications may be amino acid modifications, or may be modifications that are made enzymatically or chemically. Such modification(s) likely provide some improvement in the antibody, for example an enhancement in its stability, solubility, function, or clinical use. The present invention contemplates a variety of improvements that made be made by coupling the antibodies of the present invention with additional modifications.

In one embodiment, the variable region of an antibody of the present invention may be affinity matured, that is to say that amino acid modifications have been made in the VH and/or VL domains of the antibody to enhance binding of the antibody to its target antigen. Such types of modifications may improve the association and/or the dissociation kinetics for binding to the target antigen. Other modifications include those that improve selectivity for target antigen vs. alternative targets. These include modifications that improve selectivity for antigen expressed on target vs non-target cells. Other improvements to the target recognition properties may be provided by additional modifications. Such properties may include, but are not limited to, specific kinetic properties (i.e. association and dissociation kinetics), selectivity for the particular target versus alternative targets, and selectivity for a specific form of target versus alternative forms. Examples include full-length versus splice variants, cell-surface vs. soluble forms, selectivity for various polymorphic variants, or selectivity for specific conformational forms of the target antigen.

Antibodies of the invention may comprise one or more modifications that provide reduced or enhanced internalization of an antibody. In one embodiment, antibodies of the present invention can be utilized or combined with additional modifications in order to reduce the cellular internalization of an antibody that occurs via interaction with one or more Fc ligands. This property might be expected to enhance effector function, and potentially reduce immunogenicity of the antibodies of the invention. Alternatively, antibodies of the present invention can be utilized directly or combined with additional modifications in order to enhance the cellular internalization of an antibody that occurs via interaction with one or more Fc ligands.

In one embodiment, modifications are made to improve biophysical properties of the antibodies of the present invention, including but not limited to stability, solubility, and oligomeric state. Modifications can include, for example, substitutions that provide more favorable intramolecular interactions in the antibody such as to provide greater stability, or substitution of exposed nonpolar amino acids with polar amino acids for higher solubility A number of optimization goals and methods are described in US patent application 2004-0110226, that may find use for engineering additional modifications to further optimize the antibodies of the present invention The antibodies of the present invention can also be combined with additional modifications that reduce oligomeric state or size, such that tumor penetration is enhanced, or in vivo clearance rates are increased as desired.

Other modifications to the antibodies of the present invention include those that enable the specific formation or homodimeric or homomultimeric molecules. Such modifications include but are not limited to engineered disulfides, as well as chemical modifications or aggregation methods which may provide a mechanism for generating covalent homodimeric or homomultimers. For example, methods of engineering and compositions of such molecules are described in Kan et al., 2001, J. Immunol., 2001, 166: 1320-1326; Stevenson et al., 2002, Recent Results Cancer Res. 159 104-12; U.S. Pat. No. 5,681,566; Caron et al., 1992, J. Exp. Med. 176:1191-1195, and Shopes, 1992, J. Immunol. 148(9): 2918-22. Additional modifications to the variants of the present invention include those that enable the specific formation or heterodimeric, heteromultimeric, bifunctional, and/or multifunctional molecules. Such modifications include, but are not limited to, one or more amino acid substitutions in the CH3 domain, in which the substitutions reduce homodimer formation and increase heterodimer formation. For example, methods of engineering and compositions of such molecules are described in Atwell et al., 1997, J. Mol. Biol. 270(1):26-35, and Carter et al., 2001, J. Immunol. Methods 248:7-15, each incorporated herein it its entirety by reference. Additional modifications include modifications in the hinge and CH3 domains, in which the modifications reduce the propensity to form dimers.

In further embodiments, the antibodies of the present invention comprise modifications that remove proteolytic degradation sites. These may include, for example, protease sites that reduce production yields, as well as protease sites that degrade the administered protein in vivo. In one embodiment, additional modifications are made to remove covalent degradation sites such as deamidation (i.e. deamidation of glutaminyl and asparaginyl residues to the corresponding glutamyl and aspartyl residues), oxidation, and proteolytic degradation sites. Deamidation sites that are particularly useful to remove are those that have enhance propensity for deamidation, including, but not limited to asparaginyl and glutamyl residues followed by glycines (NG and QG motifs, respectively). In such cases, substitution of either residue can significantly reduce the tendency for deamidation. Common oxidation sites include methionine and cysteine residues. Other covalent modifications, that can either be introduced or removed, include hydroxylation of proline and lysine, phosphorylation of hydroxyl groups of seryl or threonyl residues, methylation of the "-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group. Additional modifications also may include but are not limited to post-translational modifications such as N-linked or O-linked glycosylation and phosphorylation.

Modifications may include those that improve expression and/or purification yields from hosts or host cells commonly used for production of biologies. These include, but are not limited to various mammalian cell lines (e.g. CHO), yeast cell lines, bacterial cell lines, and plants. Additional modifications include modifications that remove or reduce the ability of heavy chains to form inter-chain disulfide linkages. Additional modifications include modifications that remove or reduce the ability of heavy chains to form intra-chain disulfide linkages.

The antibodies of the present invention may comprise modifications that include the use of unnatural amino acids incorporated using, for example, the technologies developed by Schultz and colleagues, including but not limited to methods described by Cropp & Shultz, 2004, Trends Genet. 20(12):625-30, Anderson et al., 2004, Proc. Natl. Acad. Sci. U.S.A. 101 (2):7566-71, Zhang et al., 2003, 303(5656):371-3, and Chin et al., 2003, Science 301(5635):964-7. In some embodiments, these modifications enable manipulation of various functional, biophysical, immunological, or manufacturing properties discussed above. In additional embodiments, these modifications enable additional chemical modification for other purposes. Other modifications are contemplated herein. For example, the antibody may be linked to one of a variety of nonproteinaceous polymers, e.g., polyethylene glycol (PEG), polypropylene glycol, polyoxyalkylenes, or copolymers of polyethylene glycol and polypropylene glycol. Additional amino acid modifications may be made to enable specific or non-specific chemical or posttranslational modification of the antibodies. Such modifications, include, but are not limited to PEGylation and glycosylation. Specific substitutions that can be utilized to enable PEGylation include, but are not limited to, introduction of novel cysteine residues or unnatural amino acids such that efficient and specific coupling chemistries can be used to attach a PEG or otherwise polymeric moiety. Introduction of specific glycosylation sites can be achieved by introducing novel N-X-T/S sequences into the antibodies of the present invention.

Covalent modifications of antibodies are included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

In some embodiments, the covalent modification of the antibodies of the invention comprises the addition of one or more labels. The term "labeling group" is any detectable label. In some embodiments, the labeling group is coupled to the antibody via spacer arms of various lengths to reduce potential steric hindrance. Various methods for labeling proteins are known in the art and may be used in performing the present invention. In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, [beta]-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labeling group is coupled to the antibody via spacer arms of various lengths to reduce potential steric hindrance. Various methods for labeling proteins are known in the art and may be used in performing the present invention. Specific labels include optical dyes, including, but not limited to, chromophores, phosphors and fluorophores, with the latter being specific in many instances. Fluorophores can be either "small molecule" fluores, or proteinaceous fluores. By "fluorescent label" is meant any molecule that may be detected via its inherent fluorescent properties.

In one embodiment, the antibodies of the invention are antibody "fusion proteins", sometimes referred to herein as "antibody conjugates". The fusion partner or conjugate partner can be proteinaceous or non-proteinaceous; the latter generally being generated using functional groups on the antibody and on the conjugate partner. Conjugate and fusion partners may be any molecule, including small molecule chemical compounds and polypeptides. For example, a variety of antibody conjugates and methods are described in Trail et al., 1999, Curr. Opin. Immunol. 11:584-588. Possible conjugate partners include but are not limited to cytokines, cytotoxic agents, toxins, radioisotopes, chemotherapeutic agent, anti-angiogenic agents, a tyrosine kinase inhibitors, and other therapeutically active agents. In some embodiments, conjugate partners may be thought of more as payloads, that is to say that the goal of a conjugate is targeted delivery of the conjugate partner to a targeted cell, for example a cancer cell or immune cell, by the antibody. Thus, for example, the conjugation of a toxin to an antibody targets the delivery of the toxin to cells expressing the target antigen. As will be appreciated by one skilled in the art, in reality the concepts and definitions of fusion and conjugate are overlapping. The designation of an antibody as a fusion or conjugate is not meant to constrain it to any particular embodiment of the present invention. Rather, these terms are used loosely to convey the broad concept that any antibody of the present invention may be linked genetically, chemically, or otherwise, to one or more polypeptides or molecules to provide some desirable property.

Suitable conjugates include, but are not limited to, labels as described below, drugs and cytotoxic agents including, but not limited to, cytotoxic drugs (e.g., chemotherapeutic agents) or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies, or binding of a radionuclide to a chelating agent that has been covalently attached to the antibody. Additional embodiments utilize calicheamicin, aunstatins, geldanamycin, maytansine, and duocarmycins and analogs; for the latter, see U.S. patent application 2003/0050331.

In one embodiment, the antibodies of the present invention are fused or conjugated to a cytokine. By "cytokine" as used herein is meant a generic term for proteins released by one cell population that act on another cell as intercellular mediators. For example, as described in Penichet et al., 2001, J Immunol Methods 248-91-101, cytokines may be fused to antibody to provide an array of desirable properties Examples of such cytokines are lymphokines, monokines, and traditional polypeptide hormones. Included among the cytokines are growth hormone such as human growth hormone, N-methionyl human growth hormone, and bovine growth hormone; parathyroid hormone, thyroxine; insulin; proinsuhn; relaxin, prorelaxin; glycoprotein hormones such as follicle stimulating hormone (FSH), thyroid stimulating hormone (TSH), and luteinizing hormone (LH); hepatic growth factor; fibroblast growth factor, prolactin, placental lactogen; tumor necrosis factor-alpha and -beta; mulle[pi]an-inhibiting substance, mouse gonadotropin-associated peptide; inhibin; activin, vascular endothelial growth factor; integrin; thrombopoietin (TPO); nerve growth factors such as NGF-beta; platelet-growth factor, transforming growth factors (TGFs) such as TGF-alpha and TGF-beta; insulin-like growth factor-1 and -II; erythropoietin (EPO); osteoinductive factors, interferons such as interferon-alpha, beta, and -gamma; colony stimulating factors (CSFs) such as macrophage-CSF (M-CSF), granulocyte-macrophage-CSF (GM-CSF); and granulocyte-CSF (G-CSF), interleukins (ILs) such as IL-1, IL-1alpha, IL-2, IL-3, IL-4, IL-5, IL-6, IL-7, IL-8, IL-9, IL-10, IL-11, IL-12, IL-15, a tumor necrosis factor such as TNF-alpha or TNF-beta; C5a; and other polypeptide factors including LIF and kit ligand (KL). As used herein, the term cytokine includes proteins from natural sources or from recombinant cell culture, and biologically active equivalents of the native sequence cytokines.

In an alternate embodiment, the antibodies of the present invention are fused, conjugated, or operably linked to a toxin, including but not limited to small molecule toxins and enzymatically active toxins of bacterial, fungal, plant or animal origin, including fragments and/or variants thereof. For example, a variety of immunotoxins and immunotoxin methods are described in Thrush et al., 1996, Ann. Rev. Immunol. 14:49-71. Small molecule toxins include but are not limited to calicheamicin, maytansine (U.S. Pat. No. 5,208,020), trichothene, and CC1065. In one embodiment of the invention, the antibody is conjugated to one or more maytansine molecules (e g about 1 to about 10 maytansine molecules per antibody molecule). Maytansine may, for example, be converted to May-SS-Me which may be reduced to May-SH3 and reacted with modified antibody (Chan et al., 1992, Cancer Research 52 127-131) to generate a maytansinoid-antibody conjugate Another conjugate of interest comprises an antibody conjugated to one or more calicheamicin molecules. The calicheamicin family of antibiotics is capable of producing double-stranded DNA breaks at sub-picomolar concentrations. Structural analogues of calicheamicin that may be used include are, for example, disclosed in Hinman et al., 1993, Cancer Research 53 3336-3342, Lode et al, 1998, Cancer Research 58 2925-2928, U.S. Pat. No. 5,714,586; U.S. Pat. No. 5,712,374, U.S. Pat. No. 5,264,586; and U.S. Pat. No. 5,773,001. Dolastatin 10 analogs such as auristatin E (AE) and monomethylauristatin E (MMAE) may find use as conjugates for the antibodies of the present invention (Doronina et al., 2003, Nat Biotechnol 21(7):778-84; Francisco et al., 2003 Blood 102(4):1458-65). Useful enzymatically active toxins include but are not limited to diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, PCT WO 93/21232. The present invention further contemplates a conjugate between an antibody of the present invention and a compound with nucleolytic activity, for example a ribonuclease or DNA endonuclease such as a deoxyribonuclease (DNase).

In an alternate embodiment, an antibody of the present invention may be fused, conjugated, or operably linked to a radioisotope to form a radioconjugate. A variety of radioactive isotopes are available for the production of radioconjugate antibodies. Examples include, but are not limited to, At211, I131, I125, Y90, Re186, Re188, Sm153, Bi212, P32, and radioactive isotopes of Lu.

In yet another embodiment, an antibody of the present invention may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the antibody is conjugated or operably linked to an enzyme in order to employ Antibody Dependent Enzyme Mediated Prodrug Therapy (ADEPT). ADEPT may be used by conjugating or operably linking the antibody to a prodrug-activating enzyme that converts a prodrug (e.g. a peptidyl chemotherapeutic agent, see PCT application WO 81/01145, incorporated herein it its entirety by reference) to an active anti-cancer drug. See, for example, PCT application WO 88/07378 or U.S. Pat. No. 4,975,278, each incorporated herein it its entirety by reference. The enzyme component of the immunoconjugate useful for ADEPT includes any enzyme capable of acting on a prodrug in such a way so as to covert it into its more active, cytotoxic form. Enzymes that are useful in the method of this invention include but are not limited to alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents, carbohydrate-cleaving enzymes such as beta-galactosidase and neuramimidase useful for converting glycosylated prodrugs into free drugs, beta-lactamase useful for converting drugs derivatized with alpha-lactams into free drugs, and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, for example, Massey, 1987, Nature 328. 457-458, incorporated herein it its entirety by reference). Antibody-abzyme conjugates can be prepared for delivery of the abzyme to a tumor cell population. A variety of additional conjugates are contemplated for the antibodies of the present invention. A variety of chemotherapeutic agents, anti-angiogenic agents, tyrosine kinase inhibitors, and other therapeutic agents are described below, which may find use as antibody conjugates.

Also contemplated as fusion and conjugate partners are Fc polypeptides. Thus an antibody may be a multimeric Fc polypeptide, comprising two or more Fc regions. The advantage of such a molecule is that it provides multiple binding sites for Fc receptors with a single protein molecule In one embodiment, Fc regions may be linked using a chemical engineering approach For example, Fab's and Fc's may be linked by thioether bonds originating at cysteine residues in the hinges, generating molecules such as $FabFc_2$. Fc regions may be linked using disulfide engineering and/or chemical cross-linking In one embodiment, Fc regions may be linked genetically. In one embodiment, Fc regions in an antibody are linked genetically to generated tandemly linked Fc regions as described in US patent application 2005-0249723, entitled "Fc polypeptides with novel Fc ligand binding sites". Tandemly linked Fc polypeptides may comprise two or more Fc regions, e.g., one to three, two, etc, Fc regions. It may be advantageous to explore a number of engineering constructs in order to obtain homo- or hetero-tandemly linked antibodies with the most favorable structural and functional properties. Tandemly linked antibodies may be homo-tandemly linked antibodies, that is an antibody of one isotype is fused genetically to another antibody of the same isotype. It is anticipated that because there are multiple FcγR, C1q, and/or FcRn binding sites on tandemly linked Fc polypeptides, effector functions and/or pharmacokinetics may be enhanced. In an alternate embodiment, antibodies from different isotypes may be tandemly linked, referred to as hetero-tandemly linked antibodies For example, because of the capacity to target FcγR and FcγR1 receptors, an antibody that binds both FcγRs and FcγRI may provide a significant clinical improvement.

Fusion and conjugate partners may be linked to any region of an antibody of the present invention, including at the N- or C-termini, or at some residue in-between the termini. In one embodiment, a fusion or conjugate partner is linked at the N- or C-terminus of the antibody, e g, the N-terminus. A variety of linkers may find use in the present invention to covalently link antibodies to a fusion or conjugate partner. By "linker", "linker sequence", "spacer", "tethering sequence" or grammatical equivalents thereof, herein is meant a molecule or group of molecules (such as a monomer or polymer) that connects two molecules and often serves to place the two molecules in a desirable configuration. Linkers are known in the art, for example, homo- or hetero-bifunctional linkers as are well known (see, 1994 Pierce Chemical Company catalog, technical section on cross-linkers, pages 155-200). A number of strategies may be used to covalently link molecules together. These include, but are not limited to polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis. The linker may contain amino acid residues that provide flexibility. Thus, the linker peptide may predominantly include the following amino acid residues Gly, Ser, Ala, or Thr. The linker peptide should have a length that is adequate to link two molecules in such a way that they assume the correct conformation relative to one another so that they retain the desired activity. Suitable lengths for this purpose include at least one and not more than 50 amino acid residues. In one embodiment, the linker is from about 1 to 30 amino acids in length, with linkers of 1 to 20 amino acids in length being desirable. Useful linkers include glycine-serine polymers (including, for example, (GS)n, (GSGGS)n (GGGGS)n and (GGGS)n, where n is an integer of at least one), glycine-alanine polymers, alanine-serine polymers, and other flexible linkers, as will be appreciated by those in the art. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use to link the antibodies of the present invention to a fusion or conjugate partner, or to link the antibodies of the present invention to a conjugate The present invention provides methods for producing and experimentally testing antibodies. The described methods are not meant to constrain the present invention to any particular application or theory of operation. Rather, the provided methods are meant to illustrate generally that one or more antibodies may be produced and experimentally tested to obtain variant antibodies. General methods for antibody molecular biology, expression, purification, and screening are described in Antibody Engineering, edited by Duebel & Kontermann, Springer-Verlag, Heidelberg, 2001, and Hayhurst & Georgiou, 2001, Curr Opin Chem Biol 5 683-689; Maynard & Georgiou, 2000, Annu Rev Biomed Eng 2 339-76, Antibodies. A Laboratory Manual by Harlow & Lane, New York: Cold Spring Harbor Laboratory Press, 1988.

In one embodiment of the present invention, nucleic acids are created that encode the antibodies, and that may then be cloned into host cells, expressed and assayed, if desired. Thus, nucleic acids, and particularly DNA, may be made that encode each protein sequence. These practices are carried out using well-known procedures. For example, a variety of methods that may find use in the present invention are described in Molecular Cloning—A Laboratory Manual, $3^{rd}$ Ed. (Maniatis, Cold Spring Harbor Laboratory Press, New York, 2001), and Current Protocols in Molecular Biology (John Wiley & Sons). As will be appreciated by those skilled in the art, the generation of exact sequences for a library comprising a large number of sequences is potentially expensive and time consuming. By "library" herein is meant a set of variants in any form, including but not limited to a list of nucleic acid or amino acid sequences, a list of nucleic acid or ammo acid substitutions at variable positions, a physical library comprising nucleic acids that encode the library sequences, or a physical library comprising the variant proteins, either in purified or unpurified form. Accordingly, there are a variety of techniques that may be used to efficiently generate libraries of the present invention. Such methods that may find use in the present invention are described or referenced in U.S. Pat. No. 6,403,312; US patent application 2002-0048772, U.S. Pat. No. 7,315,786; US patent application 2003-0130827, PCT application WO 01/40091 or PCT application WO 02/25588. Such methods include but are not limited to gene assembly methods, PCR-based method and methods which use variations of PCR, ligase chain reaction-based methods, pooled oligo methods such as those used in synthetic shuffling, error-prone amplification methods and methods which use ohgos with random mutations, classical site-directed mutagenesis methods, cassette mutagenesis, and other amplification and gene synthesis methods. As is known in the art, there are a variety of commercially available kits and methods for gene assembly, mutagenesis, vector subcloning, and the like, and such commercial products find use in the present invention for generating nucleic acids that encode antibodies.

The antibodies of the present invention may be produced by culturing a host cell transformed with nucleic acid, e.g., an expression vector, containing nucleic acid encoding the antibodies, under the appropriate conditions to induce or cause expression of the protein. The conditions appropriate for expression will vary with the choice of the expression vector and the host cell, and will be easily ascertained by one skilled in the art through routine experimentation. A wide variety of appropriate host cells may be used, including but not limited to mammalian cells, bacteria, insect cells, and yeast. For example, a variety of cell lines that may find use in the present invention are described in the ATCC cell line catalog, available from the American Type Culture Collection.

In one embodiment, the antibodies are expressed in mammalian expression systems, including systems in which the expression constructs are introduced into the mammalian cells using virus such as retrovirus or adenovirus. Any mammalian cells may be used, e.g., human, mouse, rat, hamster, primate cells, etc. Suitable cells also include known research cells, including but not limited to Jurkat T cells, NIH3T3, CHO, BHK, COS, HEK293, PER C.6, HeLa, Sp2/0, NSO cells and variants thereof. In an alternate embodiment, library proteins are expressed in bacterial cells. Bacterial expression systems are well known in the art, and include *Escherichia coli (E. coli). Bacillus subtilis, Streptococcus cremoris*, and *Streptococcus lividans*. In alternate embodiments, antibodies are produced in insect cells (e g Sf21/Sf9) or yeast cells (e.g. *S. cerevisiae, Pichia*, etc.). In an alternate embodiment, antibodies are expressed in vitro using cell free translation systems. In vitro translation systems derived from both prokaryotic (e.g. *E. coli*) and eukaryotic (e.g. wheat germ, rabbit reticulocytes) cells are available and may be chosen based on the expression levels and functional properties of the protein of interest. For example, as appreciated by those skilled in the art, in vitro translation is required for some display technologies, for example ribosome display. In addition, the antibodies may be produced by chemical synthesis methods. Also transgenic expression systems both animal (e.g. cow, sheep or goat milk, embryonated hen's eggs, whole insect larvae, etc.) and plant (e.g. corn, tobacco, duckweed, etc.). The nucleic acids that encode the antibodies of the present invention may be incorporated into an expression vector in order to express the protein. A variety of expression vectors may be utilized for protein expression. Expression vectors may comprise self-replicating extra-chromosomal vectors or vectors which integrate into a host genome. Expression vectors are constructed to be compatible with the host cell type. Thus expression vectors which find use in the present invention include but are not limited to those which enable protein expression in mammalian cells, bacteria, insect cells, yeast, and in in vitro systems. As is known in the art, a variety of expression vectors are available, commercially or otherwise, that may find use in the present invention for expressing antibodies.

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. Generally, these expression vectors include transcriptional and translational regulatory nucleic acid operably linked to the nucleic acid encoding the antibody, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used.

Antibodies may be operably linked to a fusion partner to enable targeting of the expressed protein, purification, screening, display, and the like. Fusion partners may be linked to the antibody sequence via a linker sequence. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the ammo acid sequence GGGGS. A fusion partner may be a targeting or signal sequence that directs antibody and any associated fusion partners to a desired cellular location or to the extracellular media. As is known in the art, certain signaling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example H6 and H10 or other tags for use with Immobilized Metal Affinity Chromatography (IMAC) systems (e.g $Ni^{2+}$ affinity columns)), GST fusions, MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both. For example, an antibody may be purified using a His-tag by immobilizing it to a $Ni^{2+}$ affinity column, and then after purification the same His-tag may be used to immobilize the antibody to a $Ni^{2+}$ coated plate to perform an ELISA or other binding assay (as described below). A fusion partner may enable the use of a selection method to screen antibodies (see below). Fusion partners that enable a variety of selection methods are well-known in the art, and all of these find use in the present invention. For example, by fusing the members of an antibody library to the gene III protein, phage display can be employed (Kay et al., Phage display of peptides and proteins: a laboratory manual, Academic Press, San Diego, Calif., 1996; Lowman et al., 1991, Biochemistry 30: 10832-

10838; Smith, 1985, Science 228:1315-1317). Fusion partners may enable antibodies to be labeled. Alternatively, a fusion partner may bind to a specific sequence on the expression vector, enabling the fusion partner and associated antibody to be linked covalently or noncovalently with the nucleic acid that encodes them.

The methods of introducing exogenous nucleic acid into host cells are well known in the art, and will vary with the host cell used. Techniques include but are not limited to dextran-mediated transfection, calcium phosphate precipitation, calcium chloride treatment, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

In one embodiment, antibodies are purified or isolated after expression. Proteins may be isolated or purified in a variety of ways known to those skilled in the art. Standard purification methods include chromatographic techniques, including ion exchange, hydrophobic interaction, affinity, sizing or get filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use in the present invention for purification of antibodies. For example, the bacterial proteins A and G bind to the Fc region. Likewise, the bacterial protein L binds to the Fab region of some antibodies, as of course does the antibody's target antigen. Purification can often be enabled by a particular fusion partner. For example, antibodies may be purified using glutathione resin if a GST fusion is employed, $Ni^{2+}$ affinity chromatography if a His-tag is employed, or immobilized anti-flag antibody if a flag-tag is used. For general guidance in suitable purification techniques, see, e.g. Protein Purification: Principles and Practice, $3^{rd}$ Ed., Scopes, Springer-Verlag, NY, 1994. The degree of purification necessary will vary depending on the screen or use of the antibodies. In some instances no purification is necessary. For example in one embodiment, if the antibodies are secreted, screening may take place directly from the media. As is well known in the art, some methods of selection do not involve purification of proteins. Thus, for example, if a library of antibodies is made into a phage display library, protein purification may not be performed.

Antibodies may be screened using a variety of methods, including but not limited to those that use in vitro assays, in vivo and cell-based assays, and selection technologies. Automation and high-throughput screening technologies may be utilized in the screening procedures. Screening may employ the use of a fusion partner or label. The use of fusion partners has been discussed above. By "labeled" herein is meant that the antibodies of the invention have one or more elements, isotopes, or chemical compounds attached to enable the detection in a screen. In general, labels fall into three classes: a) immune labels, which may be an epitope incorporated as a fusion partner that is recognized by an antibody, b) isotopic labels, which may be radioactive or heavy isotopes, and c) small molecule labels, which may include fluorescent and colorimetric dyes, or molecules such as biotin that enable other labeling methods. Labels may be incorporated into the compound at any position and may be incorporated in vitro or in vivo during protein expression.

In one embodiment, the functional and/or biophysical properties of antibodies are screened in an in vitro assay. In vitro assays may allow a broad dynamic range for screening properties of interest. Properties of antibodies that may be screened include but are not limited to stability, solubility, and affinity for Fc ligands, for example FcγRs. Multiple properties may be screened simultaneously or individually. Proteins may be purified or unpurified, depending on the requirements of the assay. In one embodiment, the screen is a qualitative or quantitative binding assay for binding of antibodies to a protein or nonprotein molecule that is known or thought to bind the antibody. In one embodiment, the screen is a binding assay for measuring binding to the target antigen. In an alternate embodiment, the screen is an assay for binding of antibodies to an Fc ligand, including but not limited to the family of FcγRs, the neonatal receptor FcRn, the complement protein C1q, and the bacterial proteins A and G. The Fc ligands may be from any organism, e.g., humans, mice, rats, rabbits, monkeys, etc. Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as Biacore™), isothermal titration calorimetry, differential scanning calorimetry, gel electrophoresis, and chromatography including gel filtration. These and other methods may take advantage of some fusion partner or label of the antibody. Assays may employ a variety of detection methods including but not limited to chromogenic, fluorescent, luminescent, or isotopic labels.

The biophysical properties of antibodies, for example stability and solubility, may be screened using a variety of methods known in the art. Protein stability may be determined by measuring the thermodynamic equilibrium between folded and unfolded states. For example, antibodies of the present invention may be unfolded using chemical denaturant, heat, or pH, and this transition may be monitored using methods including, but not limited to, circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of an antibody may be quantitatively or qualitatively determined using a wide range of methods that are known in the art. Methods which may find use in the present invention for characterizing the biophysical properties of antibodies include gel electrophoresis, isoelectric focusing, capillary electrophoresis, chromatography such as size exclusion chromatography, ion-exchange chromatography, and reversed-phase high performance liquid chromatography, peptide mapping, oligosaccharide mapping, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use. In one embodiment, stability and/or solubility may be measured by determining the amount of protein solution after some defined period of time. In this assay, the protein may or may not be exposed to some extreme condition, for example elevated temperature, low pH, or the presence of denaturant. Because function typically requires a stable, soluble, and/or well-folded/structured protein, the aforementioned functional and binding assays also provide ways to perform such a measurement. For example, a solution comprising an antibody could be assayed for its ability to bind target antigen, then exposed to elevated temperature for one or more defined periods of time, then assayed for antigen binding again. Because unfolded and aggregated protein is not expected to be capable of binding antigen, the amount of activity remaining provides a measure of the antibody's stability and solubility.

The biological properties of the antibodies of the present invention may be characterized in cell, tissue, and whole organism experiments. As is known in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. The animals may be referred to as disease models. With respect to the antibodies of the present invention, a particular challenge arises when using animal models to evaluate the potential for in-human efficacy of candidate polypeptides—this is due, at least in part, to the fact that antibodies that have a specific effect on the affinity for a human Fc receptor may not have a similar affinity effect with the orthologous animal receptor. These problems can be further exacerbated by the inevitable ambiguities associated with correct assignment of true orthologs (Mechetina et al., Immunogenetics, 2002 54:463-468), and the fact that some orthologs simply do not exist in the animal (e.g. humans possess an FcγRIIa whereas mice do not). Therapeutics are often tested in mice, including but not limited to nude mice, SCID mice, xenograft mice, and transgenic mice (including knockins and knockouts). For example, an antibody of the present invention that is intended as an anti-cancer therapeutic may be tested in a mouse cancer model, for example a xenograft mouse. In this method, a tumor or tumor cell line is grafted onto or injected into a mouse, and subsequently the mouse is treated with the therapeutic to determine the ability of the antibody to reduce or inhibit cancer growth and metastasis. An alternative approach is the use of a SCID murine model in which immune-deficient mice are injected with human Peripheral Blood Lymphocytes (PBLs), conferring a semi-functional and human immune system—with an appropriate array of human FcRs—to the mice that have subsequently been injected with antibodies or Fc-polypeptides that target injected human tumor cells. In such a model, the Fc-polypeptides that target the desired antigen interact with human PBLs within the mice to engage tumoricidal effector functions. Such experimentation may provide meaningful data for determination of the potential of the antibody to be used as a therapeutic. Any organism, e.g., mammals, may be used for testing. For example because of their genetic similarity to humans, monkeys can be suitable therapeutic models, and thus may be used to test the efficacy, toxicity, pharmacokinetics, or other property of the antibodies of the present invention. Tests of the antibodies of the present invention in humans are ultimately required for approval as drugs, and thus of course these experiments are contemplated. Thus the antibodies of the present invention may be tested in humans to determine their therapeutic efficacy, toxicity, pharmacokinetics, and/or other clinical properties.

Toxicity studies are performed to determine the antibody or Fc-fusion related-effects that cannot be evaluated in standard pharmacology profile or occur only after repeated administration of the agent. Most toxicity tests are performed in two species—a rodent and a non-rodent—to ensure that any unexpected adverse effects are not overlooked before new therapeutic entities are introduced into man. In general, these models may measure a variety of toxicities including genotoxicity, chronic toxicity, immunogenicity, reproductive/developmental toxicity, and carcinogenicity. Included within the aforementioned parameters are standard measurement of food consumption, bodyweight, antibody formation, clinical chemistry, and macro- and microscopic examination of standard organs/tissues (e g cardiotoxicity). Additional parameters of measurement are injection site trauma and the measurement of neutralizing antibodies, if any. Traditionally, monoclonal antibody therapeutics, naked or conjugated are evaluated for cross-reactivity with normal tissues, immunogenicity/antibody production, conjugate or linker toxicity and 'bystander' toxicity of radiolabeled species. Nonetheless, such studies may have to be individualized to address specific concerns and following the guidance set by ICH S6 (Safety studies for biotechnological products also noted above). As such, the general principles are that the products are sufficiently well characterized and for which impurities/contaminants have been removed, that the test material is comparable throughout development, and GLP compliance.

The pharmacokinetics (PK) of the antibodies of the invention can be studied in a variety of animal systems, with the most relevant being non-human primates such as the cynomolgous and rhesus monkeys. Single or repeated i.v./s.c. administrations over a dose range of 6000-fold (0.05-300 mg/kg) can be evaluated for the half-life (days to weeks) using plasma concentration and clearance as well as volume of distribution at a steady state and level of systemic absorbance can be measured. Examples of such parameters of measurement generally include maximum observed plasma concentration ($C_{max}$), the time to reach $C_{max}(T_{max})$, the area under the plasma concentration-time curve from time 0 to infinity [$AUC_{0-inf}$] and apparent elimination half-life ($T_{1/2}$). Additional measured parameters could include compartmental analysis of concentration-time data obtained following i.v. administration and bioavailability. Examples of pharmacological/toxicological studies using cynomolgus have been established for Rituxan® and Zevalm® in which monoclonal antibodies to CD20 are cross-reactive. Biodistribution, dosimetry (for radiolabled antibodies), and PK studies can also be done in rodent models. Such studies would evaluate tolerance at all doses administered, toxicity to local tissues, localization to rodent xenograft animal models, depletion of target cells. The antibodies of the present invention may confer superior pharmacokinetics in animal systems or in humans. For example, increased binding to FcRn may increase the half-life and exposure of the therapeutic antibody. Alternatively, decreased binding to FcRn may decrease the half-life and exposure of the Fc-containing drug in cases where reduced exposure is favorable such as when such drug has side effects. It is known in the art that the array of Fc receptors is differentially expressed on various immune cell types, as well as in different tissues. Differential tissue distribution of Fc receptors may ultimately have an impact on the pharmacodynamic (PD) and pharmacokinetic (PK) properties of antibodies of the present invention. Because antibodies of the presentation have varying affinities for the array of Fc receptors, further screening of the polypeptides for PD and/or PK properties may be extremely useful for defining the optimal balance of PD, PK, and therapeutic efficacy conferred by each candidate polypeptide.

Pharmacodynamic studies may include, but are not limited to, targeting specific tumor cells or blocking signaling mechanisms, measuring depletion of target antigen expressing cells or signals, etc. Such pharmacodynamic effects may be demonstrated in animal models or in humans.

The antibodies of the present invention may be used for therapeutic purposes. As will be appreciated by those in the art, the antibodies of the present invention may be used for any therapeutic purpose that uses antibodies and the like. In one embodiment, the antibodies are administered to a patient to treat disorders including but not limited to cancer.

A "patient" for the purposes of the present invention includes both humans and other animals, e.g., mammals, e.g., humans. Thus the antibodies of the present invention have both human therapy and veterinary applications. The term "treatment" or "treating" in the present invention is meant to include therapeutic treatment, as well as prophylactic, or suppressive measures for a disease or disorder Thus, for example, successful administration of an antibody prior to onset of the disease results in treatment of the disease. As another example, successful administration of an optimized antibody after clinical manifestation of the disease to combat the symptoms of the disease comprises treatment of the disease. "Treatment" and "treating" also encompasses administration of an optimized antibody after the appearance of the disease in order to eradicate the disease. Successful administration of an agent after onset and after clinical symptoms has developed, with possible abatement of clinical symptoms and perhaps amelioration of the disease, comprises treatment of the disease. Those "in need of treatment" include mammals already having the disease or disorder, as well as those prone to having the disease or disorder, including those in which the disease or disorder is to be prevented.

In one embodiment, an antibody of the present invention is administered to a patient having a disease involving inappropriate expression of a protein or other molecule, such as FLT3. Within the scope of the present invention this is meant to include diseases and disorders characterized by aberrant proteins, due for example to alterations in the amount of a protein present, protein localization, posttranslational modification, conformational state, the presence of a mutant protein, etc. An overabundance may be due to any cause, including but not limited to overexpression at the molecular level, prolonged or accumulated appearance at the site of action, or increased activity of a protein relative to normal. Included within this definition are diseases and disorders characterized by a reduction of a protein. This reduction may be due to any cause, including but not limited to reduced expression at the molecular level, shortened or reduced appearance at the site of action, mutant forms of a protein, or decreased activity of a protein relative to normal. Such an overabundance or reduction of a protein can be measured relative to normal expression, appearance, or activity of a protein, and the measurement may play an important role in the development and/or clinical testing of the antibodies of the present invention.

By "cancer" and "cancerous" herein refer to or describe the physiological condition in mammals that is typically characterized by unregulated cell growth. Examples of cancer include but are not limited to carcinoma, lymphoma, blastoma, sarcoma (including liposarcoma), neuroendocrine tumors, mesothelioma, schwanoma, meningioma, adenocarcinoma, melanoma, and leukemia or lymphoid malignancies.

More particular examples of such cancers include hematologic malignancies, such as non-Hodgkin's lymphomas (NHL), B-cell acute lymphoblastic leukemia/lymphoma (B-ALL), and T-cell acute lymphoblastic leukemia/lymphoma (T-ALL), thymoma, Langerhans cell histocytosis, multiple myeloma (MM), myeloid neoplasias such as acute myelogenous leukemias (AML), including AML with maturation, AML without differentiation, acute promyelocytic leukemia, acute myelomonocytic leukemia, and acute monocytic leukemias, myelodysplastic syndromes, and chronic myeloproliferative disorders (MDS), including chronic myelogenous leukemia (CML).

If the cancer or tumor is a lymphoma or leukemia, the disease may be in the stage of minimal residual disease (MRD). This stage may for example be reached after conventional chemotherapy with or without stem cell transplantation. In this context, "MRD" relates to a disease state where small numbers of lymphoma/leukaemic cells remain in the patient during treatment or after treatment when the patient is in remission, including complete remission (no symptoms or signs of disease). This is the major cause of relapse in cancer and leukaemia. In this stage, although the patient may be in complete remission, the disease is still detectable by state of the art techniques such as polymerase chain reaction (PCR) and flow cytometry (FACS).

The target of the antibodies of the present invention may be polymorphic in the human population. For a given patient or population of patients, the efficacy of the antibodies of the present invention may thus be affected by the presence or absence of specific polymorphisms in proteins. For example, FcγRIIIA is polymorphic at position 158, which is commonly either V (high affinity) or F (low affinity). Patients with the V/V homozygous genotype are observed to have a better clinical response to treatment with the anti-CD20 antibody Rituxan® (rituximab), likely because these patients mount a stronger NK response (Dall'Ozzo et al. (2004) Cancer Res. 64-4664-9). Additional polymorphisms include but are not limited to FcγRIIA R131 or H131, and such polymorphisms are known to either increase or decrease Fc binding and subsequent biological activity, depending on the polymorphism. Antibodies of the present invention may bind to a particular polymorphic form of a receptor, for example FcγRIIIA 158V, or to bind with equivalent affinity to all of the polymorphisms at a particular position in the receptor, for example both the 158V and 158F polymorphisms of FcγRIIIA. In one embodiment, antibodies of the present invention may have equivalent binding to polymorphisms that may be used in an antibody to eliminate the differential efficacy seen in patients with different polymorphisms. Such a property may give greater consistency in therapeutic response and reduce non-responding patient populations. Such variant Fc with identical binding to receptor polymorphisms may have increased biological activity, such as ADCC, CDC or circulating half-life, or alternatively decreased activity, via modulation of the binding to the relevant Fc receptors. In one embodiment, antibodies of the present invention may bind with higher or lower affinity to one of the polymorphisms of a receptor, either accentuating the existing difference in binding or reversing the difference. Such a property may allow creation of therapeutics particularly tailored for efficacy with a patient population possessing such polymorphism. For example, a patient population possessing a polymorphism with a higher affinity for an inhibitory receptor such as FcγRIIb could receive a drug containing an antibody with reduced binding to such polymorphic form of the receptor, creating a more efficacious drug.

In one embodiment, patients are screened for one or more polymorphisms in order to predict the efficacy of the antibodies of the present invention. This information may be used, for example, to select patients to include or exclude from clinical trials or, post-approval, to provide guidance to physicians and patients regarding appropriate dosages and treatment options. In one embodiment, patients are selected for inclusion in clinical trials for an antibody of the present invention if their genotype indicates that they are likely to respond significantly better to an antibody of the present invention as compared to one or more currently used antibody therapeutics. In another embodiment, appropriate dosages and treatment regimens are determined using such genotype information. In another embodiment, patients are selected for inclusion in a clinical trial or for receipt of therapy post-approval based on their polymorphism genotype, where such therapy contains an antibody engineered to be specifically efficacious for such population, or alternatively where such therapy contains an antibody that does not show differential activity to the different forms of the polymorphism.

Included in the present invention are diagnostic tests to identify patients who are likely to show a favorable clinical response to an antibody of the present invention, or who are likely to exhibit a significantly better response when treated with an antibody of the present invention versus one or more currently used antibody therapeutics. Any of a number of methods for determining FcγR polymorphisms in humans known in the art may be used.

Furthermore, the present invention comprises prognostic tests performed on clinical samples such as blood and tissue samples. Such tests may assay for effector function activity, including but not limited to ADCC, CDC, phagocytosis, and opsonization, or for killing, regardless of mechanism, of cancerous or otherwise pathogenic cells. In one embodiment, ADCC assays, such as those described previously, are used to predict, for a specific patient, the efficacy of a given antibody of the present invention. Such information may be used to identify patients for inclusion or exclusion in clinical trials, or to inform decisions regarding appropriate dosages and treatment regimens. Such information may also be used to select a drug that contains a particular antibody that shows superior activity in such assay.

Pharmaceutical compositions are contemplated wherein an antibody of the present invention and one or more therapeutically active agents are formulated. Formulations of the antibodies of the present invention are prepared for storage by mixing the antibody having the desired degree of purity with optional pharmaceutically acceptable carriers, excipients or stabilizers (Remington's Pharmaceutical Sciences 16th edition, Osol, A. Ed., 1980), in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants such as TWEEN™, PLURONICS™ or polyethylene glycol (PEG). In one embodiment, the pharmaceutical composition that comprises the antibody of the present invention may be in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly useful are the ammonium, potassium, sodium, calcium, and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration should be sterile. This is readily accomplished by filtration through sterile filtration membranes or other methods.

The antibodies disclosed herein may also be formulated as immunoliposomes. A liposome is a small vesicle comprising various types of lipids, phospholipids and/or surfactant that is useful for delivery of a therapeutic agent to a mammal. Liposomes containing the antibody are prepared by methods known in the art, such as described in Epstein et al., 1985, Proc Natl Acad Sci USA, 82:3688; Hwang et al., 1980, Proc Natl Acad Sci USA, 77:4030; U.S. Pat. No. 4,485,045; U.S. Pat. No. 4,544,545; and PCT application WO 97/38731. Liposomes with enhanced circulation time are disclosed in U.S. Pat. No. 5,013,556. The components of the liposome are commonly arranged in a bilayer formation, similar to the lipid arrangement of biological membranes. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. A chemotherapeutic agent or other therapeutically active agent is optionally contained within the liposome (Gabizon et al., 1989, J National Cancer Inst 81:1484).

The antibody and other therapeutically active agents may also be entrapped in microcapsules prepared by methods including but not limited to coacervation techniques, interfacial polymerization (for example using hydroxymethylcellulose or gelatin-microcapsules, or poly-(methylmethacylate) microcapsules), colloidal drug delivery systems (for example, liposomes, albumin microspheres, microemulsions, nano-particles and nanocapsules), and macroemulsions. Such techniques are disclosed in Remington's Pharmaceutical Sciences 16th edition, Osol, A. Ed., 1980. Sustained-release preparations may be prepared. Suitable examples of sustained-release preparations include semipermeable matrices of solid hydrophobic polymer, which matrices are in the form of shaped articles, e.g. films, or microcapsules. Examples of sustained-release matrices include polyesters, hydrogels (for example poly(2-hydroxyethyl-methacrylate), or poly(vinylalcohol)), polylactides (U.S. Pat. No. 3,773,919), copolymers of L-glutamic acid and gamma ethyl-L-glutamate, non-degradable ethylene-vinyl acetate, degradable lactic acid-glycolic acid copolymers such as the Lupron Depot® (which are injectable microspheres composed of lactic acid-glycolic acid copolymer and leuprolide acetate), poly-D-(−)-3-hydroxybutyric acid, and ProLease® (commercially available from Alkermes), which is a microsphere-based delivery system composed of the desired bioactive molecule incorporated into a matrix of poly-DL-lactide-co-glycolide (PLG).

Administration of the pharmaceutical composition comprising an antibody of the present invention, e.g., in the form of a sterile aqueous solution, may be done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly. As is known in the art, the pharmaceutical composition may be formulated accordingly depending upon the manner of introduction.

As is known in the art, protein therapeutics are often delivered by IV infusion or bolus. The antibodies of the present invention may also be delivered using such methods. For example, administration may be by intravenous infusion with 0.9% sodium chloride as an infusion vehicle.

In addition, any of a number of delivery systems are known in the art and may be used to administer the antibodies of the present invention. Examples include, but are not limited to, encapsulation in liposomes, microparticles, microspheres (eg. PLA/PGA microspheres), and the like. Alternatively, an implant of a porous, non-porous, or gelatinous material, including membranes or fibers, may be used. Sustained release systems may comprise a polymeric material or matrix such as polyesters, hydrogels, poly(vinylalcohol), polylactides, copolymers of L-glutamic acid and ethyl-L-glutamate, ethylene-vinyl acetate, lactic acid-glycolic acid copolymers such as the Lupron Depot®, and poly-D-(−)-3-hydroxybutyric acid. It is also possible to administer a nucleic acid encoding the antibody of the current invention, for example by retroviral infection, direct injection, or coating with lipids, cell surface receptors, or other transfection agents. In all cases, controlled release systems may be used to release the antibody at or close to the desired location of action.

The dosing amounts and frequencies of administration are, in one embodiment, selected to be therapeutically or prophylactically effective. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

The concentration of the therapeutically active antibody in the formulation may vary from about 0.1 to 100 weight %. In one embodiment, the concentration of the antibody is in the range of 0.003 µM to 1.0 molar. In order to treat a patient, a therapeutically effective dose of the antibody of the present invention may be administered. By "therapeutically effective dose" herein is meant a dose that produces the effects for which it is administered. The exact dose will depend on the purpose of the treatment, and will be ascertainable by one skilled in the art using known techniques. Dosages may range from 0.0001 to 100 mg/kg of body weight or greater, for example 0.1, 1, 10, or 50 mg/kg of body weight, e.g., 1 to 10 mg/kg of body weight.

In some embodiments, only a single dose of the antibody is used. In other embodiments, multiple doses of the antibody are administered. The elapsed time between administrations may be less than 1 hour, about 1 hour, about 1-2 hours, about 2-3 hours, about 3-4 hours, about 6 hours, about 12 hours, about 24 hours, about 48 hours, about 2-4 days, about 4-6 days, about 1 week, about 2 weeks, or more than 2 weeks.

In other embodiments the antibodies of the present invention are administered in metronomic dosing regimes, either by continuous infusion or frequent administration without extended rest periods. Such metronomic administration may involve dosing at constant intervals without rest periods. Typically such regimens encompass chronic low-dose or continuous infusion for an extended period of time, for example 1-2 days, 1-2 weeks, 1-2 months, or up to 6 months or more. The use of lower doses may minimize side effects and the need for rest periods.

In certain embodiments the antibody of the present invention and one or more other prophylactic or therapeutic agents are cyclically administered to the patient. Cycling therapy involves administration of a first agent at one time, a second agent at a second time, optionally additional agents at additional times, optionally a rest period, and then repeating this sequence of administration one or more times. The number of cycles is typically from 2-10. Cycling therapy may reduce the development of resistance to one or more agents, may minimize side effects, or may improve treatment efficacy.

The antibodies of the present invention may be administered concomitantly with one or more other therapeutic regimens or agents. The additional therapeutic regimes or agents may be used to improve the efficacy or safety of the antibody. Also, the additional therapeutic regimes or agents may be used to treat the same disease or a comorbidity rather than to alter the action of the antibody. For example, an antibody of the present invention may be administered to the patient along with chemotherapy, radiation therapy, or both chemotherapy and radiation therapy. The antibody of the present invention may be administered in combination with one or more other prophylactic or therapeutic agents, including but not limited to cytotoxic agents, chemotherapeutic agents, cytokines, growth inhibitory agents, anti-hormonal agents, kinase inhibitors, anti-angiogenic agents, cardioprotectants, immunostimulatory agents, immunosuppressive agents, agents that promote proliferation of hematological cells, angiogenesis inhibitors, protein tyrosine kinase (PTK) inhibitors, additional antibodies, FcγRIIb or other Fc receptor inhibitors, or other therapeutic agents.

The terms "in combination with" and "co-administration" are not limited to the administration of the prophylactic or therapeutic agents at exactly the same time. Instead, it is meant that the antibody of the present invention and the other agent or agents are administered in a sequence and within a time interval such that they may act together to provide a benefit that is increased versus treatment with only either the antibody of the present invention or the other agent or agents. In one embodiment, that the antibody and the other agent or agents act additively, e.g., they act synergistically. Such molecules are suitably present in combination in amounts that are effective for the purpose intended. The skilled medical practitioner can determine empirically, or by considering the pharmacokinetics and modes of action of the agents, the appropriate dose or doses of each therapeutic agent, as well as the appropriate timings and methods of administration.

In one embodiment, the antibodies of the present invention are administered with one or more additional molecules comprising antibodies or Fc. The antibodies of the present invention may be co-administered with one or more other antibodies that have efficacy in treating the same disease or an additional comorbidity, for example two antibodies may be administered that recognize two antigens that are overexpressed in a given type of cancer.

In one embodiment, the antibodies of the present invention are administered with a chemotherapeutic agent. By "chemotherapeutic agent" as used herein is meant a chemical compound useful in the treatment of cancer. Examples of chemotherapeutic agents include but are not limited to alkylating agents such as thiotepa and cyclosphosphamide; alkyl sulfonates such as busulfan, improsulfan and piposulfan, androgens such as calusterone, dromostanolone propionate, epitiostanol, mepitiostane, testolactone, anti-adrenals such as aminoglutethimide, mitotane, trilostane, anti-androgens such as flutamide, nilutamide, bicalutamide, leuprolide, and goserelin; antibiotics such as aclacinomysins, actinomycin, authramycin, azasenne, bleomycins, cactinomycin, calicheamicin, carabicin, caminomycin, carzinophilm, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, etreptozocin, tubercidin, ubenimex, zinostatin, zorubicin; anti estrogens including for example tamoxifen, raloxifene, aromatase inhibiting 4(5)-imidazoles, 4-hydroxytamoxifen, trioxifene, keoxifene, LY 117018, onapristone, and toremifene (Fareston); anti-metabolites such as methotrexate and 5-fluorouracil (5-FU); folic acid analogues such as denopterin, methotrexate, pteropterin, trimetrexate; aziridines such as benzodopa, carboquone, meturedopa, and uredopa; ethylenimines and methylamelamines including altretamine, triethylenemelamine, trietylenephosphoramide, thethylenethiophosphaoramide and trimethylolomelamine; folic acid replenisher such as frolinic acid; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; platinum analogs such as cisplatin and carboplatin; vinblastine; platinum; proteins such as arginine deiminase and asparaginase; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; taxanes, e.g. paclitaxel (TAXOL®, Bristol-Myers Squibb Oncology, Princeton, N.J.) and docetaxel (TAXOTERE®, Rhne-Poulenc Rorer, Antony, France); topoisomerase inhibitor RFS 2000; thymidylate synthase inhibitor (such as Tomudex); additional chemotherapeutics including aceglatone; aldophosphamide glycoside; aminolevulinic acid; amsacrine; bestrabucil; bisantrene; edatraxate; defofamine; demecolcine; diaziquone; difluoromethylornithine (DMFO); elformithine; elliptinium acetate; etoglucid; gallium nitrate; hydroxyurea; lentinan; Ionidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; chlorambucil; gemcitabine; 6-thioguanine; mercaptopurine; methotrexate; etoposide (VP-16); ifosfamide; mitomycin C; mitoxantrone; vincristine; vinorelbine; navelbine; novantrone; teniposide; daunomycin; aminopterin; xeloda; ibandronate; CPT-11; retinoic acid; esperamicins; capecitabine. Pharmaceutically acceptable salts, acids, or derivatives of any of the above may also be used.

A chemotherapeutic or other cytotoxic agent may be administered as a prodrug. By "prodrug" as used herein is meant a precursor or derivative form of a pharmaceutically active substance that is less cytotoxic to tumor cells compared to the parent drug and is capable of being enzymatically activated or converted into the more active parent form. See, for example Wilman, 1986, Biochemical Society Transactions, 615th Meeting Belfast, 14:375-382; Stella et al., "Prodrugs: A Chemical Approach to Targeted Drug Delivery," Directed Drug Delivery; and Borchardt et al., (ed.): 247-267, Humana Press, 1985. The prodrugs that may find use with the present invention include but are not limited to phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use with the antibodies of the present invention include but are not limited to any of the aforementioned chemotherapeutic agents.

In another embodiment, the antibody is administered with one or more immunomodulatory agents. Such agents may increase or decrease production of one or more cytokines, up- or down-regulate self-antigen presentation, mask MHC antigens, or promote the proliferation, differentiation, migration, or activation state of one or more types of immune cells. Immunomodulatory agents include but are not limited to non-steroidal anti-inflammatory drugs (NSAIDs) such as aspirin, ibuprofen, celecoxib, diclofenac, etodolac, fenoprofen, indomethacin, ketorolac, oxaprozin, nabumentone, sulindac, tolmentin, rofecoxib, naproxen, ketoprofen, and nabumetone, steroids (e.g. glucocorticoids, dexamethasone, cortisone, hydroxycortisone, methylprednisolone, prednisone, prednisolone, trimcinolone, azulfidineicosanoids such as prostaglandins, thromboxanes, and leukotrienes, as well as topical steroids such as anthrahn, calcipotriene, clobetasol, and tazarotene), cytokines such as TGFb, IFNα, IFNβ, IFNγ, IL-2, IL-4, IL-10, cytokine, chemokine, or receptor antagonists including antibodies, soluble receptors, and receptor-Fc fusions against BAFF, B7, CCR2, CCR5, CD2, CD3, CD4, CD6, CD7, CD8, CD11, CD14, CD15, CD17, CD18, CD20, CD23, CD28, CD40, CD40L, CD44, CD45, CD402, CD64, CD80, CD86, CD147, CD152, complement factors (C5, D) CTLA4, eotaxin, Fas, ICAM, ICOS, IFNα, IFNβ, IFNγ, IFNAR, IgE, IL-1, IL-2, IL-2R, IL-4, IL-5R, IL-6, IL-8, IL-9 IL-12, IL-13, IL-13R1, IL-15, IL-18R, IL-23, integrins, LFA-1, LFA-3, MHC, selectins, TGFβ, TNFα, TNFβ, TNF-R1, T-cell receptor, including Enbrel® (etanercept), Humira® (adalimumab), and Remicade® (infliximab), heterologous anti-lymphocyte globulin; other immunomodulatory molecules such as 2-amino-6-aryl-5 substituted pyrimidines, anti-idiotypic antibodies for MHC binding peptides and MHC fragments, azathioprine, brequinar, bromocryptine, cyclophosphamide, cyclosporine A, D-penicillamine, deoxyspergualm, FK506, glutaraldehyde, gold, hydroxychloroquine, leflunomide, malononitriloamides (e.g. leflunomide), methotrexate, minocycline, mizoribine, mycophenolate mofetil, rapamycin, and sulfasasazine.

In an alternate embodiment, antibodies of the present invention are administered with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone, thyroxine; insulin; proinsulin, relaxin, prorelaxin, glycoprotein hormones such as follicle stimulating hormone (FSH), thyroid stimulating hormone (TSH), and luteinizing hormone (LH), hepatic growth factor, fibroblast growth factor; prolactin, placental lactogen, tumor necrosis factor-alpha and -beta; mullerian-inhibiting substance, mouse gonadotropin-associated peptide, inhibin; activin, vascular endothelial growth factor; integrin; thrombopoietin (TPO); nerve growth factors such as NGF-beta; platelet-growth factor, transforming growth factors (TGFs) such as TGF-alpha and TGF-beta, insulin-like growth factor-1 and -II; erythropoietin (EPO), osteoinductive factors, interferons such as interferon-alpha, beta, and -gamma, colony stimulating factors (CSFs) such as macrophage-CSF (M-CSF), granulocyte-macrophage-CSF (GM-CSF), and granulocyte-CSF (G-CSF), interleukins (ILs) such as IL-1, IL-1 alpha, IL-2, IL-3, IL-4, IL-5, IL-6, IL-7, IL-8, IL-9, IL-10, IL-11, IL-12, IL-15, a tumor necrosis factor such as TNF-alpha or TNF-beta, and other polypeptide factors including LIF and kit ligand (KL) As used herein, the term cytokine includes proteins from natural sources or from recombinant cell culture, and biologically active equivalents of the native sequence cytokines.

In one embodiment, cytokines or other agents that stimulate cells of the immune system are co-administered with the antibody of the present invention. Such a mode of treatment may enhance desired effector function. For example, agents that stimulate NK cells, including but not limited to IL-2 may be co-administered. In another embodiment, agents that stimulate macrophages, including but not limited to C5a, formyl peptides such as N-formyl-methionyl-leucyl-phenylalanine (Beigier-Bompadre et al. (2003) Scand J. Immunol. 57. 221-8), may be co-administered Also, agents that stimulate neutrophils, including but not limited to G-CSF, GM-CSF, and the like may be administered Furthermore, agents that promote migration of such immunostimulatory cytokines may be used. Also additional agents including but not limited to interferon gamma, IL-3 and IL-7 may promote one or more effector functions.

In an alternate embodiment, cytokines or other agents that inhibit effector cell function are co-administered with the antibody of the present invention Such a mode of treatment may limit unwanted effector function The antibodies of the present invention may be combined with other therapeutic regimens. For example, in one embodiment, the patient to be treated with an antibody of the present invention may also receive radiation therapy. Radiation therapy can be administered according to protocols commonly employed in the art and known to the skilled artisan. Such therapy includes but is not limited to cesium, iridium, iodine, or cobalt radiation. The radiation therapy may be whole body irradiation, or may be directed locally to a specific site or tissue in or on the body, such as the lung, bladder, or prostate. Typically, radiation therapy is administered in pulses over a period of time from about 1 to 2 weeks. The radiation therapy may, however, be administered over longer periods of time. For instance, radiation therapy may be administered to patients having head and neck cancer for about 6 to about 7 weeks. Optionally, the radiation therapy may be administered as a single dose or as multiple, sequential doses. The skilled medical practitioner can determine empirically the appropriate dose or doses of radiation therapy useful herein. In accordance with another embodiment of the invention, the antibody of the present invention and one or more other anti-cancer therapies are employed to treat cancer cells ex vivo. It is contemplated that such ex vivo treatment may be useful in bone marrow transplantation and particularly, autologous bone marrow transplantation. For instance, treatment of cells or tissue(s) containing cancer cells with antibody and one or more other anti-cancer therapies, such as described above, can be employed to deplete or substantially deplete the cancer cells prior to transplantation in a recipient patient.

It is of course contemplated that the antibodies of the invention may employ in combination with still other therapeutic techniques such as surgery or phototherapy.

The present invention is further illustrated by the following examples. However, it should be understood, that the invention is not limited to the exemplified embodiments.

EXAMPLES

Materials and Methods

A. Bacterial Strains and Plasmids

*Escherichia coli* DH5a (Invitrogen, Karlsruhe, Germany) was used for the amplification of plasmids and cloning.

B. Cell Lines

Mouse myeloma cell line Sp2/0-Ag14 (ATCC, American Type Culture Collection, Manassas, Va., USA) used for production of recombinant hum-FLT3 specific antibody derivatives was cultured in IMDM (PAN-Biotech, Aidenbach, Germany) supplemented with 10% fetal calf serum (PAN-Biotech, Aidenbach, Germany), 1% penicillin and streptomycin (Lonza, Basel, Switzerland). Stable transfectants were selected with 1 mg/ml G418 (Invitrogen, Karlsruhe, Germany).

Hybridoma cell lines BV10 and 4G8, secreting mouse IgG1/κ anti human FLT3 specific antibodies (obtained from Dr. H-J. Bühring, UKT Tübingen, Germany), were cultured in RPMI 1640 (PAN-Biotech, Aidenbach, Germany) supplemented with 10% fetal calf serum (PAN-Biotech, Aidenbach, Germany), 1% penicillin and streptomycin (Lonza, Basel, Switzerland).

Peripheral blood mononuclear cells (PBMCs), isolated by density gradient centrifugation (LSM 1077, Lonza, Basel, Switzerland), hybridoma cells and NALM16 cells (kind gift of R. Handgretinger, Department of Pediatrics, University of Tübingen) were kept in RPMI 1640, mouse Sp2/0-Ag14 cells (ATCC, Manassas, USA) in IMDM medium (Lonza). All media were supplemented with 10% heat-inactivated fetal calf serum, 100 U/ml penicillin, 100 µg/ml streptomycin, 1 mM sodium-pyruvate, non-essential amino-acids, 2 mM L-glutamine and 57 nM beta-mercaptoethanol.

C. FLT3-Transfectant

Full length cDNA of human FLT3 (GenBank #BC126350) was obtained from ImaGenes, Berlin, Germany. The cDNA was cloned into the pcDNA3 vector using added BamHI- and XbaI-restriction sites and transfected into Sp2/0-Ag14 cells by electroporation.

D. Antibodies and Flow Cytometry

CD33-PE-Cy5 (clone WM53), CD34-APC (clone 581), CD-45-FITC (clone H130), CD123-PE-Cy5 (clone 9F5), CD11c-PE (clone B-ly6) and isotype control antibodies were purchased from BD Biosciences (Heidelberg, Germany), the CD303-FITC antibody from Miltenyi Biotech (Bergisch-Gladbach, Germany). All antibodies were incubated with cells for 30 minutes at 4° C. For indirect immunofluorescence, PE- or APC-conjugated goat-anti-mouse F(ab)2-fragments and goat-anti-human F(ab)2-fragments, respectively, were used (Jackson ImmunoResearch, West Grove, USA). In several experiments, we combined indirect and direct immunofluorescence for multi-dimensional analysis adding labeled antibodies in a final step. Cells were analyzed on a FACSCanto II or a FACSCalibur (Becton Dickinson). Beads for the quantitative analysis of indirect immunofluorescence (QIFIKIT®) were purchased from Dako (Hamburg, Germany) and used according to the protocol of the manufacturer. For quantification of humanized antibodies suitable beads were not available. Thus, a specific fluorescence index (SFI) was calculated by dividing mean fluorescence intensity obtained with 4G8SDIEM by that detected with the non binding, SDIE-modified control antibody 9.2.27. For these experiments PE conjugated antibodies generated with the Lynx rapid PE antibody conjugation kit (AbD Serotec, Düsseldorf, Germany) were used. Recombinant FLT3 ligand (rFLT3L) was purchased from Peprotech EC (London, Great Britain). For competition experiments various concentrations of rFLT3L were incubated with NALM16 cells and BV10SDIEM or 4G8SDIEM (1 µg/ml) for 30 minutes at 4° C. and analyzed by indirect immunofluorescence and flow cytometry.

E. 3[H]-Methyl-Thymidine Uptake Assay $2 \times 10^5$ AML blasts were seeded in triplicates in 96 well plates and incubated with various concentrations of optimized antibodies. After 24 hours cells were pulsed for another 20 hours with 3[H]-methyl-thymidine (0.5 µCi/well) and harvested on filtermats. Incorporated radioactivity was determined by liquid scintillation counting in a 2450 Microplate counter (Perkin Elmer, Waltham, USA).

F. 51[Cr]-Release Assays

NALM16 cells and primary AML blasts were used as targets. To separate blasts and effector cells from the PBMC preparations of leukemia patients, cells were labeled with CD34 and CD33 microbeads and separated on LD columns following the manufacturers (Miltenyi Biotec) protocol. The number of contaminating blast cells in the negatively selected effector cell population was determined by FACS analysis and varied between 1% and 10% depending on the initial blast contamination. In some experiments labeled DCs were used as target cells. Chromium release assays were performed as previously described (Otz T, Grosse-Hovest L, Hofmann M, Rammensee H G, Jung G. A bispecific singlechain antibody that mediates target cell-restricted, supra-agonistic CD28 stimulation and killing of lymphoma cells. *Leukemia.* 2009; 23(1):71-77). Briefly, labeled target cells and PBMCs were incubated at 37° C. for 4 or 8 hours in 96 well flat bottom plates in the presence of various concentrations of antibodies at a PBMC:target ratio of 50:1. Percentage of specific 51[Cr] release was calculated according to the formula [cpm (test)-cpm (spontaneous)/[cpm (triton lysis)]-cpm (spontaneous)]. If leukemic blasts were used as targets the addition of effector cells without antibody reduced spontaneous 51[Cr] release in some experiments resulting in negative values for the specific release.

G. Antigen Shift

NALM16 cells or AML blasts were incubated with various concentrations of 4G8SDIEM or BV10SDIEM in RPMI 1640 medium. After 24 or 48 hours the cells were washed with icecold FACS-buffer, incubated with a saturating concentration of 4G8SDIEM (2 µg/ml) for 30 minutes at 4° C., stained with PE-conjuagted goat-anti-human F(ab)2-fragments and analyzed by FACS. Relative surface expression of FLT3 was calculated defining the mean fluorescence intensity of cells preincubated without antibody as 100%.

H. Dendritic Cell (DC) Isolation and -Maturation

DCs were isolated from buffy coat preparations of healthy individuals using the blood DC isolation kit II according to the protocol of the manufacturer (Miltenyi Biotec). Myeloid (mDC) and plasmacytoid (pDC) subsets were stained with a mixture of CD11c-PE, CD303-FITC and CD 123-PE-Cy5 antibodies. For in vitro generation of mDC, 1×108 PBMCs of healthy individuals were seeded in 10 ml X-Vivo15 medium (Gibco, Darmstadt, Germany). After 2 hours at 37° C. adherent cells were cultured in RPMI 1640 medium supplemented with 50 ng/ml GM-CSF and IL-4 (20 ng/ml) for 5 days. On day 6 LPS (100 ng/ml) was added. Cells were harvested on day 7 and analyzed by flow cytometry.

I. Colony Forming Unit Assay

Bone marrow cells were obtained by lavage of the femoral head from patients undergoing hip surgery. The cells were purified by density gradient centrifugation and seeded at 107/ml in RPMI 1640 medium containing 5 µg/ml of 4G8SDIEM or 9.2.27SDIE. After 24 hours of incubation cells were transferred into antibody containing (5 µg/ml) methylcellulose medium (10.000 cells/ml, MethoCult H4434 classic, Stemcell Technologies, Grenoble, France). The assay was performed in triplicates. After 12 days colonies were counted and classified.

Example 1

Identification of Unknown Sequences from FLT3 Specific Antibodies

A. Cloning of the DNA Encoding V Regions

The cloning of the V regions was done by PCR. Most techniques start from mRNA and make use of the similarity of antibody V regions (Kabat, E. A., Wu, T. T., Reid-Müller, M., Perry, H. M., Gottesman, K. S. Sequences of Proteins of immunological interest, 4th ed. U.S. Department of Health and Human Services, Public Health Service, National Institute of Health, Bethesda, Md. 1987) which makes the design of degenerated primers for PCR amplification possible (Larrick, J. W., Daniellson, L., Brenner, C. A., Wallace, E. F., Abrahamson, M., Fry, K. E., Borrebaeck, C. A. K. Polymerase chain reaction used mixed primers: cloning of a human monoclonal antibody variable region genes from single hybridoma cells. Bio/Technology 7: 934-938, 1989; Orlandi, R., Güssow, D. H., Jones, P. T., Winter, G. Cloning immunoglobulin variable domains for expression by the polymerase chain reaction. Proc. Natl. Acad. Sci. USA 86: 3833-3837, 1989). However, the unbiased amplification of complete V repertoires requires very complex sets of degenerated primers (Marks J. D., Hoogenboom H. R., Bonnert T. P., McCafferty J., Griffiths A. D., Winter G. By-passing immunization. Human antibodies from V-gene libraries displayed on phage. J. Mol. Biol. 222: 581-597, 1991). The cloning of V regions with very atypical sequences might still not be possible by this approach. Moreover, the original sequence will be lost in those parts that are covered by the primers. The amino acids in these regions seem to contribute to the correct folding of the CDR regions (Chothia, C., Lesk, A. M., Tramontano, A., Levitt, M., Smith-Gill, S. J., et al. Conformations of immunoglobulin hypervariable regions. Nature, 342: 877-883, 1989). For this reason, V-region cloning by use of degenerate primers could lead to reduced antibody affinity. A method to circumvent these potential problems is to clone both chains of the antibody by inverse polymerase chain reaction (iPCR) with primers matching the known constant region sequences of the antibody. The cloning procedure is schematically illustrated in FIG. 1.

Cytoplasmatic RNAs were prepared from the hybridoma cell lines BV10 and 408 (Rappold I., Ziegler B. L., Köhler I., Marchetto S., Rosnet O., Birnbaum D., Simmons P. J., Zannettino A. C., Hill B., Neu S., Knapp W., Alitalo R., Alitalo K., Ullrich A., Kanz L., Bühring H. J. Functional and phenotypic characterization of cord blood and bone marrow subsets expressing FLT3 (CD 135) receptor tyrosine kinase. Blood, 90: 111-125, 1997) using the RNeasy Kit (Qiagen, Hilden, Germany) applying a modified protocol for the isolation of cytoplasmatic RNA only.

Using oligo $(dT)_{15}$ primer, double-stranded cDNA (ds-cDNA) was prepared from 0.3-2 µg of mRNA using the cDNA Synthesis System (Roche, Mannheim, Germany). More specifically, to permit blunt-end formation on the DNA strands the ds-cDNA was incubated with T4-DNA polymerase. The reaction mixture was extracted once with an equal volume phenol-chloroform-isoamylalcohol (25:24:1) and precipitated with ethanol. The dissolved ds-cDNA pellet was incubated with T4 DNA ligase (Roche, Mannheim, Germany) to circularize the cDNA (Uematsu Y. A novel and rapid cloning method for the T-cell receptor variable region sequences. Immunogenetics, 34:174-178, 1991). The 3' poly (A) tail is ligated to the unknown 5'*end* of the *c*DNA by *circularization*.

B. PCR Amplification of Immunoglobulin Variable Region cDNAs

The use of two outward-directed constant region specific primers (summarized in Table 1) in an iPCR reaction allowed the amplification of the entire cDNA of rearranged light and heavy chain gene segments. 1-5 µl of circularized ds-cDNA were included in a 50 µl standard PCR reaction (HotStar Taq DNA Polymerase, Qiagen, Hilden, Germany) with primer pair Ck-for and Ck-back for the light chain and primer pair gamma1-for and gamma1-back for the heavy chain amplification. The primers are designed to anneal to the constant regions of the cDNAs. Fourty amplification cycles were performed at the following conditions: 30 sec 94° C., 1 min 56° C., 2 min 30 sec 72° C. The resulting amplification product contains the complete V region, 5' UT region, pA tail, 3' UT region and is flanked by constant region sequences. The DNA obtained from the inverse PCR was separated on 1% agarose gels. The DNA bands of corresponding size (light chain approx. 1000 bp; heavy chain approx. 1600 bp) were cut out, isolated by standard techniques (Maniatis et al. 1982) and cloned into the pGEM-T Easy vector (Promega, Madison, Wis., USA). For sequence determination standard primers for the vector system and immunoglobulin constant region specific primers (light chain: k-for1 and k-for 2; heavy chain: CG1-for1, CG1-for 2, CG1-rev1, CG1-rev2) were used (see Table 1).

TABLE 1

Primers used for amplification and sequencing of VJ and VDJ regions of FLT3 specific antibodies

| | | Oligonucleotides used for the inverse PCR |
|---|---|---|
| A | gamma1-for | 5'-CAA GGC TTA CAA CCA CAA TCC CTG G-3' (SEQ ID NO: 45) |
| A' | gamma1-back | 5'-CAT ATG TAC AGT CCC AGA AGT ATC ATC TG-3' (SEQ ID NO: 46) |
| B | Ck-for | 5'-TGT TCA AGA AGC ACA CGA CTG AGG CAC CTC C-3' (SEQ ID NO: 47) |
| B' | Ck-back | 5'-ACT TCT ACC CCA AAG ACA TCA ATG TCA AG-3' (SEQ ID NO: 48) |

| | Oligonucleotides used for sequencing |
|---|---|
| k-for1 | 5'-CCT GTT GAA GCT CTT GAC AAT GGG-3' (SEQ ID NO: 49) |
| k-for2 | 5'-ATG TCT TGT GAG TGG CCT CAC AGG-3' (SEQ ID NO: 50) |
| CG1-for1 | 5'-CGT CTA CAG CM GCT CAA TGT GC-3' (SEQ ID NO: 51) |
| CG1-for2 | 5'-CCA TCT GTC TAT CCA CTG GCC-3' (SEQ ID NO: 52) |
| CG1-rev1 | 5'-CCA GGT CAC TGT CAC TGG CTC AG-3' (SEQ ID NO: 53) |
| CG1-rev2 | 5'-CCT CAT GTA ACA CAG AGC AGG-3' (SEQ ID NO: 54) |

Thus, the complete light chains and heavy chains of murine antibodies 4G8 (light chain amino acid sequence set forth in SEQ ID NO:15 including the variable domain (SEQ ID NO:13), the variable domain including CDR1 (SEQ ID NO:1), CDR2 (SEQ ID NO:2) and CDR3 (SEQ ID NO:3); heavy chain amino acid sequence set forth in SEQ ID NO:16, including the variable domain (SEQ ID NO:14), the variable domain including CDR1 (SEQ ID NO:4), CDR2 (SEQ ID NO:5) and CDR3 (SEQ ID NO:6)) and BV10 (light chain amino acid sequence set forth in SEQ ID NO:31 including the variable domain (SEQ ID NO:29), the variable domain including CDR1 (SEQ ID NO:7), CDR2 (SEQ ID NO:8) and CDR3 (SEQ ID NO:9); heavy chain amino acid sequence set forth in SEQ ID NO:32 including the variable domain (SEQ ID NO:30), the variable domain including CDR1 (SEQ ID NO:10), CDR2 (SEQ ID NO:11) and CDR3 (SEQ ID NO:12)) were identified.

The light chain of murine antibody 4G8 is encoded by the nucleotide sequence set forth in SEQ ID NO:19 (complete cDNA sequence set forth in SEQ ID NO:20), wherein the variable domain is encoded by the nucleotide sequence set forth in SEQ ID NO:17. The heavy chain of antibody 4G8 is encoded by the nucleotide sequence set forth in SEQ ID NO:21 (complete cDNA sequence set forth in SEQ ID NO:22), wherein the variable domain is encoded by the nucleotide sequence set forth in SEQ ID NO:18.

The light chain of murine antibody BV10 is encoded by the nucleotide sequence set forth in SEQ ID NO:35 (complete cDNA sequence set forth in SEQ ID NO:36), wherein the variable domain is encoded by the nucleotide sequence set forth in SEQ ID NO:33. The heavy chain of antibody BV10 is encoded by the nucleotide sequence set forth in SEQ ID NO:37 (complete cDNA sequence set forth in SEQ ID NO:38), wherein the variable domain is encoded by the nucleotide sequence set forth in SEQ ID NO:34.

Example 2

Construction and Expression of Chimeric FLT3 Specific Antibodies and their Derivatives In the second construction step of recombinant antibodies, the cloned V regions were combined with the desired C regions in an expression vector. The cloning procedure performed here allows the introduction of complete Ig V regions and their expression in lymphoid cells without any alterations of their amino acid sequence. For this, The nucleotide sequence of the amplicon obtained in Example 1 was determined after subcloning by sequencing (primer in Table 1) and used for design of primer pairs (C C'; D D'; Table 2). The reamplified DNA fragments of the V segments is cut with appropriate restriction nucleases (summarized in Table 2) and then ligated into the expression vectors. The vectors (FIGS. 2 and 3) contain human light and heavy constant region genes. Thus insertion of the amplified and recut V segments reconstitutes the original genomic organisation of the Ig genes on the vectors without altering any amino acid of the V regions.

The parental vector for the light chain contains the VJ region of the mouse light chain and the C region of human κ gene. Restriction sites were introduced at the required locations (XhoI and SpeI) in order to substitute the light chain XhoI-SpeI fragment with the appropriate VJ fragment of the light chain of monoclonal antibodies BV10 or 4G8 or any other monoclonal antibody. The region relevant for the fragment exchange is shown enlarged in FIG. 2. The fragment to be exchanged contains part of the second exon of the leader sequence, an appropriate site (XhoI) for in frame fusion, the VJ region and part of the second intron with restriction site SpeI.

The original vector for the heavy chain contains the human γ1 isotype Ig heavy chain. Restriction sites were introduced at the required positions in intron I and II for exchange of the AatII-ClaI fragment with the VDJ fragment of the heavy chain of monoclonal antibodies BV10 or 4G8 or any other monoclonal antibody. The region relevant for cloning the VDJ fragment is shown enlarged in FIG. 3a. The fragment to be exchanged contains parts of the first intron with an AatII restriction site, the second exon of the leader sequence, the VDJ region and part of the second intron with the restriction site ClaI. For the substitution of all exons of the constant region, restriction sites were introduced at the required position in intron II (MluI) and intron VI (SpeI). The MluI-SpeI fragment to be exchanged (shown enlarged in FIG. 3b) contains the entire constant region of the human γ1 heavy chain and two amino acid modifications in the CH2 domain as indicated ($Ser_{239}$-Asp; $Ile_{332}$-Glu)

Furthermore, with the expression vectors used, it is possible to exchange the entire constant region of the human Igγ1 isotype (MluI-SpeI fragment; see FIG. 3) either against constant regions of all other antibody isotypes or against Fc parts with optimized or reduced effector function. In the case of antibodies optimized for triggering ADCC a S239D and I332E (amino acid position according to Kabat nomenclature) exchange were introduced in the CH2 domain of human γ1 constant region. This was done according the publication of Lazar et al. (Lazar G. A., Dang W, Karki S, Vafa O, Peng J. S., Hyun L, Chan C, Chung H. S., Eivazi A, Yoder S. C., Vielmetter J, Carmichael D. F., Hayes R. J., Dahiyat B. I. Engineered antibody Fc variants with enhanced effector function. Proc. Natl. Acad. Sci. USA 103: 4005-4010, 2006).

TABLE 2

Oligonucleotides used for amplification of VJ and VDJ segments obtained by iPCR for the insertion into expression vectors Oligonucleotides used for the heavy chain VDJ segment

| | | |
|---|---|---|
| C | 408-H-for | 5'-tct ctt cac agg tgt cct ctc tca ggt cca act gca gca gcc tgg ggc tga gc-3' (SEQ ID NO: 55) |
| C' | 4G8-H-rev | 5'-gag aag gta gga ctc acc tga gga gac tgt gag agt ggt gcc ttg gcc cca g-3' (SEQ ID NO: 56) |
| C | BV10-H-for | 5'-aga cgt cca ctc tgt ctt tct ctt cac agg tgt cct ctc cca ggt gca gct gaa gca gtc-3' (SEQ ID NO: 57) |
| C' | BV10-H-rev | 5'-gag aag gta gga ctc acc tga gga gac ggt gac tga ggt tcc ttg acc c-3' (SEQ ID NO: 58) |
| C | universal for (AatII) | 5'-aga cgt cca ctc tgt ctt tct ctt cac agg tgt cct ctc c-3' (SEQ ID NO: 59) |
| C' | universal rev (ClaI) | 5'-tat cga ttt aga atg gga gaa ggt agg act cac-3' (SEQ ID NO: 60) |

Oligonucleotides used for the light chain VJ segment

| | | |
|---|---|---|
| D | 4G8-L-for (XhoI) | 5'-act cga gga gat att gtg cta act cag tct cca gcc acc ctg-3' (SEQ ID NO: 61) |
| D' | 4G8-L-rev (SpeI) | 5'-tac tag tac tta cgt ttt att tcc agc ttg gtc ccc cct cc-3' (SEQ ID NO: 62) |

TABLE 2-continued

Oligonucleotides used for amplification of VJ and VDJ segments
obtained by iPCR for the insertion into expression vectors

| D | BV10-L-for (XhoI) | 5'-act cga gga gac att gtg atg aca cag tct cca tcc tcc c-3' (SEQ ID NO: 63) |
|---|---|---|
| D' | BV10-L-rev (SpeI) | 5'-act agt act tac gtt tca gct cca gct tgg tcc cag cac cga acg tg-3' (SEQ ID NO: 64) |

Restriction sites are shown in bold and indicated by letters in parentheses.

Thus, chimeric antibodies 4G8 and BV10 and the Fc optimized variants SDIE 4G8 and SDIE BV10 were obtained. These comprise the following amino acid and nucleotide sequences:

Chimeric antibody 4G8: light chain amino acid sequence as set forth in SEQ ID NO:23 and as encoded by the nucleotide sequence set forth in SEQ ID NO:24, heavy chain amino acid sequence as set forth in SEQ ID NO:25 and as encoded by the nucleotide sequence set forth in SEQ ID NO:26.

SDIE 4G8 (chimeric, Fc optimized antibody): light chain amino acid sequence set forth in SEQ ID NO:23 and encoded by the nucleotide sequence set forth in SEQ ID NO:24, heavy chain amino acid sequence set forth in SEQ ID NO:27 and encoded by the nucleotide sequence set forth in SEQ ID NO:28.

Chimeric antibody BV10: light chain amino acid sequence as set forth in SEQ ID NO:39 and as encoded by the nucleotide sequence set forth in SEQ ID NO:40, heavy chain amino acid sequence as set forth in SEQ ID NO:41 and as encoded by the nucleotide sequence set forth in SEQ ID NO:42.

SDIE BV10 (chimeric, Fc optimized antibody): light chain amino acid sequence set forth in SEQ ID NO:39 and encoded by the nucleotide sequence set forth in SEQ ID NO:40, heavy chain amino acid sequence set forth in SEQ ID NO:43 and encoded by the nucleotide sequence set forth in SEQ ID NO:44.

Example 3

Expression and Purification of Anti-FLT3 Antibodies

Cotransfection of the expression vectors encoding the chimeric heavy and light chain (IgG1/κ) or modified heavy chains into the non-Ig-producing myeloma cell line Sp2/0 yielded stable transfectomas secreting chimeric monoclonal antibodies which are able to bind specifically to FLT3 on human REH cells, and FLT3 transfectants (Sp2/0).

Chimeric antibodies were purified from cell culture supernatant by affinity chromatography on Protein A.

Example 4

ADCC Effector Function of Anti-FLT3 Antibodies

The ADCC effector function of the Fc optimized, chimeric anti-FLT3 antibodies 4G8-SDIE and BV10-SDIE in comparison to the corresponding chimeric antibodies without Fc optimization (FIGS. 4 A and B) as well as an chimeric anti-NG2 antibody comprising the same Fc modification (FIG. 4C) was demonstrated using chromium release assays. Moreover, the cell killing activity of 4G8-SDIE and unstimulated PBMCs in comparison to the parenteral mouse antibody 4G8 was shown for AML blasts isolated from a human patient with acute myelogeneous leukemia (FIG. 5). The target cells used were:

NALM16: an acute lymphoblastic leukaemia (ALL) cell line, supplier: Department of Pediatric Oncology, University of Tübingen, original characterization: Minowada J et al. J Cancer Res Clin Oncol 101:91-100 (1981).

SK-Mel63: Human melanoma cell line, original supplier: Dr. A. Knuth, Nordwestkrankenhaus Frankfurt/Main, Germany.

SG3: Leukemic cells, isolated from the peripheral blood of a patient with acute myelogeneous leukemia (AML) by density gradient centrifugation; supplied by Dr. H. Salih, Department of Medical Oncology, University of Tübingen The effector cells used were peripheral blood mononuclear cells (PBMCs) isolated from the blood of normal healthy donors.

The chromium release assay was performed as follows: $10^6$ target cells were labeled with sodium chromate ($^{51}$Cr, 150 µCi/ml) for 1 hr, washed and plated in 96-well mictotiter plates (10.000 cells per well). PBMC and antibodies were then added at the indicated concentrations. After 4 and 20 hrs respectively supernatant was harvested and counted in a MicroBeta Counter. Cytotoxicity was determined according to the standard formula: % specific $^{51}$Cr-release=(experimental release−spontaneous release):(total release−spontaneous release)×100. Spontaneous and total release were determined by incubating target cells in medium with and without 2% Triton-X100, respectively.

Figure 4:
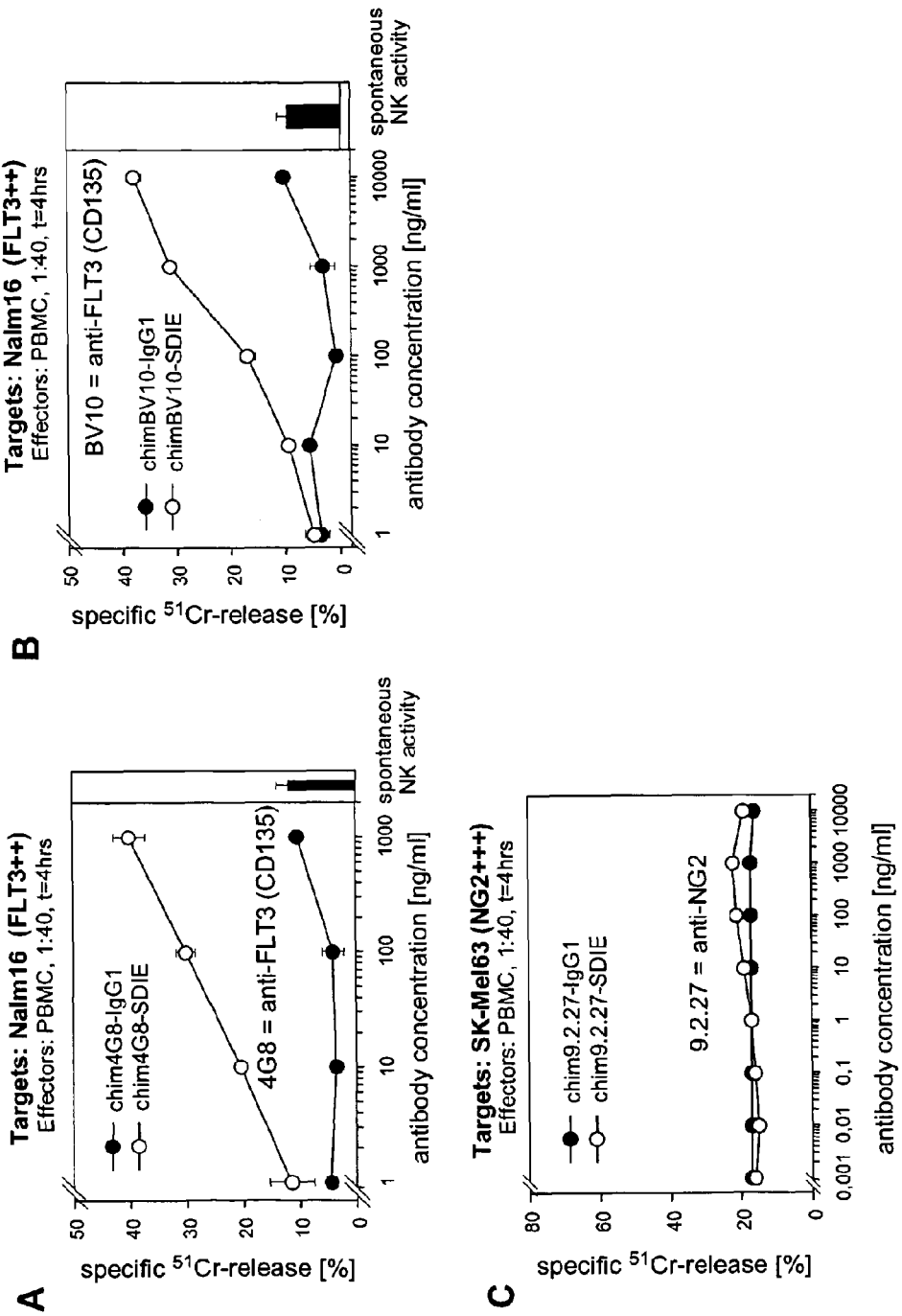
FIG. 4 shows the cell killing effects of the Fc optimized chimeric antibodies chim4G8-SDIE (A) and chimBV10-SDIE (B) respectively and unstimulated human PBMCs against cultured FLT3-expressing human NALM16 leukemia cells in comparison to the unmodified chimeric antibodies chim4G8 and chimBV10.
Figure 5:
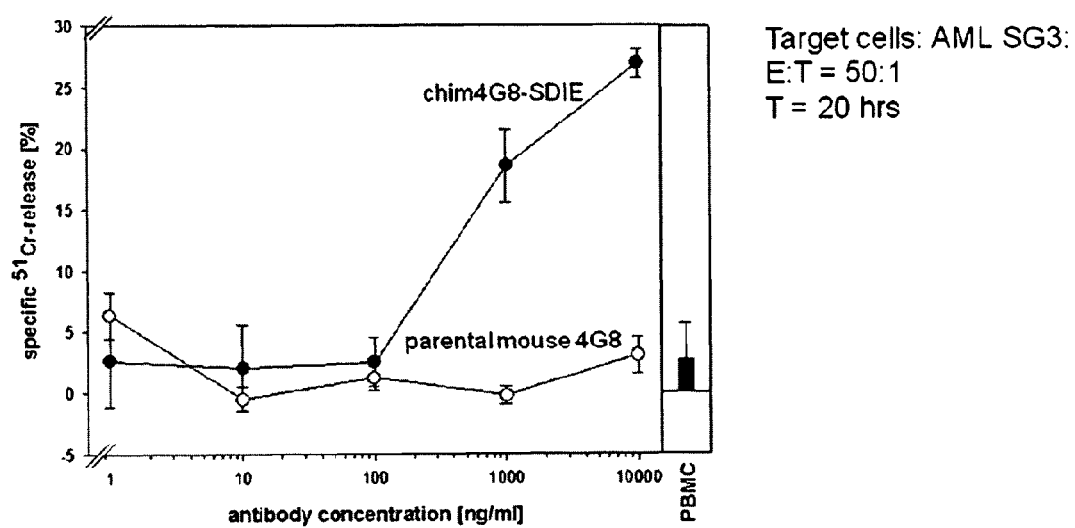
FIG. 5 shows the cell killing effect by the optimized anti-FLT3 antibody 4G8-SDIE and unstimulated human PBMCs on AML-blasts in comparison to the unmodified parental mouse antibody.

The results depicted in FIGS. 4 and 5 clearly show that the introduction of the Fc modifications S239D and I332E into the CH2 domain of the heavy chain of chimeric anti-Flt3 antibodies 4G8 and BV10 could induce significant cell killing activity in both antibodies. In contrast to these results, the introduction of the same modifications into a chimeric anti-NG2 antibody had no such effect. Accordingly, there is no general principle that the two modifications used can confer cell killing activity to any given antibody, but rather have to be carefully selected for each individual monoclonal antibody.

Example 5

Production and Purification of Recombinant and Fc-Optimized Antibodies

Figure 2:
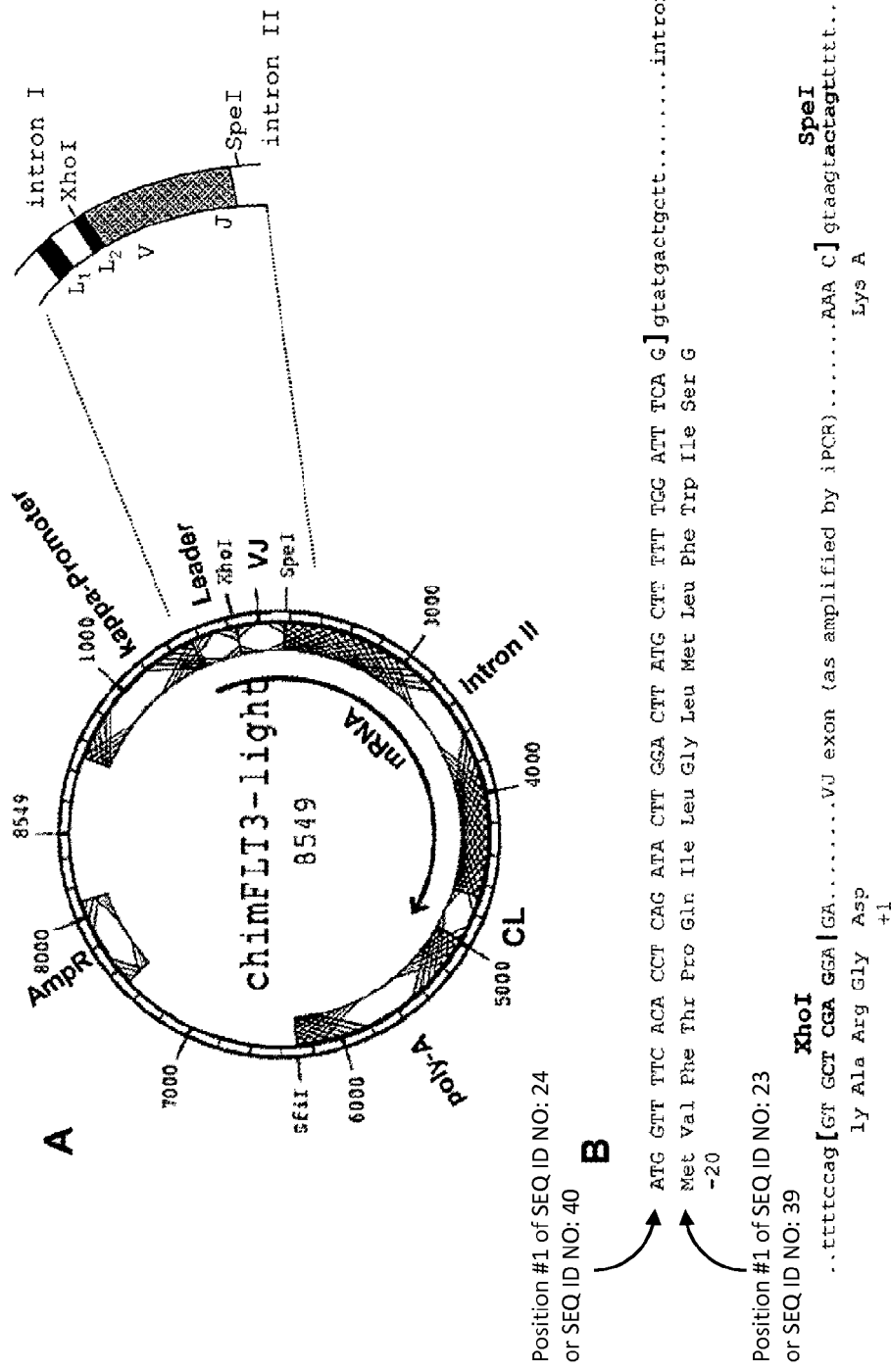
FIG. 2 shows the parental vector containing the VJ region of the mouse light chain and the C region of human κ gene. The region relevant for the fragment exchange is shown enlarged in FIG. 2A. The sequence context generated upon insertion of the VJ region of monoclonal antibodies BV10 or 4G8 into the expression vector chimFLT3-light is shown in FIG. 2B. The cleavage site for secretory signal peptides is indicated by |; and exon-intron boundaries by [,].
Figure 3:
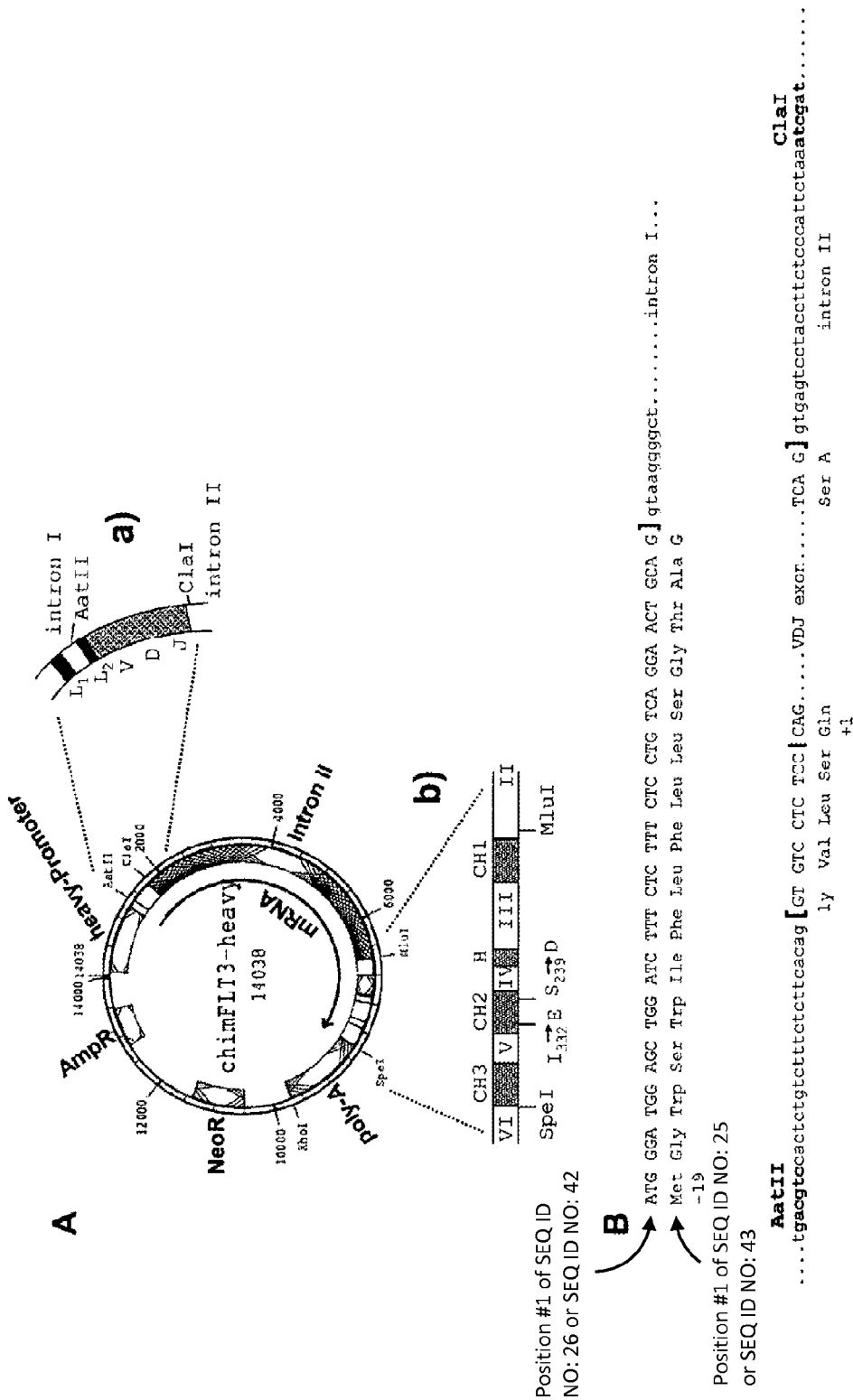
FIG. 3 shows the original vector containing the human γ1 isotype Ig heavy chain. The region relevant for cloning the VDJ fragment is shown enlarged (a). The MluI-SpeI fragment to be exchanged (shown enlarged as b) contains the entire constant region of the human γ1 heavy chain and two amino acid modifications in the CH2 domain as indicated ($Ser_{239}$-Asp; $Iso_{332}$-Glu).

The mRNA of mouse antibodies BV10 and 4G8 (both IgG1/κ) was isolated from hybridomas with the RNeasy Kit (Qiagen, Hilden, Germany). Unknown variable regions of heavy (VDJ) and light (VJ) chain were identified by sequencing of inverse PCR amplicons generated as previously described (Herrmann T, Grosse-Hovest L, Otz T, Krammer P H, Rammensee H G, Jung G. Construction of optimized bispecific antibodies for selective activation of the death receptor CD95. *Cancer Res.* 2008; 68(4):1221-1227), using specific primers for mouse constant genes of light (Ck-for (SEQ ID NO:47); Ck-back (SEQ ID NO:48)) and heavy chain (gamma1-for (SEQ ID NO:45); gamma1-back (SEQ ID NO:46). The cloning of the variable genes from the hybridoma 9.2.27 (GenBank: #AJ459796; #AJ459797), producing an IgG2a/κ CSPG4 antibody has also been described previously (Grosse-Hovest L, Hartlapp I, Marwan W, Brem G, Rammensee H G, Jung G. A recombinant bispecific single-chain antibody induces targeted, supra-agonistic CD28-stimulation and tumor cell killing. *Eur J. Immunol.* 2003; 33(5):1334-1340). For the generation of chimerized and optimized antibodies, the VJ and VDJ elements, were re-amplified using the oligonukleotides listed in table 2 and cloned into eukaryotic expression vectors as shown in FIGS. 2 and 3. Besides the amino acid exchanges at S239D and I332E, the optimized G1 Fc-part contains a C-terminal M-tag (PTHVNVSVVMAEEQKLISEEDLLR; SEQ ID NO: 66, which was derived from the amino acid sequences PTHVNVSVVMAE (amino acid #455-466 of the human Igα1 tailpiece) (SEQ ID NO: 67) and the c-myc epitope EQKLISEEDLLR (SEQ ID NO:68) (Evan G I, Lewis G K, Ramsay G, Bishop J M. Isolation of monoclonal antibodies specific for human c-myc proto-oncogene product. *Mol Cell Biol.* 1985; 5(12):3610-3616). Recombinant antibodies, as well as parental mouse 4G8 and BV10, were purified from culture supernatant of transfectants and hybridoma cells, respectively, using protein A affinity-chromatography (GE Healthcare, Munich, Germany). In the case of 4G8SDIEM, a large batch of the antibody (15 g) was produced in GMP compliant clean rooms using disposable technology including a 100 L biowave reactor (Sartorius; Goettingen, Germany) for fermentation and an Äkta Ready system for purification by protein A-, ion exchange- and hydrophobic interaction chromatography (MabSelect Sure and CaptoAdhere columns, GE Healthcare, Munich, Germany).

Example 6

FLT3-Specificity and Avidity of Antibody Binding

The parental mouse antibodies 4G8 and BV10 were originally described and characterized as recognizing the FLT3 protein (Rappold I, Ziegler B L, Kohler I, et al. Functional and phenotypic characterization of cord blood and bone marrow subsets expressing FLT3 (CD135) receptor tyrosine kinase. *Blood.* 1997; 90(1):111-125). FIG. 7A shows that both SDIEM-modified antibodies specifically bind to this protein on transfected mouse Sp2/0 cells. In FIG. 7B binding of the two antibodies to FLT3 positive human NALM16 cells is assessed by flow cytometry. Antibodies do not cross-block each other (data not shown) and thus recognize two spatially separated epitopes of the FLT3 protein. Both antibodies saturated FLT3-molecules on NALM16 cells at concentrations below 1 µg/ml. Binding of the chimerized 4G8 antibody was stronger than that of BV10. This is not due to chimerization or optimization since a similar difference was observed when binding of the mouse parental versions of 4G8 and BV10 was compared (FIG. 7C). No differences in binding between the chimeric and the SDIEM modified chimeric versions of the antibodies were detected (FIG. 7B). A SDIE-modified antibody, termed 9.2.27SDIE, directed against a melanoma associated surface antigen, did not bind to NALM16 cells and was used as a negative control in this and several subsequent experiments.

Example 7

Competition with Binding of the FLT3 Ligand (FLT3L)

Figure 8:
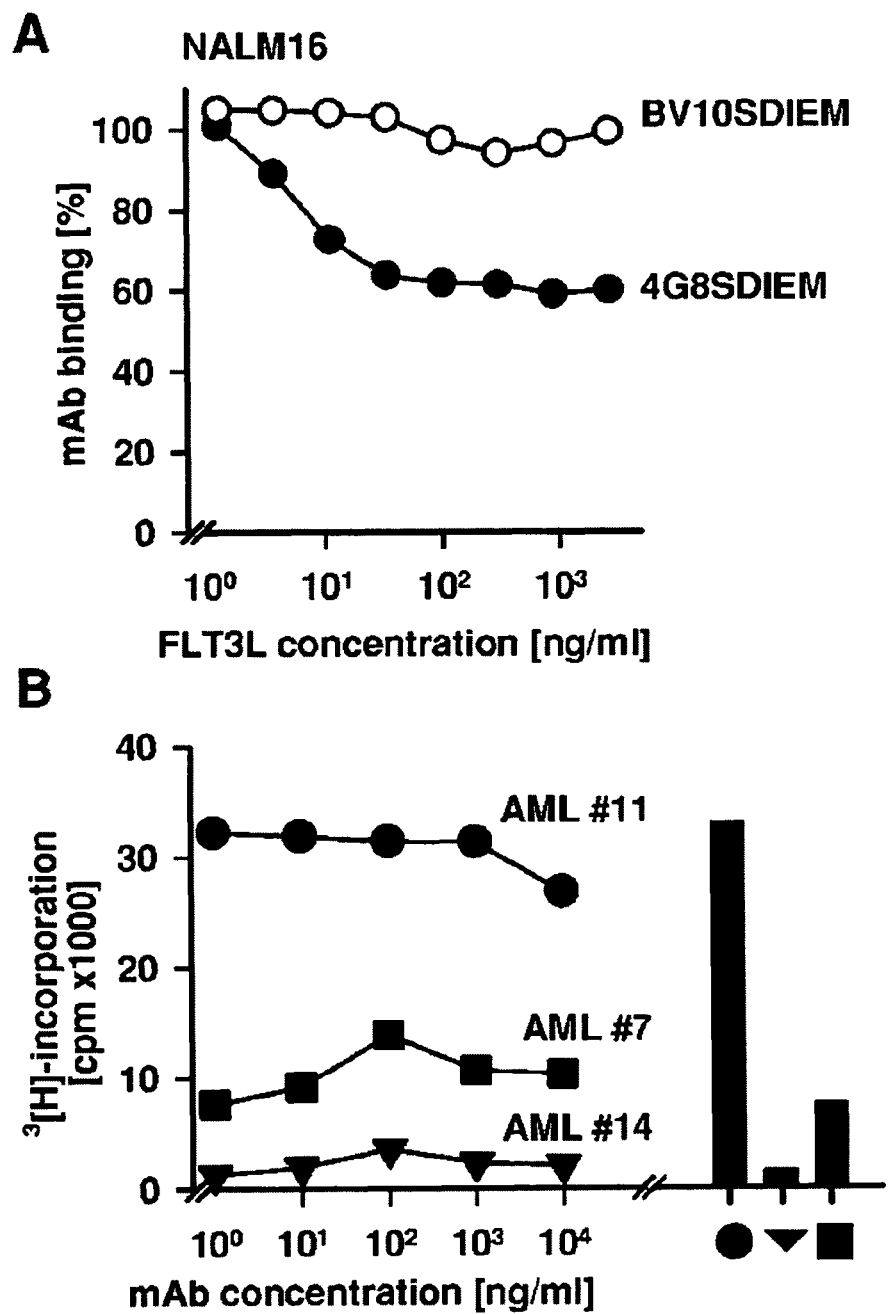
FIG. 8 shows the effect of 4G8SDIEM on FLT3-ligand (FLT3L) binding and proliferation of leukemic cells. (A) NALM16 cells were incubated with 4G8SDIEM or BV10SDIEM at 1 µg/ml in the presence of the indicated concentrations of the recombinant FLT3 ligand and the amount of bound antibody was determined by indirect immunofluorescence and flow cytometry. (B) AML blasts isolated from the peripheral blood of three different patients by density gradient centrifugation were incubated with the indicated concentrations of 4G8SDIEM for 24 hours and proliferation was assessed using a 3[H]-thymidine uptake assay. Bars on the right represent proliferation in the absence of the antibody.

In general, interference with binding of the natural ligand may contribute to the therapeutic activity of an antibody. FIG. 8A shows that recombinant FLT3L partly inhibits binding of 4G8SDIEM, but not of BV10SDIEM to NALM16 cells, indicating that the binding site of the 4G8 antibody is in close proximity to that of the FLT3 ligand. Therefore, the effect of 4G8SDIEM on the spontaneous proliferation of the leukemic blasts of three different patients was evaluated in vitro using the non binding SDIE-modified 9.2.27 antibody as a control. Whereas spontaneous proliferation of the primary AML cells varied substantially, significant effects of the antibodies on cell proliferation were not observed (FIG. 8B).

Example 8

Antibody Dependent Cellular Cytotoxicity

Figure 7:
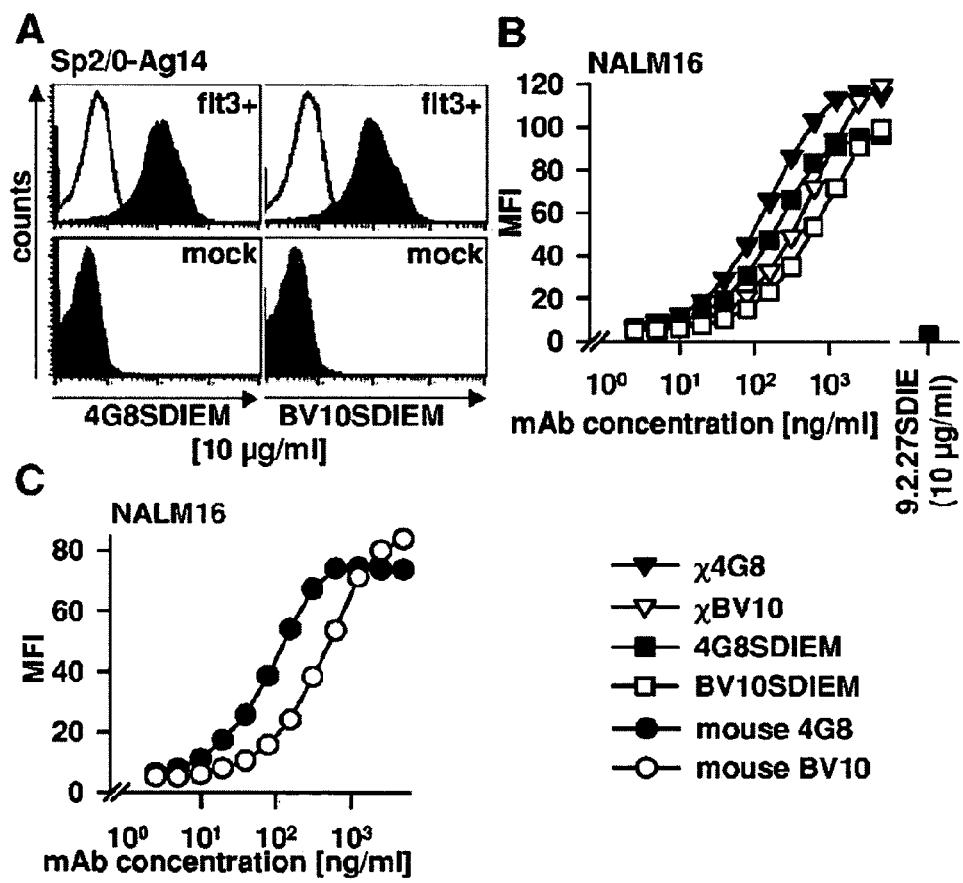
FIG. 7 shows the binding of mouse, chimeric and optimized 4G8 and BV10 to FLT3. FLT3- and mock-transfected Sp2/0 cells (A) or NALM16 cells (B,C) were incubated with the indicated antibodies and analyzed by indirect immunofluorescence and flow cytometry. Open and shaded histograms in (A) represent staining with isotyp control and the indicated FLT3 antibodies (10 µg/ml), respectively. MFI=mean fluorescence intensity.
Figure 9:
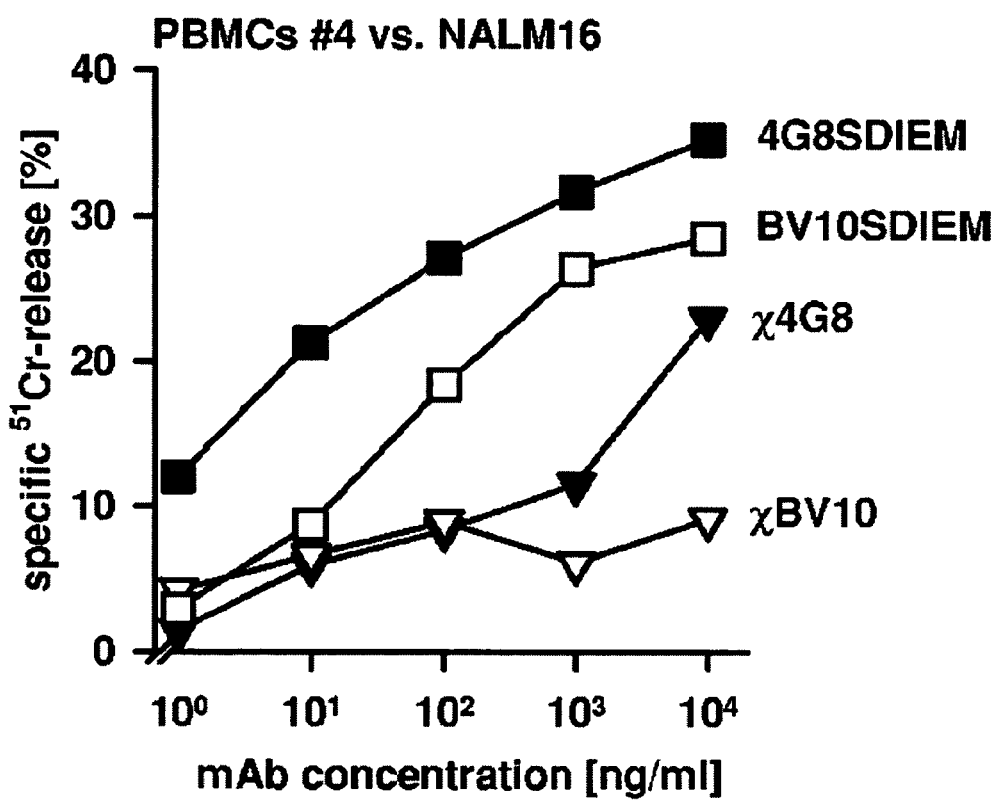
FIG. 9 shows. ADCC activity of unmodified and SDIEM-modified versions of the FLT3 antibodies 4G8 and BV10. 51[Cr]-labeled NALM16 cells were incubated for 4 hours with PBMCs of a healthy donor (#4) in the presence of the indicated concentrations of the unmodified chimeric (χ) or SDIEM-modified versions of 4G8 and BV10 at a PBMC: target cell ratio of 50:1. Killing of the target cells was determined using a standard 51[Cr] release assay. One representative result of 6 independent experiments with PBMCs from different healthy donors is depicted.

FIG. 9 shows that the ADCC activity of PBMCs against NALM16 cells is markedly enhanced in the presence of the SDIEM-modified antibodies as compared to that of the unmodified chimeric antibody versions. In several experiments, the concentrations required to achieve comparable lysis by unmodified and SDIEM-modified antibodies differed by a factor of at least 100. Killing by the 4G8SDIEM antibody was significantly better than that achieved by BV10SDIEM, in particular at low concentrations. This corresponds to the moderately lower binding avidity of BV10 (FIG. 7).

Figure 10:
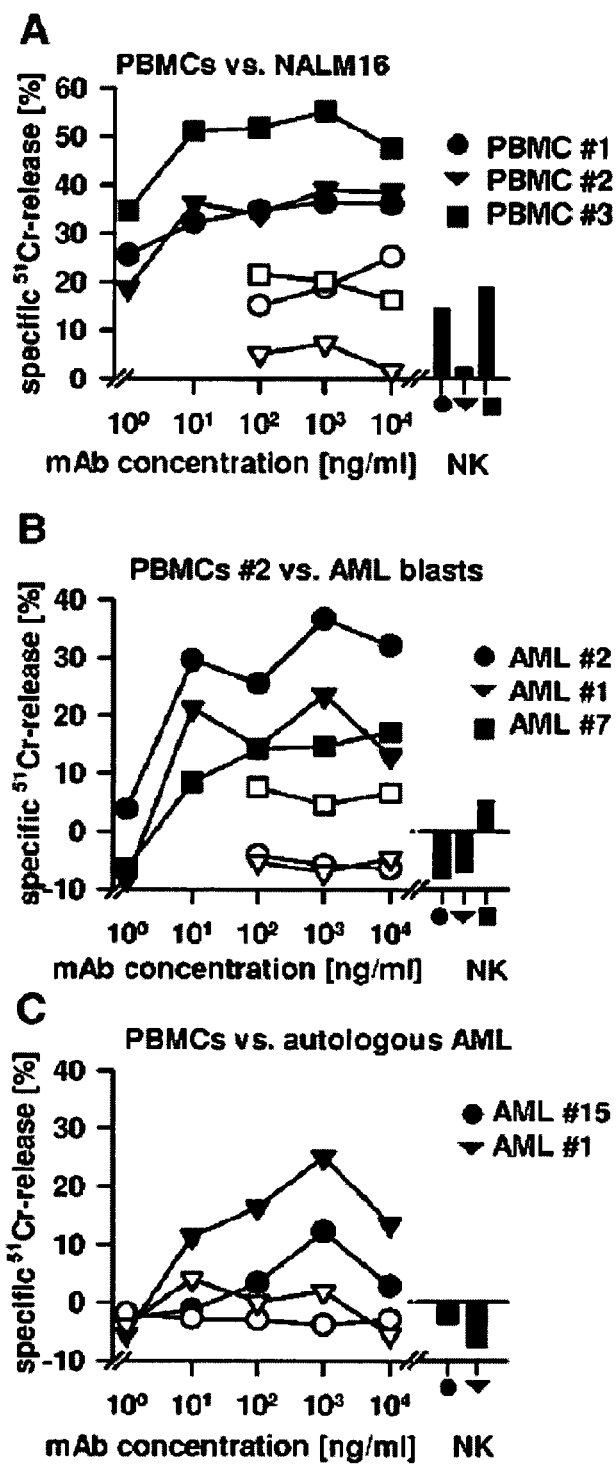
FIG. 10 shows the ADCC activity of 4G8SDIEM against leukemic cells. Cytolytic activity of the PBMCs of three different healthy donors (PBMC #1, #2, #3) against NALM16 cells (A) and of the PBMCs of donor #2 against leukemic blasts of three different patients (AML #1, #2, #7) (B) was determined in a 4 hours and 8 hours 51[Cr] release assay, respectively. In (C) the cytolytic activity after 8 hours against AML blasts #1 and #15 is depicted using autologous PBMCs of the respective patients as effector cells. Filled and open symbols indicate ADCC mediated by 4G8SDIEM and non-binding control antibody 9.2.27SDIE, respectively. Filled bars on the right (NK) indicate NK-activity in the absence of antibody. Note that PBMC #1-3 refer to PBMCs of healthy donors and are not related to AML blasts #1-3.

In FIG. 10A the ADCC activity of 4G8SDIEM is depicted using PBMCs of three different healthy donors (#1-3). In these experiments, the SDIEM-modified mAb 9.2.27 was used as a negative control. The cytolytic activity in the presence of this reagent did not exceed that of NK cells in the absence of antibodies which varied between 0 and 20%. In FIG. 10B the ADCC activity of PBMCs from a healthy donor (#2) against leukemic blasts of three different patients is shown. ADCC activity mediated against these blasts (AML #1, AML #2, AML #7), carrying 4000, 4500 and 3200 FLT3 molecules per cell, respectively, was less pronounced than that against cultured NALM 16 cells. It required 8 rather than 4 hours to become clearly detectable. Generally, the ADCC—as well as the NK-activity against NALM16 cells and leukemic blasts continued to rise after 8 hours. However, using primary blasts, it was difficult to further prolong the assay time due to increasing spontaneous chromium release.

Next the ADCC activity of PBMCs isolated from the blood of AML patients against autologous blasts was evaluated. To this end, leukemic blasts from PBMC preparations were depleted and the depleted PBMCs were used as effector cells against the positively selected blasts (see Materials and Methods). Under these conditions significant lysis in 2 (AML #1, #15) out of 5 independent experiments with blasts and autologous PBMCs of the respective patients (FIG. 10C) was detected.

Example 9

Antigenshift

Figure 11:
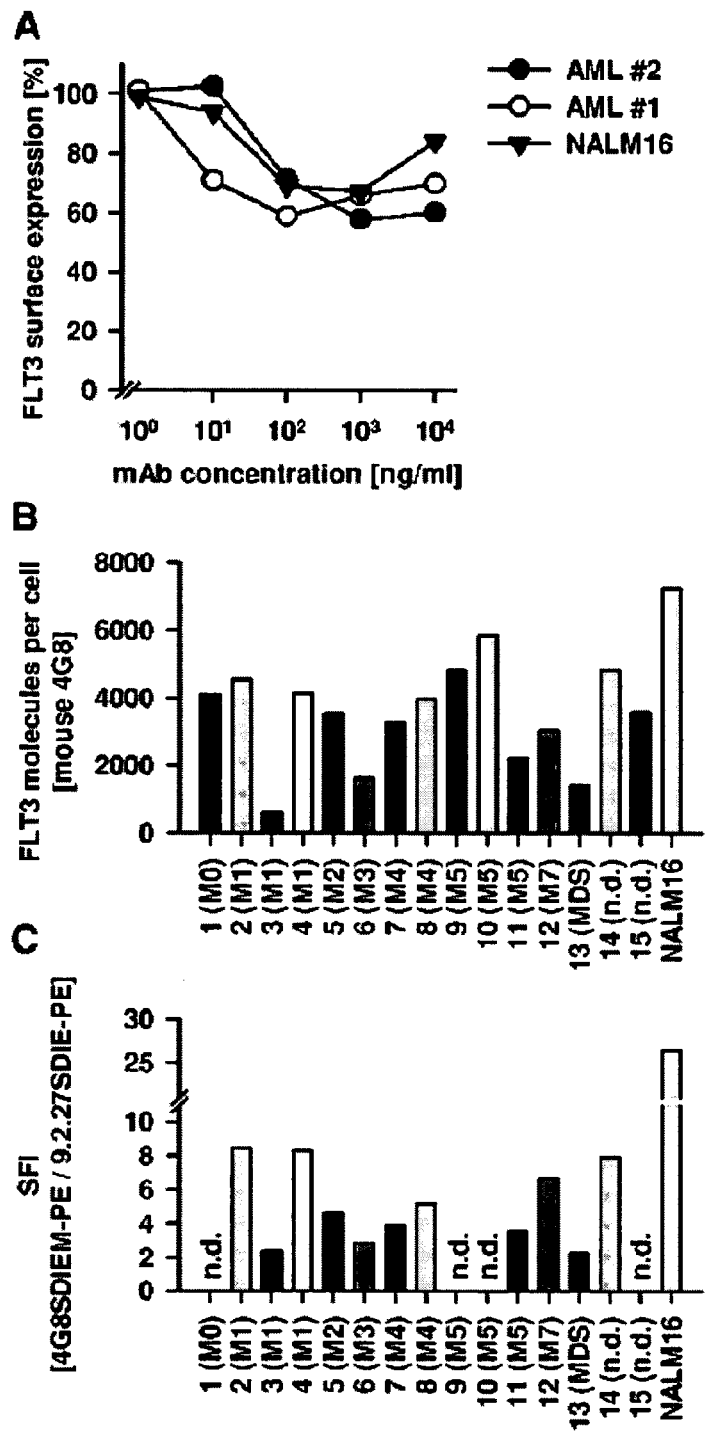
FIG. 11 shows antigen shift and FLT3 expression on leukemic cells of different origin (A) NALM16 cells and blasts from two different AML patients were incubated with the indicated concentrations of 4G8SDIEM. After 48 hours cells were washed, re-incubated with 2 µg/ml of 4G8SDIEM and analyzed by indirect immunofluorescence and flow cytometry. FLT3 expression detected on cells preincubated without antibodies was defined as 100%. (B) AML blasts from 15 patients were incubated with mouse 4G8 (10 µg/ml), washed and analyzed by indirect immune fluorescence and flow cytometry. The amount of bound antibody molecules was determined by comparison with calibrated beads (QIFIKIT). (C) The AML blast used in (B) were incubated with PE-conjugated 4G8SDIEM or non binding PE conjugated 9.2.27SDIE antibody (10 µg/ml) and analyzed by direct immunofluorescence and flow cytometry. SFI=specific fluorescence index. The SFI of four samples was not determined (n.d.) because of high binding of the 9.2.27SDIE control antibody.

Modulation of target antigen expression upon antibody binding is a phenomenon often observed during antibody therapy. In particular, a sustained and complete loss has been reported upon treatment of AML patients with a saturating dose of the CD33 antibody Lintuzumab (Feldman E J, Brandwein J, Stone R, et al. Phase III randomized multicenter study of a humanized anti-CD33 monoclonal antibody, lintuzumab, in combination with chemotherapy, versus chemotherapy alone in patients with refractory or first-relapsed acute myeloid leukemia. *J Clin Oncol.* 2005; 23(18):4110-4116). FIG. 11A depicts the antigen shift induced after incubation of NALM cells or primary leukemic blasts of two patients (AML #1 and #2) with various concentrations of 4G8SDIEM for 48 hrs. On all these cells a moderate antigen shift was observed which was already completed after 24 hrs of incubation (data not shown).

Example 10

Binding to Normal and Leukemic Cells

FIGS. 11B and 11C show binding of the parental mouse 4G8 antibody and 4G8SDIEM, respectively, to a panel of leukemic cells obtained from patients suffering from the indicated subtypes of AML. Gated CD33+CD45dim or CD34+CD45dim-cells were analyzed. FLT3 was detected on all 15 patient samples. The number of molecules per cell determined by indirect immunofluorescence and quantitative flow cytometry varied from 500 to 6000, that on NALM16 cells from 6000 to 9000 (FIG. 11B). In FIG. 11C, 4G8SDIEM-PE rather than mouse 4G8 was used for staining. In this case, an SFI value was calculated to quantify antibody binding. For blasts from 4 of the 15 donors this index was not determined because of high, unspecific reactivity with the control antibody 9.2.27SDIE. As expected, SFI values of the evaluable samples closely matched the numbers of molecules determined by quantitative FACS (FIG. 11C).

Figure 12:
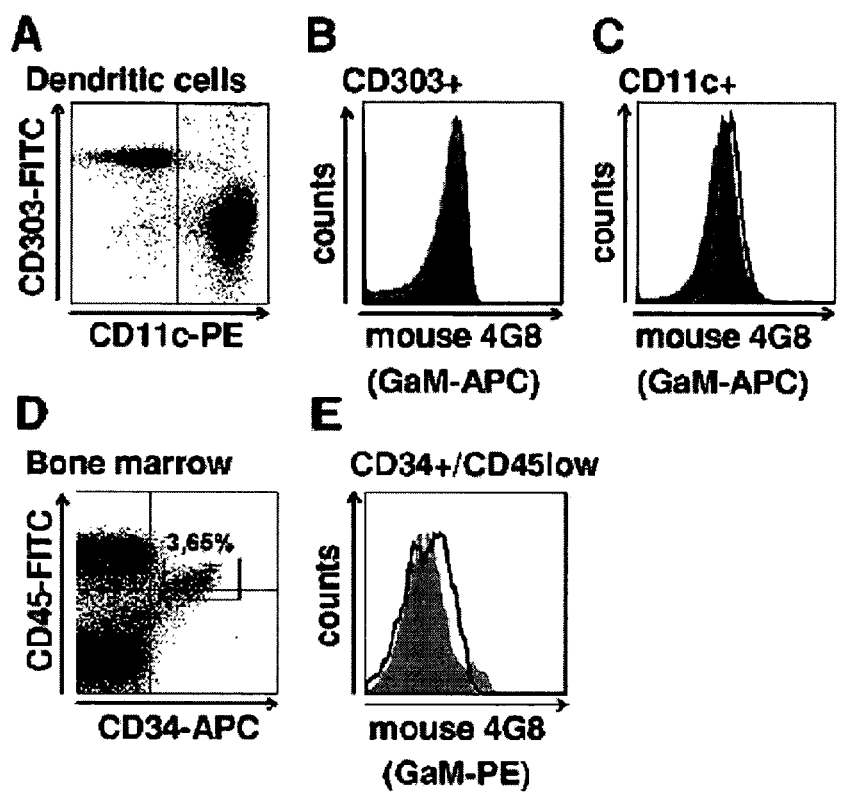
FIG. 12 shows the expression of FLT3 on normal DCs and bone marrow cells. (A) DCs isolated from the peripheral blood of healthy donors by magnetic cell separation were incubated with mouse 4G8, washed, stained with a labeled secondary antibody, washed again, and incubated with a mixture of differently labeled CD11c- and CD303-antibodies. Cells were then analyzed by flow cytometry. Binding of 4G8 to the CD303+ pDC and the CD11c+ mDC subpopulation is depicted in (B) and (C), respectively. (D,E) Similar to (A-C) normal bone marrow cells isolated by density gradient centrifugation were incubated with mouse 4G8, washed, stained with labeled secondary antibody and a mixture of differently labeled CD34- and CD45-antibodies. Binding of 4G8 to the CD34+CD45low subpopulation is depicted in (E). Shaded histograms represent primary staining with isotype control, open histograms with mouse 4G8. Representative results from one of three experiments with DCs and bone marrow cells from different healthy donors are shown.

FIGS. 12A-C show that binding of mouse 4G8 to CD11c-positive mDCs and to CD303-positive pDCs purified from normal PBMCs was marginal at best. The numbers of FLT3 molecules expressed on these cells were below 100/cell. In addition, DCs from normal PBMCs were generated. Although these cells expressed large amounts of the DC associated markers CD80, CD86 and CD123, binding of 4G8 antibodies was again barely detectable (data not shown). Next binding of mouse 4G8 to CD34-positive cells in normal bone marrow was evaluated. Again, binding of the antibody to bone marrow cells of three different donors was marginal with less than 300 molecules per cell (FIG. 12D). In summary, binding of FLT3-antibodies to normal DCs and bone marrow cells was significantly lower than to all FLT3-expressing leukemic cells examined. In addition, binding of FLT3 antibodies to PBMCs, thrombocytes, erythrocytes and granulocytes was not observed (data not shown).

Example 11

Toxicity In Vitro

Figure 13:
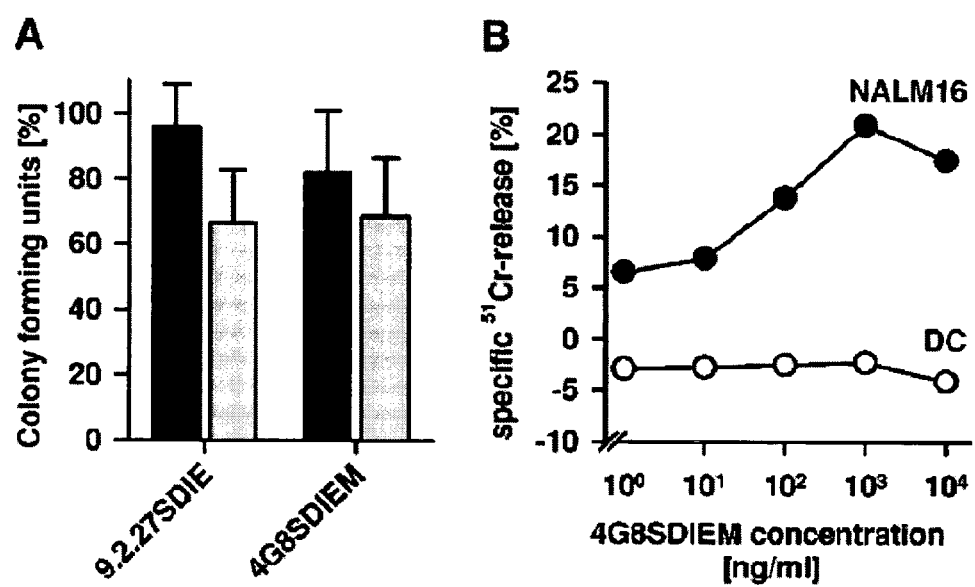
FIG. 13 shows the cytotoxic activity of 4G8SDIEM against normal cells. (A) Human bone marrow cells from two different healthy donors (black and shaded bars) were incubated with 5 µg/ml of 4G8 SDIEM and colony forming units were determined after 12 days of incubation in semi-solid medium. Numbers of CFUs were related to untreated controls. (B) DCs isolated from the PBMCs of healthy donors by magnetic cell separation and NALM16 cells were used as targets for 4G8SDIEM in a 4 hour 51[Cr] release assay (PBMC:target ratio 100:1). One representative experiment of three with DCs and autologous PBMCs from different donors is shown.

Despite the relatively low levels of 4G8SDIEM binding to normal bone marrow precursor cells and DCs, the potential toxicity of this antibody towards such cells was assessed. To this end, we incubated bone marrow cells with saturating concentrations of 4G8SDIEM and 9.2.27SDIE and determined the influence of these antibodies on the capacity of the bone marrow cells to give rise to colonies (CFUs) in semi-solid medium. No significant influence of the antibodies on CFU-forming capacity was detected in two experiments with bone marrow cells from different healthy donors (FIG. 13A). Likewise, human DCs were incubated with autologous PBMCs as effector cells. Whereas 4G8SDIEM mediated effective ADCC against NALM16 cells, used as positive control, no killing of autologous DCs was observed (FIG. 13B).

Example 12

Clinical Application of 4G8-SDIEM

Figure 14:
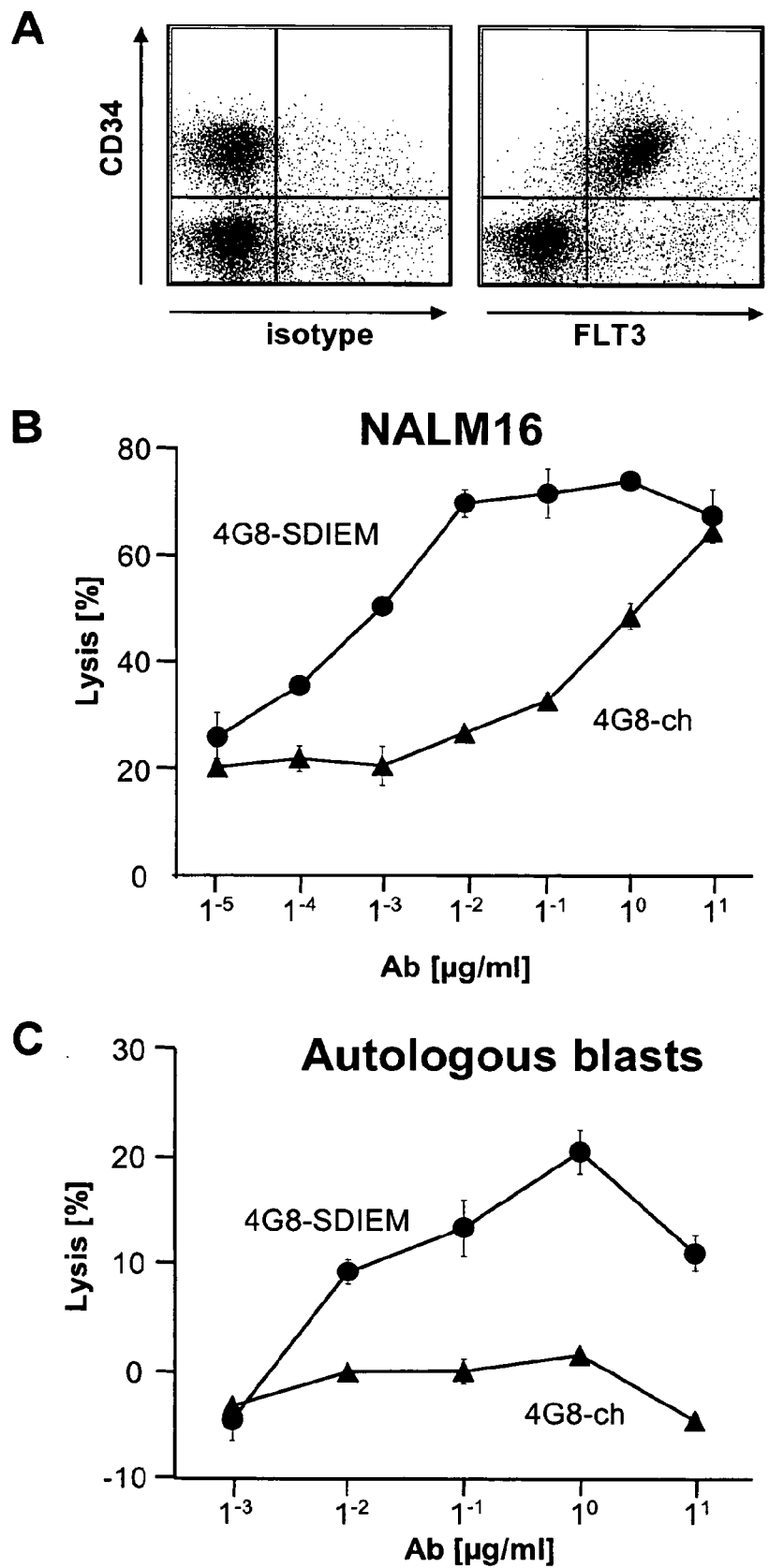
FIG. 14 shows the in vitro effects of 4G8 antibody on a patient's target and effector cells. (A) Patient PBMC were analyzed by FACS for FLT3 expression using the parental mouse 4G8 antibody and isotype control followed by anti-mouse-PE conjugate and doublestaining for CD34. (B, C) Patient PBMC were incubated with chromium labeled FLT3-positive NALM16 cells (B) or patient blasts isolated by CD34+ selection (C). Target cells were pretreated with the indicated concentrations of 4G8-SDIEM or the unmodified, chimeric 4G8 antibody (408-ch). Induction of ADCC was determined by chromium release assays at a PBMC:target ratio of 50:1. Note that PBMC and not purified NK cells were utilized.
Figure 15:
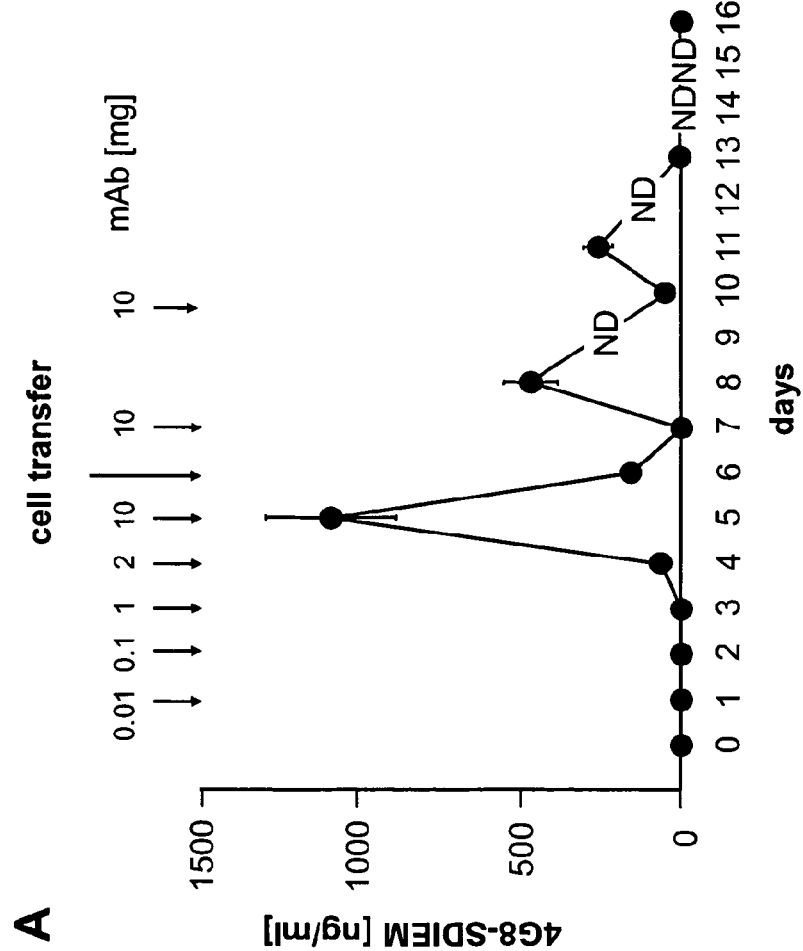
FIG. 15 shows the half life and binding characteristics of 4G8-SDIEM in vivo. (A) Serum half life of 408-SDIEM was determined by incubating FLT3-expressing NALM16 cells with serum samples obtained at different time points of clinical application. The amount of specifically bound antibody was determined by FACS and compared to binding activity of serum samples containing defined levels of 4G8-SDIEM. ND, not determined. (B) To detect 408-SDIEM binding in vivo, BM blasts obtained prior to therapy (d0) and 1 h after application of the 10 mg dose (d5) were incubated with the parental 4G8 mouse antibody, a second non-crossreactive mouse anti-FLT3 antibody (BV10) as indicated, or isotype control (open peaks) at 10 µg/ml, followed by a human-adsorbed anti-mouse-PE-conjugate. Complete inhibition of mouse-4G8 but not BV10 binding as determined by FACS indicates saturating binding of 4G8-SDIEM.
Figure 16:
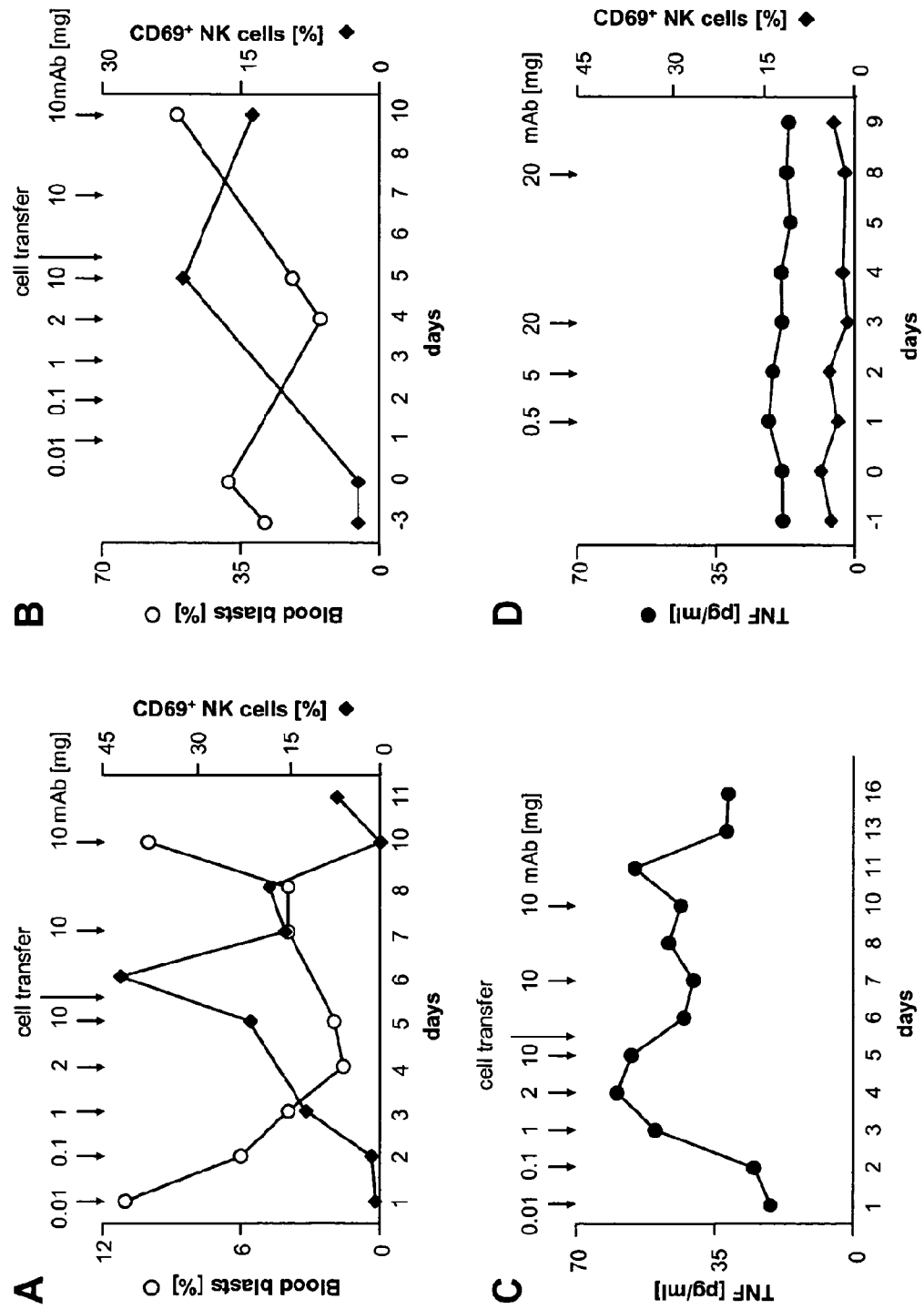
FIG. 16 shows the clinical effects of 4G8-SDIEM. (A, B) The percentages of CD34+ blasts (open cycles) and activated (CD69+) CD56+CD3− NK cells (diamonds) among mononuclear cells in peripheral blood (PB) (A) or bone marrow (BM) (B) were determined by FACS at the indicated times during treatment of overt leukemia. (C) Serum levels of TNF at the indicated times during treatment of overt leukemia were determined by IMMULITE® measurement. (D) The percentage of activated NK cells among mononuclear cells in PB (diamonds) and serum levels of TNF (circles) were determined as described above at the indicated times during application of 4G8-SDIEM in complete remission (CR).

A 30 year old male diagnosed in 2008 with AML (FAB M0, 45XY, complex kariotype including inv(3)(q21q26), −7) was treated with 4G8-SDIEM. The patient had failed to reach complete remission (CR) after two different regimes of induction therapy. Subsequently he received allogeneic SCT (stem cell transplant) from a HLA-matched donor, relapsed, received a haploidentical SCT from his sister and relapsed again. 4G8-SDIEM treatment was considered and preclinical testing performed. FACS analysis of the patients blasts (CD34+) revealed homogeneous expression of FLT3 at approximately 4000 molecules/cell (FIG. 14A and data not shown). In vitro, 4G8-SDIEM induced effective ADCC of the patient's peripheral blood mononuclear cells (PBMC) against NALM16 leukemia cells and—to a lesser extent,—against autologous blasts (FIG. 14B, C). The patient was then treated with escalating doses of 4G8-SDIEM ranging from 10 µg to 10 mg. Several hours after the first 10 mg dose, $5 \times 10^8$ CD3/CD19-depleted donor PBMCs from his sister were adoptively transferred. Serum concentration of 4G8-SDIEM reached 0.8 µg/ml 1 h after the first 10 mg dose and subsequently declined to 0.3 µg/ml at 24 h (FIG. 15A). During treatment (i) an almost complete saturation of leukemic cells in the bone marrow (BM) (FIG. 15B), (ii) a marked increase of activated NK cells in the peripheral blood (PB) (FIG. 16A) and BM (FIG. 16B) that was associated with an increase of the serum levels of the index cytokine TNF (FIG. 16C), and (iii) a marked reduction of leukemic blasts in the PB (FIG. 16A) was observed. Whereas the decline of PB blasts was transient but almost complete, reduction in the BM was less pronounced (FIG. 16B). This is most likely due to the different NK:leukemia cell ratios in the two compartments: In the PB the ratio of CD56+ NK cells and blasts was approximately 1 while that in BM was only 1/7, as determined by FACS (data not shown). Side effects of treatment were mild and consisted of subfebrile temperature (max. 38.2° C.) and a transient exacerbation of a pre-existing akneiform skin rash.

Despite the merely transient response to antibody treatment, the patient unexpectedly remained in good clinical condition for several months with slowly rising blast counts under best supportive care and hydroxyurea. Therefore, a second haploidentical SCT from a different donor was performed. After recovery, the patient had reached a CR without detectable minimal residual disease (MRD). We then applied 45.5 mg of 4G8-SDIEM in escalating doses. This time, neither relevant cytokine release nor gross NK cell activation (FIG. 16D) were observed, and side effects were completely absent.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

What is claimed is:

1. An antibody that binds human receptor tyrosine kinase FLT3, said antibody comprising a heavy chain and a light chain, the heavy chain comprising a $V_H$ CDR1 comprising or consisting of the amino acid sequence set forth in SEQ ID NO:4, a $V_H$ CDR2 comprising or consisting of the amino acid sequence set forth in SEQ ID NO:5, and a $V_H$ CDR3 region comprising or consisting of the amino acid sequence set forth in SEQ ID NO:6, and the light chain comprising a $V_L$ CDR1 comprising or consisting of the amino acid sequence set forth in SEQ ID NO:1, a $V_L$ CDR2 comprising or consisting of the amino acid sequence set forth in SEQ ID NO:2, and a $V_L$ CDR3 comprising or consisting of the amino acid sequence set forth in SEQ ID NO:3, and the amino acid substitutions S239D and I332E in the constant region relative to a parent anti-FLT3 antibody, wherein the positional numbering is according to the EU index.

2. The antibody of claim 1, wherein the antibody has antibody-dependent cell-mediated cytotoxicity (ADCC) effector function.

3. The antibody of claim 1, wherein said antibody binds with enhanced affinity to the FcγRIIIa receptor or has enhanced ADCC effector function as compared to the parent antibody.

4. The antibody of claim 1, wherein the heavy chain comprises a $V_H$ domain comprising or consisting of the amino acid sequence set forth in SEQ ID NO:14 and the light chain comprises a $V_L$ domain comprising or consisting of the amino acid sequence set forth in SEQ ID NO:13.

5. The antibody of claim 1, wherein the antibody is a chimeric antibody and comprises a heavy chain having the amino acid sequence set forth in SEQ ID NO:27 and a light chain having the amino acid sequence set forth in SEQ ID NO:23.

6. A pharmaceutical composition comprising the antibody of claim 1 and a pharmaceutically acceptable carrier.

7. A nucleic acid molecule encoding a heavy and a light chain of the antibody of claim 1.

8. The nucleic acid molecule of claim 7, wherein the nucleic acid molecule comprises a nucleotide sequence encoding the variable domain of the light chain as set forth in SEQ ID NO: 17 and wherein the nucleic acid molecule comprises a nucleotide sequence encoding the variable domain of the heavy chain as set forth in SEQ ID NO: 18.

9. The nucleic acid molecule of claim 7, wherein the nucleic acid molecule encoding the light chain of the antibody has a nucleotide sequence as set forth in SEQ ID NO: 24 and the nucleic acid molecule encoding the heavy chain of the antibody has a nucleotide sequence as set forth in SEQ ID NO:28.

10. A transfected cell line capable of producing an antibody according to claim 1.

11. An antibody that binds human receptor tyrosine kinase FLT3, said antibody comprising a heavy chain and a light chain, the light chain comprising a $V_L$ CDR1 comprising or consisting of the amino acid sequence set forth in SEQ ID NO:7; a $V_L$ CDR2 comprising or consisting of the amino acid sequence set forth in SEQ ID NO:8; a $V_L$ CDR3 comprising or consisting of the amino acid sequence set forth in SEQ ID NO:9; the heavy chain comprising a $V_H$ CDR1 comprising or consisting of the amino acid sequence set forth in SEQ ID NO:10; a $V_H$ CDR2 comprising or consisting of the amino acid sequence set forth in SEQ ID NO:11; and a $V_H$ CDR3 comprising or consisting of the amino acid sequence set forth in SEQ ID NO:12, and the amino acid substitutions S239D and I332E in the constant region relative to a parent anti-FLT3 antibody, wherein the positional numbering is according to the EU index.

12. The antibody of claim 11, wherein the antibody has antibody-dependent cell-mediated cytotoxicity (ADCC) effector function.

13. The antibody of claim 11, wherein said antibody binds with enhanced affinity to the FcγRIIIa receptor or has enhanced ADCC effector function as compared to the parent antibody.

14. The antibody of claim 11, wherein the heavy chain comprises a $V_H$ domain comprising or consisting of the amino acid sequence set forth in SEQ ID NO:30 and the light chain comprises a $V_L$ domain comprising, consisting essentially of or consisting of the amino acid sequence set forth in SEQ ID NO:29.

15. The antibody of claim 11, wherein the antibody is a chimeric antibody and comprises a heavy chain having the amino acid sequence set forth in SEQ ID NO:43 and a light chain having the amino acid sequence set forth in SEQ ID NO:39.

16. A pharmaceutical composition comprising the antibody of claim 11 and a pharmaceutically acceptable carrier.

17. A nucleic acid molecule encoding a heavy and a light chain of the antibody of claim 11.

18. The nucleic acid molecule of claim 17, wherein the nucleic acid molecule comprises a nucleotide sequence encoding the variable domain of the light chain as set forth in SEQ ID NO: 33 and wherein the nucleic acid molecule comprises a nucleotide sequence encoding the variable domain of the heavy chain as set forth in SEQ ID NO: 34.

19. The nucleic acid molecule of claim 17, wherein the nucleic acid molecule encoding the light chain of the antibody has a nucleotide sequence as set forth in SEQ ID NO: 40 and the nucleic acid molecule encoding the heavy chain of the antibody has a nucleotide sequence as set forth in SEQ ID NO:44.

20. A transfected cell line capable of producing an antibody according to claim 11.

* * * * *

```
                          SEQUENCE LISTING

<160> NUMBER OF SEQ ID NOS: 68

<210> SEQ ID NO 1
<211> LENGTH: 11
<212> TYPE: PRT
<213> ORGANISM: Artificial
<220> FEATURE:
<223> OTHER INFORMATION: 4G8 VL CDR1

<400> SEQUENCE: 1

Arg Ala Ser Gln Ser Ile Ser Asn Asn Leu His
1               5                   10

<210> SEQ ID NO 2
<211> LENGTH: 7
<212> TYPE: PRT
<213> ORGANISM: Artificial
<220> FEATURE:
<223> OTHER INFORMATION: 4G8 VL CDR2

<400> SEQUENCE: 2

Tyr Ala Ser Gln Ser Ile Ser
1               5

<210> SEQ ID NO 3
<211> LENGTH: 9
<212> TYPE: PRT
<213> ORGANISM: Artificial
<220> FEATURE:
<223> OTHER INFORMATION: 4G8 VL CDR3

<400> SEQUENCE: 3

Gln Gln Ser Asn Thr Trp Pro Tyr Thr
1               5

<210> SEQ ID NO 4
<211> LENGTH: 5
<212> TYPE: PRT
<213> ORGANISM: Artificial
<220> FEATURE:
<223> OTHER INFORMATION: 4G8 VH CDR1

<400> SEQUENCE: 4

Ser Tyr Trp Met His
1               5

<210> SEQ ID NO 5
<211> LENGTH: 17
```

```
<212> TYPE: PRT
<213> ORGANISM: Artificial
<220> FEATURE:
<223> OTHER INFORMATION: 4G8 VH CDR2

<400> SEQUENCE: 5

Glu Ile Asp Pro Ser Asp Ser Tyr Lys Asp Tyr Asn Gln Lys Phe Lys
1               5                   10                  15

Asp

<210> SEQ ID NO 6
<211> LENGTH: 9
<212> TYPE: PRT
<213> ORGANISM: Artificial
<220> FEATURE:
<223> OTHER INFORMATION: 4G8 VH CDR3

<400> SEQUENCE: 6

Ala Ile Thr Thr Thr Pro Phe Asp Phe
1               5

<210> SEQ ID NO 7
<211> LENGTH: 17
<212> TYPE: PRT
<213> ORGANISM: Artificial
<220> FEATURE:
<223> OTHER INFORMATION: BV10 VL CDR1

<400> SEQUENCE: 7

Lys Ser Ser Gln Ser Leu Leu Asn Ser Gly Asn Gln Lys Asn Tyr Met
1               5                   10                  15

Ala

<210> SEQ ID NO 8
<211> LENGTH: 7
<212> TYPE: PRT
<213> ORGANISM: Artificial
<220> FEATURE:
<223> OTHER INFORMATION: BV10 VL CDR2

<400> SEQUENCE: 8

Gly Ala Ser Thr Arg Glu Ser
1               5

<210> SEQ ID NO 9
<211> LENGTH: 9
<212> TYPE: PRT
<213> ORGANISM: Artificial
<220> FEATURE:
<223> OTHER INFORMATION: BV10 VL CDR3

<400> SEQUENCE: 9

Gln Asn Asp His Ser Tyr Pro Leu Thr
1               5

<210> SEQ ID NO 10
<211> LENGTH: 5
<212> TYPE: PRT
<213> ORGANISM: Artificial
<220> FEATURE:
<223> OTHER INFORMATION: BV10 VH CDR1

<400> SEQUENCE: 10

Asn Tyr Gly Leu His
1               5
```

```
<210> SEQ ID NO 11
<211> LENGTH: 16
<212> TYPE: PRT
<213> ORGANISM: Artificial
<220> FEATURE:
<223> OTHER INFORMATION: BV10 VH CDR2

<400> SEQUENCE: 11

Val Ile Trp Ser Gly Gly Ser Thr Asp Tyr Asn Ala Ala Phe Ile Ser
1               5                   10                  15

<210> SEQ ID NO 12
<211> LENGTH: 15
<212> TYPE: PRT
<213> ORGANISM: Artificial
<220> FEATURE:
<223> OTHER INFORMATION: BV10 VH CDR3

<400> SEQUENCE: 12

Lys Gly Gly Ile Tyr Tyr Ala Asn His Tyr Tyr Ala Met Asp Tyr
1               5                   10                  15

<210> SEQ ID NO 13
<211> LENGTH: 108
<212> TYPE: PRT
<213> ORGANISM: Artificial
<220> FEATURE:
<223> OTHER INFORMATION: 4G8 VL VJ Segment

<400> SEQUENCE: 13

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Thr Asp Phe Thr Leu Ser Ile Asn Ser Val Glu Thr
65                  70                  75                  80

Glu Asp Phe Gly Val Tyr Phe Cys Gln Gln Ser Asn Thr Trp Pro Tyr
                85                  90                  95

Thr Phe Gly Gly Gly Thr Lys Leu Glu Ile Lys Arg
            100                 105

<210> SEQ ID NO 14
<211> LENGTH: 118
<212> TYPE: PRT
<213> ORGANISM: Artificial
<220> FEATURE:
<223> OTHER INFORMATION: 4G8 VH VDJ Segment

<400> SEQUENCE: 14

Gln Val Gln Leu Gln Gln Pro Gly Ala Glu Leu Val Lys Pro Gly Ala
1               5                   10                  15

Ser Leu Lys Leu Ser Cys Lys Ser Ser Gly Tyr Thr Phe Thr Ser Tyr
                20                  25                  30

Trp Met His Trp Val Arg Gln Arg Pro Gly His Gly Leu Glu Trp Ile
            35                  40                  45

Gly Glu Ile Asp Pro Ser Asp Ser Tyr Lys Asp Tyr Asn Gln Lys Phe
        50                  55                  60
```

```
Lys Asp Lys Ala Thr Leu Thr Val Asp Arg Ser Ser Asn Thr Ala Tyr
 65                  70                  75                  80

Met His Leu Ser Ser Leu Thr Ser Asp Asp Ser Ala Val Tyr Tyr Cys
                 85                  90                  95

Ala Arg Ala Ile Thr Thr Thr Pro Phe Asp Phe Trp Gly Gln Gly Thr
            100                 105                 110

Thr Leu Thr Val Ser Ser
            115
```

<210> SEQ ID NO 15
<211> LENGTH: 234
<212> TYPE: PRT
<213> ORGANISM: Mus musculus

<400> SEQUENCE: 15

```
Met Val Phe Thr Pro Gln Ile Leu Gly Leu Met Leu Phe Trp Ile Ser
 1               5                  10                  15

Ala Ser Arg Gly Asp Ile Val Leu Thr Gln Ser Pro Ala Thr Leu Ser
             20                  25                  30

Val Thr Pro Gly Asp Ser Val Ser Leu Ser Cys Arg Ala Ser Gln Ser
         35                  40                  45

Ile Ser Asn Asn Leu His Trp Tyr Gln Gln Lys Ser His Glu Ser Pro
 50                  55                  60

Arg Leu Leu Ile Lys Tyr Ala Ser Gln Ser Ile Ser Gly Ile Pro Ser
 65                  70                  75                  80

Arg Phe Ser Gly Ser Gly Ser Gly Thr Asp Phe Thr Leu Ser Ile Asn
                 85                  90                  95

Ser Val Glu Thr Glu Asp Phe Gly Val Tyr Phe Cys Gln Gln Ser Asn
            100                 105                 110

Thr Trp Pro Tyr Thr Phe Gly Gly Gly Thr Lys Leu Glu Ile Lys Arg
            115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
            195                 200                 205

His Asn Ser Tyr Thr Cys Glu Ala Thr His Lys Thr Ser Thr Ser Pro
210                 215                 220

Ile Val Lys Ser Phe Asn Arg Asn Glu Cys
225                 230
```

<210> SEQ ID NO 16
<211> LENGTH: 461
<212> TYPE: PRT
<213> ORGANISM: Mus musculus

<400> SEQUENCE: 16

```
Met Gly Trp Ser Cys Ile Ile Leu Phe Leu Val Ser Thr Ala Thr Gly
 1               5                  10                  15

Val His Ser Gln Val Gln Leu Gln Gln Pro Gly Ala Glu Leu Val Lys
             20                  25                  30
```

```
Pro Gly Ala Ser Leu Lys Leu Ser Cys Lys Ser Ser Gly Tyr Thr Phe
            35                  40                  45
Thr Ser Tyr Trp Met His Trp Val Arg Gln Arg Pro Gly His Gly Leu
 50                  55                  60
Glu Trp Ile Gly Glu Ile Asp Pro Ser Asp Ser Tyr Lys Asp Tyr Asn
65                      70                  75                  80
Gln Lys Phe Lys Asp Lys Ala Thr Leu Thr Val Asp Arg Ser Ser Asn
                85                  90                  95
Thr Ala Tyr Met His Leu Ser Ser Leu Thr Ser Asp Asp Ser Ala Val
                100                 105                 110
Tyr Tyr Cys Ala Arg Ala Ile Thr Thr Thr Pro Phe Asp Phe Trp Gly
            115                 120                 125
Gln Gly Thr Thr Leu Thr Val Ser Ser Ala Lys Thr Thr Pro Pro Ser
    130                 135                 140
Val Tyr Pro Leu Ala Pro Gly Ser Ala Ala Gln Thr Asn Ser Met Val
145                 150                 155                 160
Thr Leu Gly Cys Leu Val Lys Gly Tyr Phe Pro Glu Pro Val Thr Val
                165                 170                 175
Thr Trp Asn Ser Gly Ser Leu Ser Ser Gly Val His Thr Phe Pro Ala
                180                 185                 190
Val Leu Gln Ser Asp Leu Tyr Thr Leu Ser Ser Ser Val Thr Val Pro
            195                 200                 205
Ser Ser Thr Trp Pro Ser Glu Thr Val Thr Cys Asn Val Ala His Pro
    210                 215                 220
Ala Ser Ser Thr Lys Val Asp Lys Lys Ile Val Pro Arg Asp Cys Gly
225                 230                 235                 240
Cys Lys Pro Cys Ile Cys Thr Val Pro Glu Val Ser Ser Val Phe Ile
                245                 250                 255
Phe Pro Pro Lys Pro Lys Asp Val Leu Thr Ile Thr Leu Thr Pro Lys
                260                 265                 270
Val Thr Cys Val Val Asp Ile Ser Lys Asp Asp Pro Glu Val Gln
            275                 280                 285
Phe Ser Trp Phe Val Asp Asp Val Glu Val His Thr Ala Gln Thr Gln
    290                 295                 300
Pro Arg Glu Glu Gln Phe Asn Ser Thr Phe Arg Ser Val Ser Glu Leu
305                 310                 315                 320
Pro Ile Met His Gln Asp Trp Leu Asn Gly Lys Glu Phe Lys Cys Arg
                325                 330                 335
Val Asn Ser Ala Ala Phe Pro Ala Pro Ile Glu Lys Thr Ile Ser Lys
                340                 345                 350
Thr Lys Gly Arg Pro Lys Ala Pro Gln Val Tyr Thr Ile Pro Pro Pro
            355                 360                 365
Lys Glu Gln Met Ala Lys Asp Lys Val Ser Leu Thr Cys Met Ile Thr
    370                 375                 380
Asp Phe Phe Pro Glu Asp Ile Thr Val Glu Trp Gln Trp Asn Gly Gln
385                 390                 395                 400
Pro Ala Glu Asn Tyr Lys Asn Thr Gln Pro Ile Met Asp Thr Asp Gly
                405                 410                 415
Ser Tyr Phe Val Tyr Ser Lys Leu Asn Val Gln Lys Ser Asn Trp Glu
                420                 425                 430
Ala Gly Asn Thr Phe Thr Cys Ser Val Leu His Glu Gly Leu His Asn
            435                 440                 445
```

His His Thr Glu Lys Ser Leu Ser His Ser Pro Gly Lys
    450                 455                 460

<210> SEQ ID NO 17
<211> LENGTH: 324
<212> TYPE: DNA
<213> ORGANISM: Artificial
<220> FEATURE:
<223> OTHER INFORMATION: 4G8 VL VJ Segment CDS

<400> SEQUENCE: 17
gatattgtgc taactcagtc tccagccacc ctgtctgtga ctccaggaga tagcgtcagt      60
ctttcctgca gggccagcca gagtattagc aacaacctac actggtatca acaaaaatca     120
catgagtctc caaggcttct catcaagtat gcttcccagt ccatctctgg atcccctcc      180 aggttcagtg gcagtggatc aggacagat ttcactctca gtatcaacag tgtggagact      240
gaagattttg gagtgtattt ctgtcaacag agtaacacct ggccgtacac gttcggaggg     300
gggaccaagc tggaaataaa acgg                                            324

<210> SEQ ID NO 18
<211> LENGTH: 354
<212> TYPE: DNA
<213> ORGANISM: Artificial
<220> FEATURE:
<223> OTHER INFORMATION: 4G8 VH VDJ Segment CDS

<400> SEQUENCE: 18
caggtccaac tgcagcagcc tggggctgag cttgtgaagc ctggggcttc attgaagctg      60
tcctgcaagt cttccgggta ccttcacc agctactgga tgcactgggt gaggcagagg       120
cctggacatg ccttgagtg gatcggagag attgatcctt ctgacagtta taaagactac      180
aatcagaagt tcaaggacaa ggccacattg actgtggaca gatcctccaa cacagcctac     240
atgcacctca gcagcctgac atctgatgac tctgcggtct attattgtgc aagagcgatt     300
acgacgaccc cctttgactt ctgggggccaa ggcaccactc tcacagtctc ctca          354

<210> SEQ ID NO 19
<211> LENGTH: 705
<212> TYPE: DNA
<213> ORGANISM: Mus musculus

<400> SEQUENCE: 19
atggttttca cacctcagat acttggactt atgcttttt ggatttcagc ctccagaggt       60
gatattgtgc taactcagtc tccagccacc ctgtctgtga ctccaggaga tagcgtcagt     120
ctttcctgca gggccagcca gagtattagc aacaacctac actggtatca acaaaaatca    180
catgagtctc caaggcttct catcaagtat gcttcccagt ccatctctgg atcccctcc     240 aggttcagtg gcagtggatc aggacagat ttcactctca gtatcaacag tgtggagact    300
gaagattttg gagtgtattt ctgtcaacag agtaacacct ggccgtacac gttcggaggg    360
gggaccaagc tggaaataaa acgggctgat gctgcaccaa ctgtatccat cttcccacca    420
tccagtgagc agttaacatc tggaggtgcc tcagtcgtgt gcttcttgaa caacttctac    480
cccaaagaca tcaatgtcaa gtggaagatt gatggcagtg aacgacaaaa tggcgtcctg    540
aacagttgga ctgatcagga cagcaaagac agcacctaca gcatgagcag caccctcacg    600
ttgaccaagg acgagtatga acgacataac agctataccct gtgaggccac tcacaagaca    660
tcaacttcac ccattgtcaa gagcttcaac aggaatgagt gttag                     705

<210> SEQ ID NO 20
<211> LENGTH: 948
<212> TYPE: DNA
<213> ORGANISM: Mus musculus

<400> SEQUENCE: 20

```
ctcagggaaa gctcgaagat ggttttcaca cctcagatac ttggacttat gcttttttgg      60
atttcagcct ccagaggtga tattgtgcta actcagtctc cagccaccct gtctgtgact     120
ccaggagata gcgtcagtct ttcctgcagg gccagccaga gtattagcaa caacctacac     180
tggtatcaac aaaaatcaca tgagtctcca aggcttctca tcaagtatgc ttcccagtcc     240
atctctggga tcccctccag gttcagtggc agtggatcag ggacagattt cactctcagt     300
atcaacagtg tggagactga agattttgga gtgtatttct gtcaacagag taacacctgg     360
ccgtacacgt tcggaggggg gaccaagctg gaaataaaac gggctgatgc tgcaccaact     420
gtatccatct ccccaccatc cagtgagcag ttaacatctg gaggtgcctc agtcgtgtgc     480
ttcttgaaca acttctaccc caaagacatc aatgtcaagt ggaagattga tggcagtgaa     540
cgacaaaatg gcgtcctgaa cagttggact gatcaggaca gcaaagacag cacctacagc     600
atgagcagca ccctcacgtt gaccaaggac gagtatgaac acataacag ctatacctgt      660
gaggccactc acaagacatc aacttcaccc attgtcaaga gcttcaacag gaatgagtgt     720
tagagacaaa ggtcctgaga cgccaccacc agctccccag ctccatccta tcttcccttc     780
taaggtcttg gaggcttccc cacaagcgac ctaccactgt tgcggtgctc caaacctcct     840
ccccacctcc ttctcctcct cctcccttc cttggctttt atcatgctaa tatttgcaga     900
aaatattcaa taaagtgagt ctttgcactt gaaaaaaaaa aaaaaaaa                 948
```

<210> SEQ ID NO 21
<211> LENGTH: 1386
<212> TYPE: DNA
<213> ORGANISM: Mus musculus

<400> SEQUENCE: 21

```
atgggatgga gctgtatcat cctcttcttg gtatcaacag ctacaggtgt ccactcccag      60
gtccaactgc agcagcctgg ggctgagctt gtgaagcctg ggcttcatt gaagctgtcc      120
tgcaagtctt ccgggtacac cttcaccagc tactggatgc actgggtgag cagaggcct     180
ggacatggcc ttgagtggat cggagagatt gatccttctg acagttataa agactacaat     240
cagaagttca aggacaaggc cacattgact gtggacagat cctccaacac agcctacatg     300
cacctcagca gcctgacatc tgatgactct gcggtctatt attgtgcaag agcgattacg     360
acgaccccct ttgacttctg gggccaaggc accactctca cagtctcctc agccaaaacg     420
acacccccat ctgtctatcc actggcccct ggatctgctg cccaaactaa ctccatggtg     480
accctgggat gcctggtcaa gggctatttc cctgagccag tgacagtgac ctggaactct     540
ggatccctgt ccagcggtgt gcacaccttc ccagctgtcc tgcagtctga cctctacact     600
ctgagcagct cagtgactgt cccctccagc acctggccca gcgagaccgt cacctgcaac     660
gttgcccacc cggccagcag caccaaggtg gacaagaaaa ttgtgcccag ggattgtggt     720
tgtaagcctt gcatatgtac agtcccagaa gtatcatctg tcttcatctt ccccccaaag     780
cccaaggatg tgctcaccat tactctgact cctaaggtca cgtgtgttgt ggtagacatc     840
agcaaggatg atcccgaggt ccagttcagc tggtttgtag atgatgtgga ggtgcacaca     900
gctcagacgc aaccccggga ggagcagttc aacagcactt tccgctcagt cagtgaactt     960
```

```
cccatcatgc accaggactg gctcaatggc aaggagttca aatgcagggt caacagtgca    1020
gctttccctg cccccatcga gaaaaccatc tccaaaacca aaggcagacc gaaggctcca    1080
caggtgtaca ccattccacc tcccaaggag cagatggcca aggataaagt cagtctgacc    1140
tgcatgataa cagacttctt ccctgaagac attactgtgg agtggcagtg aatgggcag    1200 ccagcggaga actacaagaa cactcagccc atcatggaca cagatggctc ttacttcgtc    1260
tacagcaagc tcaatgtgca aagagcaac tgggaggcag aaatacttt cacctgctct    1320 gtgttacatg agggcctgca aaccaccat actgagaaga gcctctccca ctctcctggt    1380
aaatga                                                              1386

<210> SEQ ID NO 22
<211> LENGTH: 1593
<212> TYPE: DNA
<213> ORGANISM: Mus musculus

<400> SEQUENCE: 22
gttcgttatc ggaattaacc agacaaatcg ctccaccaac taagaacggc cctgttctct      60
ctacagttac tgagcacaca ggacctcacc atgggatgga gctgtatcat cctcttcttg     120
gtatcaacag ctacaggtgt ccactcccag gtccaactgc agcagcctgg ggctgagctt     180
gtgaagcctg ggcttcatt gaagctgtcc tgcaagtctt ccgggtacac cttcaccagc     240
tactggatgc actgggtgag gcagaggcct ggacatggcc ttgagtggat cggagagatt     300
gatccttctg acagttataa agactacaat cagaagttca aggacaaggc cacattgact     360
gtggacagat cctccaacac agcctacatg cacctcagca gcctgacatc tgatgactct     420
gcggtctatt attgtgcaag agcgattacg acgacccct ttgacttctg ggccaaggc      480 accactctca cagtctcctc agccaaaacg acaccccat ctgtctatcc actggcccct     540
ggatctgctg cccaaactaa ctccatggtg accctgggat gcctggtcaa gggctatttc     600
cctgagccag tgacagtgac ctggaactct ggatccctgt ccagcggtgt gcacaccttc     660
ccagctgtcc tgcagtctga cctctacact ctgagcagct cagtgactgt cccctccagc     720
acctggccca gcgagaccgt cacctgcaac gttgcccacc cggccagcag caccaaggtg     780
gacaagaaaa ttgtgcccag ggattgtggt tgtaagcctt gcatatgtac agtcccagaa     840
gtatcatctg tcttcatctt ccccccaaag cccaaggatg tgctcaccat tactctgact     900
cctaaggtca cgtgtgttgt ggtagacatc agcaaggatg atcccgaggt ccagttcagc     960
tggtttgtag atgatgtgga ggtgcacaca gctcagacgc aaccccggga ggagcagttc    1020
aacagcactt tccgctcagt cagtgaactt cccatcatgc accaggactg gctcaatggc    1080
aaggagttca aatgcagggt caacagtgca gctttccctg cccccatcga gaaaaccatc    1140
tccaaaacca aaggcagacc gaaggctcca caggtgtaca ccattccacc tcccaaggag    1200
cagatggcca aggataaagt cagtctgacc tgcatgataa cagacttctt ccctgaagac    1260
attactgtgg agtggcagtg aatgggcag ccagcggaga actacaagaa cactcagccc    1320
atcatggaca cagatggctc ttacttcgtc tacagcaagc tcaatgtgca aagagcaac    1380 tgggaggcag aaatacttt cacctgctct gtgttacatg agggcctgca aaccaccat    1440 actgagaaga gcctctccca ctctcctggt aaatgatccc agtgtccttg gagccctctg    1500
gtcctacagg actctgacac ctacctccac ccctccctgt ataaataaag cacccagcac    1560
tgccttggga ccctgcaaaa aaaaaaaaaa aaa                                 1593
```

<210> SEQ ID NO 23
<211> LENGTH: 234
<212> TYPE: PRT
<213> ORGANISM: Artificial
<220> FEATURE:
<223> OTHER INFORMATION: 4G8 chimeric kappa light chain

<400> SEQUENCE: 23

```
Met Val Phe Thr Pro Gln Ile Leu Gly Leu Met Leu Phe Trp Ile Ser
1               5                   10                  15

Gly Ala Arg Gly Asp Ile Val Leu Thr Gln Ser Pro Ala Thr Leu Ser
            20                  25                  30

Val Thr Pro Gly Asp Ser Val Ser Leu Ser Cys Arg Ala Ser Gln Ser
        35                  40                  45

Ile Ser Asn Asn Leu His Trp Tyr Gln Gln Lys Ser His Glu Ser Pro
    50                  55                  60

Arg Leu Leu Ile Lys Tyr Ala Ser Gln Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Thr Glu Asp Phe Val Tyr Phe Cys Gln Gln Ser Asn
            100                 105                 110

Thr Trp Pro Tyr Thr Phe Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 24
<211> LENGTH: 705
<212> TYPE: DNA
<213> ORGANISM: Artificial
<220> FEATURE:
<223> OTHER INFORMATION: 4G8 chimeric kappa light chain CDS

<400> SEQUENCE: 24

```
atggttttca cacctcagat acttggactt atgcttttt ggatttcagg tgctcgagga      60
gatattgtgc taactcagtc tccagccacc ctgtctgtga ctccaggaga tagcgtcagt    120
ctttcctgca gggccagcca gagtattagc aacaacctac actggtatca acaaaaatca    180
catgagtctc caaggcttct catcaagtat gcttcccagt ccatctctgg atcccctcc    240 aggttcagtg gcagtggatc aggacagat tcactctca gtatcaacag tgtggagact      300
gaagattttg gagtgtattt ctgtcaacag agtaacacct ggccgtacac gttcggaggg    360
gggaccaagc tggaaataaa acggactgtg gctgcaccat ctgtcttcat cttcccgcca    420
```

-continued

```
tctgatgagc agttgaaatc tggaactgcc tctgttgtgt gcctgctgaa taacttctat    480
cccagagagg ccaaagtaca gtggaaggtg ataacgccc tccaatcggg taactcccag     540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gttag                   705
```

<210> SEQ ID NO 25
<211> LENGTH: 467
<212> TYPE: PRT
<213> ORGANISM: Artificial
<220> FEATURE:
<223> OTHER INFORMATION: 4G8 chimeric IgG gamma 1 heavy chain

<400> SEQUENCE: 25

```
Met Gly Trp Ser Trp Ile Phe Leu Phe Leu Leu Ser Gly Thr Ala Gly
1               5                   10                  15

Val Leu Ser Gln Val Gln Leu Gln Gln Pro Gly Ala Glu Leu Val Lys
            20                  25                  30

Pro Gly Ala Ser Leu Lys Leu Ser Cys Lys Ser Ser Gly Tyr Thr Phe
        35                  40                  45

Thr Ser Tyr Trp Met His Trp Val Arg Gln Arg Pro Gly His Gly Leu
    50                  55                  60

Glu Trp Ile Gly Glu Ile Asp Pro Ser Asp Ser Tyr Lys Asp Tyr Asn
65                  70                  75                  80

Gln Lys Phe Lys Asp Lys Ala Thr Leu Thr Val Asp Arg Ser Ser Asn
                85                  90                  95

Thr Ala Tyr Met His Leu Ser Ser Leu Thr Ser Asp Asp Ser Ala Val
            100                 105                 110

Tyr Tyr Cys Ala Arg Ala Ile Thr Thr Thr Pro Phe Asp Phe Trp Gly
        115                 120                 125

Gln Gly Thr Thr Leu Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320
```

```
Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
        340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 26
<211> LENGTH: 1407
<212> TYPE: DNA
<213> ORGANISM: Artificial
<220> FEATURE:
<223> OTHER INFORMATION: 4G8 chimeric IgG gamma 1 heavy chain CDS

<400> SEQUENCE: 26
atgggatgga gctggatctt tctctttctc ctgtcaggaa ctgcaggtgt cctctctcag    60
gtccaactgc agcagcctgg ggctgagctt gtgaagcctg ggcttcatt gaagctgtcc    120 tgcaagtctt ccgggtacac cttcaccagc tactggatgc actgggtgag gcagaggcct    180
ggacatggcc ttgagtggat cggagagatt gatccttctg acagttataa agactacaat    240
cagaagttca aggacaaggc acattgact gtggacagat cctccaacac agcctacatg    300
cacctcagca gcctgacatc tgatgactct gcggtctatt attgtgcaag agcgattacg    360
acgaccccct ttgacttctg gggccaaggc accactctca gtctcctc agcctccacc    420 aagggcccat cggtcttccc cctggcaccc tcctccaaga gcacctctgg gggcacagcg    480
gccctgggct gtctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt    720 gacaaaactc acacatgccc accgtgccca gcacctgaac tcctgggggg accgtcagtc    780
ttcctcttcc cccaaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtat    960
cgtgtggtca gcgtcctcac cgtcctgcac caggactggc tgaatggcaa ggagtacaag   1020
tgcaaggtct ccaacaaagc cctcccagcc ccatcgaga aaaccatctc caaagccaaa   1080
gggcagcccc gagaaccaca ggtgtacacc ctgccccat cccgggatga gctgaccaag   1140
```

```
aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta cagcaagctc accgtggaca agagcaggtg gcagcagggg    1320
aacgtcttct catgctccgt gatgcatgag gctctgcaca accactacac gcagaagagc    1380
ctctccctgt ctccgggtaa atgataa                                        1407
```

<210> SEQ ID NO 27
<211> LENGTH: 467
<212> TYPE: PRT
<213> ORGANISM: Artificial
<220> FEATURE:
<223> OTHER INFORMATION: SDIE 4G8 heavy chain

<400> SEQUENCE: 27

```
Met Gly Trp Ser Trp Ile Phe Leu Phe Leu Leu Ser Gly Thr Ala Gly
1               5                   10                  15

Val Leu Ser Gln Val Gln Leu Gln Gln Pro Gly Ala Glu Leu Val Lys
            20                  25                  30

Pro Gly Ala Ser Leu Lys Leu Ser Cys Lys Ser Ser Gly Tyr Thr Phe
        35                  40                  45

Thr Ser Tyr Trp Met His Trp Val Arg Gln Arg Pro Gly His Gly Leu
    50                  55                  60

Glu Trp Ile Gly Glu Ile Asp Pro Ser Asp Ser Tyr Lys Asp Tyr Asn
65                  70                  75                  80

Gln Lys Phe Lys Asp Lys Ala Thr Leu Thr Val Asp Arg Ser Ser Asn
                85                  90                  95

Thr Ala Tyr Met His Leu Ser Ser Leu Thr Ser Asp Asp Ser Ala Val
            100                 105                 110

Tyr Tyr Cys Ala Arg Ala Ile Thr Thr Thr Pro Phe Asp Phe Trp Gly
        115                 120                 125

Gln Gly Thr Thr Leu Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Asp Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320
```

```
Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Glu
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 28
<211> LENGTH: 1407
<212> TYPE: DNA
<213> ORGANISM: Artificial
<220> FEATURE:
<223> OTHER INFORMATION: SDIE 4G8 heavy chain CDS

<400> SEQUENCE: 28
atgggatgga gctggatctt tctctttctc ctgtcaggaa ctgcaggtgt cctctctcag      60
gtccaactgc agcagcctgg ggctgagctt gtgaagcctg gggcttcatt gaagctgtcc     120
tgcaagtctt ccgggtacac cttcaccagc tactggatgc actgggtgag gcagaggcct     180
ggacatggcc ttgagtggat cggagagatt gatccttctg acagttataa agactacaat     240
cagaagttca aggacaaggc acattgact gtggacagat cctccaacac agcctacatg      300
cacctcagca gcctgacatc tgatgactct gcggtctatt attgtgcaag agcgattacg     360
acgaccccct ttgacttctg gggccaaggc accactctca gtctcctc agcctccacc       420 aagggcccat cggtcttccc cctggcaccc tcctccaaga gcacctctgg gggcacagcg     480
gccctgggct gtctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcagcttgg gcacccagac ctacatctgc     660
aacgtgaatc acaagcccag caacaccaag gtggacaaga agttgagcc caaatcttgt     720 gacaaaactc acacatgccc accgtgccca gcacctgaac tcctgggggg accggatgtc     780
ttcctcttcc ccccaaaacc caaggacacc ctcatgatct cccggacccc tgaggtcaca     840
tgcgtggtgg tggacgtgag ccacgaagac cctgaggtca agttcaactg gtacgtggac     900
ggcgtggagg tgcataatgc caagacaaag ccgcgggagg agcagtacaa cagcacgtat     960
cgtgtggtca gcgtcctcac cgtcctgcac caggactggc tgaatggcaa ggagtacaag    1020
tgcaaggtct ccaacaaagc cctcccagcc ccgaggaga aaaccatctc caaagccaaa     1080
gggcagcccc gagaaccaca ggtgtacacc ctgcccccat cccgggatga gctgaccaag    1140
```

```
aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta cagcaagctc accgtggaca agagcaggtg gcagcagggg    1320
aacgtcttct catgctccgt gatgcatgag gctctgcaca accactacac gcagaagagc    1380
ctctccctgt ctccgggtaa atgataa                                         1407
```

<210> SEQ ID NO 29
<211> LENGTH: 113
<212> TYPE: PRT
<213> ORGANISM: Artificial
<220> FEATURE:
<223> OTHER INFORMATION: BV10 VL VJ Segment

<400> SEQUENCE: 29

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Met Ala Tyr Gln Gln Lys Pro Gly Gln Pro
        35                  40                  45

Pro Lys Leu Leu Ile Tyr Gly Ala Ser Thr Arg Glu Ser Gly Val Pro
    50                  55                  60

Asp Arg Phe Thr Gly Ser Gly Ser Gly Thr Asp Phe Thr Leu Thr Ile
65                  70                  75                  80

Ser Ser Val Gln Ala Glu Asp Leu Ala Val Tyr Tyr Cys Gln Asn Asp
                85                  90                  95

His Ser Tyr Pro Leu Thr Phe Gly Ala Gly Thr Lys Leu Glu Leu Lys
            100                 105                 110

Arg

<210> SEQ ID NO 30
<211> LENGTH: 123
<212> TYPE: PRT
<213> ORGANISM: Artificial
<220> FEATURE:
<223> OTHER INFORMATION: BV10 VH VDJ Segment

<400> SEQUENCE: 30

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Leu His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Lys Gly Gly Ile Tyr Tyr Ala Asn His Tyr Tyr Ala Met Asp Tyr
            100                 105                 110

Trp Gly Gln Gly Thr Ser Val Thr Val Ser Ser
        115                 120

<210> SEQ ID NO 31

-continued

```
<211> LENGTH: 240
<212> TYPE: PRT
<213> ORGANISM: Mus musculus

<400> SEQUENCE: 31

Met Glu Ser Gln Thr Gln Val Leu Ile Ser Leu Leu Phe Trp Val Ser
1               5                   10                  15

Gly Thr Cys Gly Asp Ile Val Met Thr Gln Ser Pro Ser Ser Leu Ser
            20                  25                  30

Val Ser Ala Gly Glu Lys Val Thr Met Ser Cys Lys Ser Ser Gln Ser
        35                  40                  45

Leu Leu Asn Ser Gly Asn Gln Lys Asn Tyr Met Ala Trp Tyr Gln Gln
    50                  55                  60

Lys Pro Gly Gln Pro Pro Lys Leu Leu Ile Tyr Gly Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Asn Asp His Ser Tyr Pro Leu Thr Phe Gly Ala Gly Thr
        115                 120                 125

Lys Leu Glu Leu Lys Arg Ala Asp Ala Ala Pro Thr Val Ser Ile Phe
    130                 135                 140

Pro Pro Ser Ser Glu Gln Leu Thr Ser Gly Gly Ala Ser Val Val Cys
145                 150                 155                 160

Phe Leu Asn Asn Phe Tyr Pro Lys Asp Ile Asn Val Lys Trp Lys Ile
                165                 170                 175

Asp Gly Ser Glu Arg Gln Asn Gly Val Leu Asn Ser Trp Thr Asp Gln
            180                 185                 190

Asp Ser Lys Asp Ser Thr Tyr Ser Met Ser Ser Thr Leu Thr Leu Thr
        195                 200                 205

Lys Asp Glu Tyr Glu Arg His Asn Ser Tyr Thr Cys Glu Ala Thr His
    210                 215                 220

Lys Thr Ser Thr Ser Pro Ile Val Lys Ser Phe Asn Arg Asn Glu Cys
225                 230                 235                 240

<210> SEQ ID NO 32
<211> LENGTH: 466
<212> TYPE: PRT
<213> ORGANISM: Artificial
<220> FEATURE:
<223> OTHER INFORMATION: BV10 IgG gamma 1 heavy chain mouse

<400> SEQUENCE: 32

Met Ala Val Leu Gly Leu Leu Phe Cys Leu Val Thr Phe Pro Ser Cys
1               5                   10                  15

Val Leu Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Asn Tyr Gly Leu His Trp Val Arg Gln Ser Pro Gly Lys Gly Leu
    50                  55                  60

Glu Trp Leu Gly Val Ile Trp Ser Gly Gly Ser Thr Asp Tyr Asn Ala
65                  70                  75                  80

Ala Phe Ile Ser Arg Leu Ser Ile Ser Lys Asp Asn Ser Lys Ser Gln
                85                  90                  95
```

Val Phe Phe Lys Met Asn Ser Leu Gln Ala Asp Asp Thr Ala Ile Tyr
            100                 105                 110

Tyr Cys Ala Arg Lys Gly Gly Ile Tyr Tyr Ala Asn His Tyr Tyr Ala
        115                 120                 125

Met Asp Tyr Trp Gly Gln Gly Thr Ser Val Thr Val Ser Ser Ala Lys
130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
            165                 170                 175

Glu Pro Val Thr Val Thr Trp Asn Ser Gly Ser Leu Ser Ser Gly Val
            180                 185                 190

His Thr Phe Pro Ala Val Leu Glu Ser Asp Leu Tyr Thr Leu Ser Ser
            195                 200                 205

Ser Val Thr Val Pro Ser Ser Pro Arg Pro Ser Glu Thr Val Thr Cys
            210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
            245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
            275                 280                 285

Asp Pro Glu Val Gln Phe Ser Trp Phe Val Asp Val Glu Val His
            290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
            325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
            355                 360                 365

Thr Ile Pro Pro Pro Lys Glu Gln Met Ala Lys Asp Lys Val Ser Leu
370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
            405                 410                 415

Met Asn Thr Asn Gly Ser Tyr Phe Val Tyr Ser Lys Leu Asn Val Gln
            420                 425                 430

Lys Ser Asn Trp Glu Ala Gly Asn Thr Phe Thr Cys Ser Val Leu His
            435                 440                 445

Glu Gly Leu His Asn His His Thr Glu Lys Ser Leu Ser His Ser Pro
            450                 455                 460

Gly Lys
465

<210> SEQ ID NO 33
<211> LENGTH: 342
<212> TYPE: DNA
<213> ORGANISM: Artificial
<220> FEATURE:
<223> OTHER INFORMATION: BV10 VL VJ Segment CDS

<400> SEQUENCE: 33

```
gacattgtga tgacacagtc tccatcctcc ctgagtgtgt cagcaggaga gaaggtcact    60
atgagctgca agtccagtca gagtctgtta aacagtggaa atcaaaagaa ctatatggcc   120
tggtatcagc agaaaccagg gcagcctcct aaactgttga tctacggggc atccactagg   180
gaatctgggg tccctgatcg cttcacaggc agtggatctg gaaccgattt cactcttacc   240
atcagcagtg tgcaggctga agacctggca gtttattact gtcagaatga tcatagttat   300
ccgctcacgt tcggtgctgg gaccaagctg gagctgaaac gg                     342
```

<210> SEQ ID NO 34
<211> LENGTH: 369
<212> TYPE: DNA
<213> ORGANISM: Artificial
<220> FEATURE:
<223> OTHER INFORMATION: BV10 VH VDJ Segment CDS

<400> SEQUENCE: 34

```
caggtgcagc tgaagcagtc aggacctggc ctagtgcagc cctcacagag cctgtccatc    60
acctgcacag tctctggttt ctcattaact aactatggtt tacactgggt tcgccagtct   120
ccaggaaagg gcctggagtg gctgggagtg atatggagtg gtggaagcac agactataat   180
gcagctttca tatccagact gagcatcagc aaggacaact ccaagagcca agttttcttt   240
aaaatgaaca gtctgcaggc tgatgacaca gccatatact actgtgccag aaaaggaggg   300
atctactatg ctaaccatta ctatgctatg gactactggg gtcaaggaac ctcagtcacc   360
gtctcctca                                                           369
```

<210> SEQ ID NO 35
<211> LENGTH: 723
<212> TYPE: DNA
<213> ORGANISM: Mus musculus

<400> SEQUENCE: 35

```
atggaatcac agactcaggt cctcatctcc ttgctgttct gggtatctgg tacctgtggg    60
gacattgtga tgacacagtc tccatcctcc ctgagtgtgt cagcaggaga gaaggtcact   120
atgagctgca agtccagtca gagtctgtta aacagtggaa atcaaaagaa ctatatggcc   180
tggtatcagc agaaaccagg gcagcctcct aaactgttga tctacggggc atccactagg   240
gaatctgggg tccctgatcg cttcacaggc agtggatctg gaaccgattt cactcttacc   300
atcagcagtg tgcaggctga agacctggca gtttattact gtcagaatga tcatagttat   360
ccgctcacgt tcggtgctgg gaccaagctg gagctgaaac gggctgatgc tgcaccaact   420
gtatccatct tcccaccatc cagtgagcag ttaacatctg gaggtgcctc agtcgtgtgc   480
ttcttgaaca acttctaccc caaagacatc aatgtcaagt ggaagattga tggcagtgaa   540
cgacaaaatg gcgtcctgaa cagttggact gatcaggaca gcaaagacag cacctacagc   600
atgagcagca ccctcacgtt gaccaaggac gagtatgaac gacataacag ctatacctgt   660
gaggccactc acaagacatc aacttcaccc attgtcaaga gcttcaacag gaatgagtgt   720
tag                                                                 723
```

<210> SEQ ID NO 36
<211> LENGTH: 907
<212> TYPE: DNA
<213> ORGANISM: Mus musculus

<400> SEQUENCE: 36

```
atggaatcac agactcaggt cctcatctcc ttgctgttct gggtatctgg tacctgtggg      60
gacattgtga tgacacagtc tccatcctcc ctgagtgtgt cagcaggaga gaaggtcact     120
atgagctgca agtccagtca gagtctgtta aacagtggaa atcaaaagaa ctatatggcc     180
tggtatcagc agaaaccagg gcagcctcct aaactgttga tctacggggc atccactagg     240
gaatctgggg tccctgatcg cttcacaggc agtggatctg gaaccgattt cactcttacc     300
atcagcagtg tgcaggctga agacctggca gtttattact gtcagaatga tcatagttat     360
ccgctcacgt tcggtgctgg gaccaagctg gagctgaaac gggctgatgc tgcaccaact     420
gtatccatct tcccaccatc cagtgagcag ttaacatctg gaggtgcctc agtcgtgtgc     480
ttcttgaaca acttctaccc caaagacatc aatgtcaagt ggaagattga tggcagtgaa     540
cgacaaaatg gcgtcctgaa cagttggact gatcaggaca gcaaagacag cacctacagc     600
atgagcagca ccctcacgtt gaccaaggac gagtatgaac gacataacag ctatacctgt     660
gaggccactc acaagacatc aacttcaccc attgtcaaga gcttcaacag gaatgagtgt     720
tagagacaaa ggtcctgaga cgccaccacc agctccccag ctccatccta tcttcccttc     780
taaggtcttg gaggcttccc cacaagcgac ctaccactgt gcggtgctc caaacctcct      840
ccccacctcc ttctcctcct cctcccttc cttggctttt atcatgctaa tatttgcatg       900
ataaaaa                                                                907
```

<210> SEQ ID NO 37
<211> LENGTH: 1401
<212> TYPE: DNA
<213> ORGANISM: Mus musculus

<400> SEQUENCE: 37

```
atggctgtct tggggctgct cttctgcctg gtgacattcc caagctgtgt cctctcccag      60
gtgcagctga agcagtcagg acctggccta gtgcagccct cacagagcct gtccatcacc     120
tgcacagtct ctggtttctc attaactaac tatggtttac actgggttcg ccagtctcca     180
ggaaagggcc tggagtggct gggagtgata tggagtggtg aagcacaga ctataatgca       240
gctttcatat ccagactgag catcagcaag acaactccca agagccaagt tttctttaaa     300
atgaacagtc tgcaggctga tgacacagcc atatactact gtgccagaaa aggagggatc     360
tactatgcta accattacta tgctatggac tactggggtc aaggaacctc agtcaccgtc     420
tcctcagcca aaacgacacc cccatctgtc tatccactgg cccctggatc tgctgcccaa     480
actaactcca tggtgaccct gggatgcctg gtcaagggct atttccctga gccagtgaca     540
gtgacctgga actctggatc cctgtccagc ggtgtgcaca ccttcccagc tgtcctggag     600
tctgacctct acactctgag cagctcagtg actgtcccct ccagccctcg gcccagcgag     660
accgtcacct gcaacgttgc ccacccggcc agcagcacca aggtggacaa gaaaattgtg     720
cccagggatt gtggttgtaa gccttgcata tgtacagtcc cagaagtatc atctgtcttc     780
atcttccccc caaagcccaa ggatgtgctc accattactc tgactcctaa ggtcacgtgt     840
gttgtggtag acatcagcaa ggatgatccc gaggtccagt tcagctggtt tgtagatgat     900
gtggaggtgc acacagctca gacgcaaccc cgggaggagc agttcaacag cactttccgc     960
tcagtcagtg aacttcccat catgcaccag gactggctca atggcaagga gttcaaatgc    1020
agggtcaaca gtgcagcttt ccctgccccc atcgagaaaa ccatctccaa aaccaaaggc    1080
agaccgaagg ctccacaggt gtacaccatt ccacctccca aggagcagat ggccaaggat    1140
```

```
aaagtcagtc tgacctgcat gataacagac ttcttccctg aagacattac tgtggagtgg      1200
cagtggaatg ggcagccagc ggagaactac aagaacactc agcccatcat gaacacgaat      1260
ggctcttact tcgtctacag caagctcaat gtgcagaaga gcaactggga ggcaggaaat      1320
actttcacct gctctgtgtt acatgagggc ctgcacaacc accatactga aagagcctc      1380 tcccactctc ctggtaaatg a                                                 1401
```

<210> SEQ ID NO 38
<211> LENGTH: 1563
<212> TYPE: DNA
<213> ORGANISM: Mus musculus

<400> SEQUENCE: 38

```
cctccatcag agcatggctg tcttggggct gctcttctgc ctggtgacat tcccaagctg        60
tgtcctctcc caggtgcagc tgaagcagtc aggacctggc ctagtgcagc cctcacagag       120
cctgtccatc acctgcacag tctctggttt ctcattaact aactatggtt tacactgggt       180
tcgccagtct ccaggaaagg gcctggagtg gctgggagtg atatggagtg gtggaagcac       240
agactataat gcagctttca tatccagact gagcatcagc aaggacaact ccaagagcca       300
agttttcttt aaaatgaaca gtctgcaggc tgatgacaca gccatatact actgtgccag       360
aaaaggaggg atctactatg ctaaccatta ctatgctatg gactactggg gtcaaggaac       420
ctcagtcacc gtctcctcag ccaaaacgac accccatct gtctatccac tggcccctgg       480
atctgctgcc caaactaact ccatggtgac cctgggatgc ctggtcaagg gctatttccc       540
tgagccagtg acagtgacct ggaactctgg atccctgtcc agcggtgtgc acaccttccc       600
agctgtcctg gagtctgacc tctacactct gagcagctca gtgactgtcc cctccagccc       660
tcggcccagc gagaccgtca cctgcaacgt tgcccacccg gccagcagca ccaaggtgga       720
caagaaaatt gtgcccaggg attgtggttg taagccttgc atatgtacag tcccagaagt       780
atcatctgtc ttcatcttcc ccccaaagcc caaggatgtg ctcaccatta ctctgactcc       840
taaggtcacg tgtgttgtgg tagacatcag caaggatgat cccgaggtcc agttcagctg       900
gtttgtagat gatgtggagg tgcacacagc tcagacgcaa ccccgggagg agcagttcaa       960
cagcactttc cgctcagtca gtgaacttcc catcatgcac caggactggc tcaatggcaa      1020
ggagttcaaa tgcagggtca acagtgcagc tttccctgcc cccatcgaga aaaccatctc      1080
caaaaccaaa ggcagaccga aggctccaca ggtgtacacc attccacctc caaggagca      1140 gatggccaag gataaagtca gtctgacctg catgataaca gacttcttcc ctgaagacat      1200
tactgtggag tggcagtgga atgggcagcc agcggagaac tacaagaaca ctcagcccat      1260
catgaacacg aatggctctt acttcgtcta cagcaagctc aatgtgcaga gagcaactg      1320 ggaggcagga atactttca cctgctctgt gttacatgag ggcctgcaca accaccatac      1380
tgagaagagc ctctcccact ctcctggtaa atgatcccag tgtccttgga gccctctggt      1440
cctacaggac tctgacacct acctccaccc ctccctgtat aaataaagca cccagcactg      1500
ccttgggacc ctgaaaaaaa aagaaaaaa aaaaaaaaa aaaaaaaaa aaaaaaaaa      1560 aaa                                                                    1563
```

<210> SEQ ID NO 39
<211> LENGTH: 240
<212> TYPE: PRT
<213> ORGANISM: Artificial
<220> FEATURE:

<223> OTHER INFORMATION: BV10 chimeric kappa light chain

<400> SEQUENCE: 39

Met Val Phe Thr Pro Gln Ile Leu Gly Leu Met Leu Phe Trp Ile Ser
1               5                   10                  15

Gly Ala Arg Gly Asp Ile Val Met Thr Gln Ser Pro Ser Ser Leu Ser
            20                  25                  30

Val Ser Ala Gly Glu Lys Val Thr Met Ser Cys Lys Ser Ser Gln Ser
        35                  40                  45

Leu Leu Asn Ser Gly Asn Gln Lys Asn Tyr Met Ala Trp Tyr Gln Gln
    50                  55                  60

Lys Pro Gly Gln Pro Pro Lys Leu Leu Ile Tyr Gly Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Asn Asp His Ser Tyr Pro Leu Thr Phe Gly Ala Gly Thr
        115                 120                 125

Lys Leu Glu Leu Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 40
<211> LENGTH: 723
<212> TYPE: DNA
<213> ORGANISM: Artificial
<220> FEATURE:
<223> OTHER INFORMATION: BV10 chimeric kappa light chain CDS

<400> SEQUENCE: 40
atggttttca cacctcagat acttggactt atgcttttt ggatttcagg tgctcgagga      60
gacattgtga tgacacagtc tccatcctcc ctgagtgtgt cagcaggaga aaggtcact     120 atgagctgca agtccagtca gagtctgtta acagtggaa atcaaaagaa ctatatggcc     180
tggtatcagc agaaaccagg gcagcctcct aaactgttga tctacggggc atccactagg     240
gaatctgggg tccctgatcg cttcacaggc agtggatctg gaaccgattt cactcttacc     300
atcagcagtg tgcaggctga agacctggca gtttattact gtcagaatga tcatagttat     360
ccgctcacgt tcggtgctgg gaccaagctg gagctgaaac ggactgtggc tgcaccatct     420
gtcttcatct tcccgccatc tgatgagcag ttgaaatctg gaactgcctc tgttgtgtgc     480
ctgctgaata acttctatcc cagagaggcc aaagtacagt ggaaggtgga taacgccctc     540
caatcgggta actcccagga gagtgtcaca gagcaggaca gcaaggacag cacctacagc     600

```
ctcagcagca ccctgacgct gagcaaagca gactacgaga acacaaagt ctacgcctgc    660 gaagtcaccc atcagggcct gagctcgccc gtcacaaaga gcttcaacag gggagagtgt    720
tag                                                                  723
```

<210> SEQ ID NO 41
<211> LENGTH: 472
<212> TYPE: PRT
<213> ORGANISM: Artificial
<220> FEATURE:
<223> OTHER INFORMATION: BV10 chimeric IgG gamma 1 heavy chain

<400> SEQUENCE: 41

```
Met Gly Trp Ser Trp Ile Phe Leu Phe Leu Leu Ser Gly Thr Ala Gly
1               5                   10                  15

Val Leu Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Asn Tyr Gly Leu His Trp Val Arg Gln Ser Pro Gly Lys Gly Leu
    50                  55                  60

Glu Trp Leu Gly Val Ile Trp Ser Gly Gly Ser Thr Asp Tyr Asn Ala
65                  70                  75                  80

Ala Phe Ile Ser Arg Leu Ser Ile Ser Lys Asp Asn Ser Lys Ser Gln
                85                  90                  95

Val Phe Phe Lys Met Asn Ser Leu Gln Ala Asp Asp Thr Ala Ile Tyr
            100                 105                 110

Tyr Cys Ala Arg Lys Gly Gly Ile Tyr Tyr Ala Asn His Tyr Tyr Ala
        115                 120                 125

Met Asp Tyr Trp Gly Gln Gly Thr Ser Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335
```

```
Asp Trp Leu Asn Gly Lys Glu Tyr Lys Cys Lys Val Ser Asn Lys Ala
            340                 345                 350
Leu Pro Ala Pro Ile Glu Lys Thr Ile Ser Lys Ala Lys Gly Gln Pro
        355                 360                 365
Arg Glu Pro Gln Val Tyr Thr Leu Pro Pro Ser Arg Asp Glu Leu Thr
    370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
            420                 425                 430
Ser Lys Leu Thr Val Asp Lys Ser Arg Trp Gln Gln Gly Asn Val Phe
        435                 440                 445
Ser Cys Ser Val Met His Glu Ala Leu His Asn His Tyr Thr Gln Lys
    450                 455                 460
Ser Leu Ser Leu Ser Pro Gly Lys
465                 470
```

<210> SEQ ID NO 42
<211> LENGTH: 1422
<212> TYPE: DNA
<213> ORGANISM: Artificial
<220> FEATURE:
<223> OTHER INFORMATION: BV10 chimeric IgG gamma 1 heavy chain CDS

<400> SEQUENCE: 42

```
atgggatgga gctggatctt tctctttctc ctgtcaggaa ctgcaggtgt cctctcccag    60
gtgcagctga agcagtcagg acctggccta gtgcagccct cacagagcct gtccatcacc   120
tgcacagtct ctggtttctc attaactaac tatggtttac actgggttcg ccagtctcca   180
ggaaagggcc tggagtggct gggagtgata tggagtggtg aagcacaga ctataatgca    240
gctttcatat ccagactgag catcagcaag acaactccca agagccaagt tttctttaaa   300
atgaacagtc tgcaggctga tgacacagcc atatactact gtgccagaaa aggagggatc   360
tactatgcta accattacta tgctatggac tactggggtc aaggaacctc agtcaccgtc   420
tcctcagcct ccaccaaggg cccatcggtc ttccccctgg cacctcctc caagagcacc    480
tctgggggca gcgcggccct gggctgtctg gtcaaggact acttccccga accggtgacg   540
gtgtcgtgga actcaggcgc cctgaccagc ggcgtgcaca ccttcccggc tgtcctacag   600
tcctcaggac tctactccct cagcagcgtg gtgaccgtgc cctccagcag cttgggcacc   660
cagacctaca tctgcaacgt gaatcacaag cccagcaaca ccaaggtgga caagaaagtt   720
gagcccaaat cttgtgacaa aactcacaca tgcccaccgt gcccagcacc tgaactcctg   780
ggggggccgt cagtcttcct cttccccccca aaacccaagg acaccctcat gatctcccgg   840
acccctgagg tcacatgcgt ggtggtggac gtgagccacg aagaccctga ggtcaagttc   900
aactggtacg tggacggcgt ggaggtgcat aatgccaaga caaagccgcg ggaggagcag   960
tacaacagca cgtatcgtgt ggtcagcgtc ctcaccgtcc tgcaccagga ctggctgaat  1020
ggcaaggagt acaagtgcaa ggtctccaac aaagccctcc cagcccccat cgagaaaacc  1080
atctccaaag ccaaagggca gccccgagaa ccacaggtgt acaccctgcc cccatcccgg  1140
gatgagctga ccaagaacca ggtcagcctg acctgcctgg tcaaaggctt ctatcccagc  1200
gacatcgccg tggagtggga gagcaatggg cagccggaga acaactacaa gaccacgcct  1260
```
cccgtgctgg actccgacgg ctccttcttc ctctacagca agctcaccgt ggacaagagc       1320
aggtggcagc aggggaacgt cttctcatgc tccgtgatgc atgaggctct gcacaaccac       1380
tacacgcaga agagcctctc cctgtctccg ggtaaatgat aa                          1422

<210> SEQ ID NO 43
<211> LENGTH: 472
<212> TYPE: PRT
<213> ORGANISM: Artificial
<220> FEATURE:
<223> OTHER INFORMATION: SDIE BV10 heavy chain

<400> SEQUENCE: 43

```
Met Gly Trp Ser Trp Ile Phe Leu Phe Leu Leu Ser Gly Thr Ala Gly
1               5                   10                  15

Val Leu Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Asn Tyr Gly Leu His Trp Val Arg Gln Ser Pro Gly Lys Gly Leu
    50                  55                  60

Glu Trp Leu Gly Val Ile Trp Ser Gly Gly Ser Thr Asp Tyr Asn Ala
65                  70                  75                  80

Ala Phe Ile Ser Arg Leu Ser Ile Ser Lys Asp Asn Ser Lys Ser Gln
                85                  90                  95

Val Phe Phe Lys Met Asn Ser Leu Gln Ala Asp Asp Thr Ala Ile Tyr
            100                 105                 110

Tyr Cys Ala Arg Lys Gly Gly Ile Tyr Tyr Ala Asn His Tyr Tyr Ala
        115                 120                 125

Met Asp Tyr Trp Gly Gln Gly Thr Ser Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Asp Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335
```

```
Asp Trp Leu Asn Gly Lys Glu Tyr Lys Cys Lys Val Ser Asn Lys Ala
            340                 345                 350
Leu Pro Ala Pro Glu Glu Lys Thr Ile Ser Lys Ala Lys Gly Gln Pro
        355                 360                 365
Arg Glu Pro Gln Val Tyr Thr Leu Pro Pro Ser Arg Asp Glu Leu Thr
    370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
            420                 425                 430
Ser Lys Leu Thr Val Asp Lys Ser Arg Trp Gln Gln Gly Asn Val Phe
        435                 440                 445
Ser Cys Ser Val Met His Glu Ala Leu His Asn His Tyr Thr Gln Lys
    450                 455                 460
Ser Leu Ser Leu Ser Pro Gly Lys
465                 470
```

<210> SEQ ID NO 44
<211> LENGTH: 1422
<212> TYPE: DNA
<213> ORGANISM: Artificial
<220> FEATURE:
<223> OTHER INFORMATION: SDIE BV10 heavy chain CDS

<400> SEQUENCE: 44

```
atgggatgga gctggatctt tctctttctc ctgtcaggaa ctgcaggtgt cctctcccag      60
gtgcagctga agcagtcagg acctggccta gtgcagccct cacagagcct gtccatcacc     120
tgcacagtct ctggtttctc attaactaac tatggtttac actgggttcg ccagtctcca     180
ggaaagggcc tggagtggct gggagtgata tggagtggtg aagcacaga ctataatgca      240 gctttcatat ccagactgag catcagcaag acaactcca agagccaagt tttctttaaa      300
atgaacagtc tgcaggctga tgacacagcc atatactact gtgccagaaa aggagggatc     360
tactatgcta accattacta tgctatggac tactggggtc aaggaacctc agtcaccgtc     420
tcctcagcct ccaccaaggg cccatcggtc ttccccctgg cacctcctc caagagcacc      480 tctgggggca gcggccct gggctgtctg gtcaaggact acttccccga accggtgacg       540
gtgtcgtgga actcaggcgc cctgaccagc ggcgtgcaca ccttcccggc tgtcctacag     600
tcctcaggac tctactccct cagcagcgtg gtgaccgtgc cctccagcag cttgggcacc     660
cagacctaca tctgcaacgt gaatcacaag cccagcaaca ccaaggtgga caagaaagtt     720
gagcccaaat cttgtgacaa aactcacaca tgcccaccgt gcccagcacc tgaactcctg     780
gggggcccgg atgtcttcct cttcccccca aaacccaagg acaccctcat gatctcccgg     840
acccctgagg tcacatgcgt ggtggtggac gtgagccacg aagaccctga ggtcaagttc     900
aactggtacg tggacggcgt ggaggtgcat aatgccaaga caaagccgcg ggaggagcag     960
tacaacagca cgtatcgtgt ggtcagcgtc ctcaccgtcc tgcaccagga ctggctgaat    1020
ggcaaggagt acaagtgcaa ggtctccaac aaagccctcc cagcccccga ggagaaaacc    1080
atctccaaag ccaaagggca gccccgagaa ccacaggtgt acaccctgcc cccatcccgg    1140
gatgagctga ccaagaacca ggtcagcctg acctgcctgg tcaaaggctt ctatcccagc    1200
gacatcgccg tggagtggga gagcaatggg cagccggaga acaactacaa gaccacgcct    1260
```
cccgtgctgg actccgacgg ctccttcttc ctctacagca agctcaccgt ggacaagagc    1320
aggtggcagc aggggaacgt cttctcatgc tccgtgatgc atgaggctct gcacaaccac    1380
tacacgcaga agagcctctc cctgtctccg ggtaaatgat aa    1422

<210> SEQ ID NO 45
<211> LENGTH: 25
<212> TYPE: DNA
<213> ORGANISM: Artificial
<220> FEATURE:
<223> OTHER INFORMATION: Oligonucleotide primer gamma1-for

<400> SEQUENCE: 45
caaggcttac aaccacaatc cctgg    25

<210> SEQ ID NO 46
<211> LENGTH: 29
<212> TYPE: DNA
<213> ORGANISM: Artificial
<220> FEATURE:
<223> OTHER INFORMATION: Oligonucleotide primer gamma1-back

<400> SEQUENCE: 46
catatgtaca gtcccagaag tatcatctg    29

<210> SEQ ID NO 47
<211> LENGTH: 31
<212> TYPE: DNA
<213> ORGANISM: Artificial
<220> FEATURE:
<223> OTHER INFORMATION: Oligonucleotide primer ck-for

<400> SEQUENCE: 47
tgttcaagaa gcacacgact gaggcacctc c    31

<210> SEQ ID NO 48
<211> LENGTH: 29
<212> TYPE: DNA
<213> ORGANISM: Artificial
<220> FEATURE:
<223> OTHER INFORMATION: Oligonucleotide primer ck-back

<400> SEQUENCE: 48
acttctaccc caaagacatc aatgtcaag    29

<210> SEQ ID NO 49
<211> LENGTH: 24
<212> TYPE: DNA
<213> ORGANISM: Artificial
<220> FEATURE:
<223> OTHER INFORMATION: Oligonucleotide primer k-for1

<400> SEQUENCE: 49
cctgttgaag ctcttgacaa tggg    24

<210> SEQ ID NO 50
<211> LENGTH: 24
<212> TYPE: DNA
<213> ORGANISM: Artificial
<220> FEATURE:
<223> OTHER INFORMATION: Oligonucleotide primer k-for2

<400> SEQUENCE: 50
atgtcttgtg agtggcctca cagg    24

-continued

```
<210> SEQ ID NO 51
<211> LENGTH: 23
<212> TYPE: DNA
<213> ORGANISM: Artificial
<220> FEATURE:
<223> OTHER INFORMATION: Oligonucleotide primer CG1-for1

<400> SEQUENCE: 51
cgtctacagc aagctcaatg tgc                                              23

<210> SEQ ID NO 52
<211> LENGTH: 21
<212> TYPE: DNA
<213> ORGANISM: Artificial
<220> FEATURE:
<223> OTHER INFORMATION: Oligonucleotide primer CG1-for2

<400> SEQUENCE: 52
ccatctgtct atccactggc c                                                21

<210> SEQ ID NO 53
<211> LENGTH: 23
<212> TYPE: DNA
<213> ORGANISM: Artificial
<220> FEATURE:
<223> OTHER INFORMATION: Oligonucleotide primer CG1-rev1

<400> SEQUENCE: 53
ccaggtcact gtcactggct cag                                              23

<210> SEQ ID NO 54
<211> LENGTH: 21
<212> TYPE: DNA
<213> ORGANISM: Artificial
<220> FEATURE:
<223> OTHER INFORMATION: Oligonucleotide primer CG1-rev2

<400> SEQUENCE: 54
cctcatgtaa cacagagcag g                                                21

<210> SEQ ID NO 55
<211> LENGTH: 53
<212> TYPE: DNA
<213> ORGANISM: Artificial
<220> FEATURE:
<223> OTHER INFORMATION: Oligonucleotide primer 4G8-H-for

<400> SEQUENCE: 55
tctcttcaca ggtgtcctct ctcaggtcca actgcagcag cctggggctg agc             53

<210> SEQ ID NO 56
<211> LENGTH: 52
<212> TYPE: DNA
<213> ORGANISM: Artificial
<220> FEATURE:
<223> OTHER INFORMATION: Oligonucleotide primer 4G8-H-rev

<400> SEQUENCE: 56
gagaaggtag gactcacctg aggagactgt gagagtggtg ccttggcccc ag              52

<210> SEQ ID NO 57
<211> LENGTH: 60
<212> TYPE: DNA
<213> ORGANISM: Artificial
<220> FEATURE:
<223> OTHER INFORMATION: Oligonucleotide primer BV10-H-for
```

```
<400> SEQUENCE: 57
agacgtccac tctgtctttc tcttcacagg tgtcctctcc caggtgcagc tgaagcagtc    60

<210> SEQ ID NO 58
<211> LENGTH: 49
<212> TYPE: DNA
<213> ORGANISM: Artificial
<220> FEATURE:
<223> OTHER INFORMATION: Oligonucleotide primer BV10-H-rev

<400> SEQUENCE: 58
gagaaggtag gactcacctg aggagacggt gactgaggtt ccttgaccc               49

<210> SEQ ID NO 59
<211> LENGTH: 40
<212> TYPE: DNA
<213> ORGANISM: Artificial
<220> FEATURE:
<223> OTHER INFORMATION: Oligonucleotide primer universal for (AatII)

<400> SEQUENCE: 59
agacgtccac tctgtctttc tcttcacagg tgtcctctcc                         40

<210> SEQ ID NO 60
<211> LENGTH: 33
<212> TYPE: DNA
<213> ORGANISM: Artificial
<220> FEATURE:
<223> OTHER INFORMATION: Oligonucleotide primer universal rev (ClaI)

<400> SEQUENCE: 60
tatcgattta gaatgggaga aggtaggact cac                                33

<210> SEQ ID NO 61
<211> LENGTH: 42
<212> TYPE: DNA
<213> ORGANISM: Artificial
<220> FEATURE:
<223> OTHER INFORMATION: Oligonucleotide primer 4G8-L-for (XhoI)

<400> SEQUENCE: 61
actcgaggag atattgtgct aactcagtct ccagccaccc tg                      42

<210> SEQ ID NO 62
<211> LENGTH: 41
<212> TYPE: DNA
<213> ORGANISM: Artificial
<220> FEATURE:
<223> OTHER INFORMATION: Oligonucleotide primer 4G8-L-rev (SpeI)

<400> SEQUENCE: 62
tactagtact tacgttttat ttccagcttg gtcccccctc c                       41

<210> SEQ ID NO 63
<211> LENGTH: 40
<212> TYPE: DNA
<213> ORGANISM: Artificial
<220> FEATURE:
<223> OTHER INFORMATION: Oligonucleotide primer BV10-L-for (XhoI)

<400> SEQUENCE: 63
actcgaggag acattgtgat gacacagtct ccatcctccc                         40

<210> SEQ ID NO 64
<211> LENGTH: 47
```

```
<212> TYPE: DNA
<213> ORGANISM: Artificial
<220> FEATURE:
<223> OTHER INFORMATION: Oligonucleotide primer BV10-L-rev (SpeI)

<400> SEQUENCE: 64
actagtactt acgtttcagc tccagcttgg tcccagcacc gaacgtg                47

<210> SEQ ID NO 65
<211> LENGTH: 952
<212> TYPE: PRT
<213> ORGANISM: Homo sapiens

<400> SEQUENCE: 65
```

| Met | Pro | Ala | Leu | Ala | Arg | Asp | Gly | Gly | Gln | Leu | Pro | Leu | Val | Val |
|---|---|---|---|---|---|---|---|---|---|---|---|---|---|---|
| 1 | | | | 5 | | | | | 10 | | | | | 15 |

| Phe | Ser | Ala | Met | Ile | Phe | Gly | Thr | Ile | Thr | Asn | Gln | Asp | Leu | Pro | Val |
|---|---|---|---|---|---|---|---|---|---|---|---|---|---|---|---|
| | | | 20 | | | | | 25 | | | | | 30 | | |

Ile Lys Cys Val Leu Ile Asn His Lys Asn Asn Asp Ser Ser Val Gly
         35                  40                  45

Lys Ser Ser Tyr Pro Met Val Ser Glu Ser Pro Glu Asp Leu Gly
 50                  55                  60

Cys Ala Leu Arg Pro Gln Asn Ser Gly Thr Val Tyr Glu Ala Ala Ala
 65                  70                  75                  80

Val Glu Val Asp Val Ser Ala Ser Ile Thr Leu Gln Val Leu Val Asp
                 85                  90                  95

Ala Pro Gly Asn Ile Ser Cys Leu Trp Val Phe Lys His Ser Ser Leu
             100                 105                 110

Asn Cys Gln Pro His Phe Asp Leu Gln Asn Arg Gly Val Val Ser Met
         115                 120                 125

Val Ile Leu Lys Met Thr Glu Thr Gln Ala Gly Glu Tyr Leu Leu Phe
     130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                 165                 170                 175

Glu Asn Gln Asp Ala Leu Val Cys Ile Ser Glu Ser Val Pro Glu Pro
             180                 185                 190

Ile Val Glu Trp Val Leu Cys Asp Ser Gln Gly Glu Ser Cys Lys Glu
         195                 200                 205

Glu Ser Pro Ala Val Val Lys Lys Glu Glu Lys Val Leu His Glu Leu
     210                 215                 220

Phe Gly Met Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
                 245                 250                 255

Leu Pro Gln Leu Phe Leu Lys Val Gly Glu Pro Leu Trp Ile Arg Cys
             260                 265                 270

Lys Ala Val His Val Asn His Gly Phe Gly Leu Thr Trp Glu Leu Glu
         275                 280                 285

Asn Lys Ala Leu Glu Glu Gly Asn Tyr Phe Glu Met Ser Thr Tyr Ser
     290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Lys His Pro
                 325                 330                 335

-continued

```
Ser Gln Ser Ala Leu Val Thr Ile Val Glu Lys Gly Phe Ile Asn Ala
            340                 345                 350

Thr Asn Ser Ser Glu Asp Tyr Glu Ile Asp Gln Tyr Glu Glu Phe Cys
            355                 360                 365

Phe Ser Val Arg Phe Lys Ala Tyr Pro Gln Ile Arg Cys Thr Trp Thr
370                 375                 380

Phe Ser Arg Lys Ser Phe Pro Cys Glu Gln Lys Gly Leu Asp Asn Gly
385                 390                 395                 400

Tyr Ser Ile Ser Lys Phe Cys Asn His Lys His Gln Pro Gly Glu Tyr
                405                 410                 415

Ile Phe His Ala Glu Asn Asp Asp Ala Gln Phe Thr Lys Met Phe Thr
            420                 425                 430

Leu Asn Ile Arg Arg Lys Pro Gln Val Leu Ala Glu Ala Ser Ala Ser
            435                 440                 445

Gln Ala Ser Cys Phe Ser Asp Gly Tyr Pro Leu Pro Ser Trp Thr Trp
        450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
                485                 490                 495

Ser Ser Ser Thr Leu Asn Met Ser Glu Ala Ile Lys Gly Phe Leu Val
            500                 505                 510

Lys Cys Cys Ala Tyr Asn Ser Leu Gly Thr Ser Cys Glu Thr Ile Leu
        515                 520                 525

Leu Asn Ser Pro Gly Pro Phe Pro Phe Ile Gln Asp Asn Ile Ser Phe
    530                 535                 540

Tyr Ala Thr Ile Gly Val Cys Leu Leu Phe Ile Val Val Leu Thr Leu
545                 550                 555                 560

Leu Ile Cys His Lys Tyr Lys Lys Gln Phe Arg Tyr Glu Ser Gln Leu
                565                 570                 575

Gln Met Val Gln Val Thr Gly Ser Ser Asp Asn Glu Tyr Phe Tyr Val
            580                 585                 590

Asp Phe Arg Glu Tyr Glu Tyr Asp Leu Lys Trp Glu Phe Pro Arg Glu
            595                 600                 605

Asn Leu Glu Phe Gly Lys Val Leu Gly Ser Gly Ala Phe Gly Lys Val
            610                 615                 620

Met Asn Ala Thr Ala Tyr Gly Ile Ser Lys Thr Gly Val Ser Ile Gln
625                 630                 635                 640

Val Ala Val Lys Met Leu Lys Glu Lys Ala Asp Ser Ser Glu Arg Glu
                645                 650                 655

Ala Leu Met Ser Glu Leu Lys Met Met Thr Gln Leu Gly Ser His Glu
            660                 665                 670

Asn Ile Val Asn Leu Leu Gly Ala Cys Thr Leu Ser Gly Pro Ile Tyr
            675                 680                 685

Leu Ile Phe Glu Tyr Cys Cys Tyr Gly Asp Leu Leu Asn Tyr Leu Arg
            690                 695                 700

Ser Lys Arg Glu Lys Phe His Arg Thr Trp Thr Glu Ile Phe Lys Glu
705                 710                 715                 720

His Asn Phe Ser Phe Tyr Pro Thr Phe Gln Ser His Pro Asn Ser Ser
                725                 730                 735

Met Pro Gly Ser Arg Glu Val Gln Ile His Pro Asp Ser Asp Gln Ile
            740                 745                 750
```

```
Ser Gly Leu His Gly Asn Ser Phe His Ser Glu Asp Glu Ile Glu Tyr
        755                 760                 765
Glu Asn Gln Lys Arg Leu Glu Glu Glu Asp Leu Asn Val Leu Thr
    770                 775                 780
Phe Glu Asp Leu Leu Cys Phe Ala Tyr Gln Val Ala Lys Gly Met Glu
785                 790                 795                 800
Phe Leu Glu Phe Lys Ser Ala Arg Leu Pro Val Lys Trp Met Ala Pro
                805                 810                 815
Glu Ser Leu Phe Glu Gly Ile Tyr Thr Ile Lys Ser Asp Val Trp Ser
                820                 825                 830
Tyr Gly Ile Leu Leu Trp Glu Ile Phe Ser Leu Gly Val Asn Pro Tyr
        835                 840                 845
Pro Gly Ile Pro Val Asp Ala Asn Phe Tyr Lys Leu Ile Gln Asn Gly
    850                 855                 860
Phe Lys Met Asp Gln Pro Phe Tyr Ala Thr Glu Glu Ile Tyr Ile Ile
865                 870                 875                 880
Met Gln Ser Cys Trp Ala Phe Asp Ser Arg Lys Arg Pro Ser Phe Pro
                885                 890                 895
Asn Leu Thr Ser Phe Leu Gly Cys Gln Leu Ala Asp Ala Glu Glu Ala
                900                 905                 910
Met Tyr Gln Asn Val Asp Gly Arg Val Ser Glu Cys Pro His Thr Tyr
                915                 920                 925
Gln Asn Arg Arg Pro Phe Ser Arg Glu Met Asp Leu Gly Leu Leu Ser
            930                 935                 940
Pro Gln Ala Gln Val Glu Asp Ser
945                 950

<210> SEQ ID NO 66
<211> LENGTH: 24
<212> TYPE: PRT
<213> ORGANISM: Artificial
<220> FEATURE:
<223> OTHER INFORMATION: M-Tag; amino acids #455-466 of the human Ig
      alpha 1 tailpiece and c-myc epitope

<400> SEQUENCE: 66

Pro Thr His Val Asn Val Ser Val Val Met Ala Glu Glu Gln Lys Leu
1               5                   10                  15
Ile Ser Glu Glu Asp Leu Leu Arg
            20

<210> SEQ ID NO 67
<211> LENGTH: 12
<212> TYPE: PRT
<213> ORGANISM: Artificial
<220> FEATURE:
<223> OTHER INFORMATION: amino acids 455-466 of the human Ig alpha 1
      tailpiece

<400> SEQUENCE: 67

Pro Thr His Val Asn Val Ser Val Val Met Ala Glu
1               5                   10

<210> SEQ ID NO 68
<211> LENGTH: 12
<212> TYPE: PRT
<213> ORGANISM: artificial
<220> FEATURE:
<223> OTHER INFORMATION: c-myc epitope
```

```
<400> SEQUENCE: 68

Glu Gln Lys Leu Ile Ser Glu Glu Asp Leu Leu Arg
1               5                   10
```